(12) United States Patent
Fotouhi et al.

(10) Patent No.: US 7,964,724 B2
(45) Date of Patent: *Jun. 21, 2011

(54) CHIRAL CIS-IMIDAZOLINES

(75) Inventors: Nader Fotouhi, Basking Ridge, NJ (US); Gregory Jay Haley, San Diego, CA (US); Klaus B. Simonsen, Frederiksberg (DK); Binh Thanh Vu, North Caldwell, NJ (US); Stephen Evan Webber, San Diego, CA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.
This patent is subject to a terminal disclaimer.

(21) Appl. No.: 11/129,621

(22) Filed: May 13, 2005

(65) Prior Publication Data
US 2005/0288287 A1 Dec. 29, 2005

Related U.S. Application Data

(60) Provisional application No. 60/572,275, filed on May 18, 2004, provisional application No. 60/615,534, filed on Oct. 1, 2004, provisional application No. 60/668,772, filed on Apr. 6, 2005.

(51) Int. Cl.
*A61K 31/4178* (2006.01)
*C07D 233/22* (2006.01)
*C07D 401/06* (2006.01)

(52) U.S. Cl. ............. 544/121; 544/370; 548/334.1; 514/396; 514/397

(58) Field of Classification Search ............ 548/334.1; 544/121, 370
See application file for complete search history.

(56) References Cited

U.S. PATENT DOCUMENTS

| | | | |
|---|---|---|---|
| 5,457,224 A | 10/1995 | Ehrmann et al. | |
| 5,925,665 A | 7/1999 | Payard et al. | |
| 6,617,346 B1 | 9/2003 | Kong et al. | |
| 6,734,302 B2 | 5/2004 | Kong et al. | |

FOREIGN PATENT DOCUMENTS

| | | |
|---|---|---|
| EP | 363 061 | 4/1990 |
| WO | WO 00/78725 | 12/2000 |
| WO | 03/002509 | 1/2003 |
| WO | WO 03/051359 | 6/2003 |

OTHER PUBLICATIONS

Hunter et al., Can. J. Chem., 50, pp. 669-677 (1972).
Wells et al., J. Org. Chem., 37, pp. 2158-2161 (1972).
Vassilev et al., Science, 303, pp. 844-848 (2004).
McCapra et al., Photochem. and Photobiol., 4, pp. 1111-1121 (1965).
Moormann, et al., Journal of Medicinal Chemistry, vol. 33, No. (2), pp. 614-626 (1990).
Japanese Office Action in related case JP 2007-517027 dated Jul. 8, 2010.

*Primary Examiner* — Laura L. Stockton
(74) *Attorney, Agent, or Firm* — George W. Johnston; Patricia S. Rocha-Tramaloni

(57) ABSTRACT

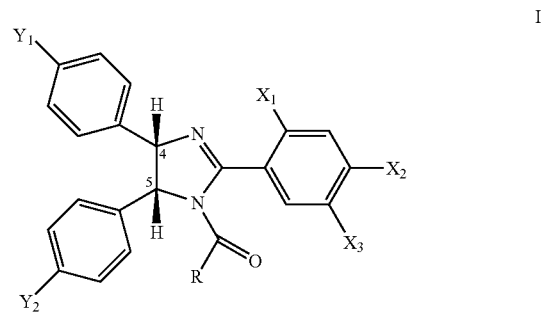

and the pharmaceutically acceptable salts and esters thereof, wherein $X_1, X_2, X_3, Y_1, Y_2$ and R are described herein inhibit the interaction of MDM2 protein with a p53-like peptide and hence have anti proliferative activity.

10 Claims, No Drawings

CHIRAL CIS-IMIDAZOLINES

PRIORITY TO RELATED APPLICATIONS

This application claims the benefit of provisional Application(s) Ser. No. 60/572,275, filed May 18, 2004; Ser. No. 60/615,534 filed Oct. 1, 2004 and Ser. No. 60/668,772, filed Apr. 6, 2005.

FIELD OF THE INVENTION

This invention is related to at least one compound selected from a compound of formula I

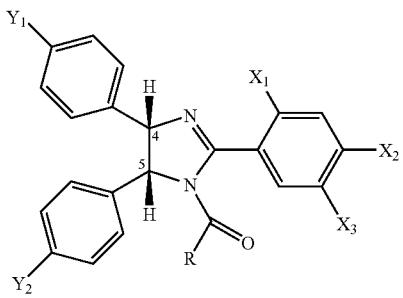

I or the pharmaceutically acceptable salts thereof, wherein $X_1$, $X_2$, $X_3$, R, $Y_1$ and $Y_2$ are described in this application. These compounds are believed to inhibit the interaction of MDM2 protein with a p-53-like peptide and have antiproliferative activity.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.*, 1972, 37, 2158-2161, report synthesis of imidazolines. Hunter et al., *Can. J. Chem.*, 1972, Vol. 50, pgs. 669-77, report the preparation of amarine and isoamarine compounds which had previously been studied for chemiluminescence (McCapra et al. *Photochem. and Photobiol.* 1965, 4, 1111-1121). Zupanc et al. *Bull. Soc. Chem. & Tech.* (Yugoslavia) 1980-81, 27/28, 71-80, report the use of triaryl imidazolines as starting materials in the preparation of EDTA derivatives.

EP 363 061 to Matsumoto reports imidazoline derivatives useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

U.S. Pat. No. 6,617,346 B1 issued Sep. 9, 2003 and U.S. Pat. No. 6,734,302 B2 issued May 11, 2004 disclose related racemic cis-imidazolines.

SUMMARY OF THE INVENTION

The present invention provides at least one compound of formula I

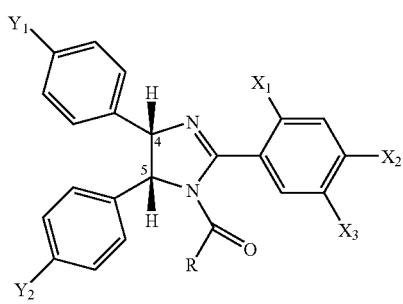

I and the pharmaceutically acceptable salts and esters thereof wherein $X_1$, $X_2$, $X_3$, R, $Y_1$, and $Y_2$ are as herein described.

DETAILED DESCRIPTION OF THE INVENTION

The present invention provides chiral cis-imidazolines which are small molecule inhibitors of the MDM2-p53 interaction. In cell-free and cell-based assays, compounds of the present invention are shown to inhibit the interaction of MDM2 protein with a p53-like peptide with a potency that is approximately 100 fold greater than a p53-derived peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

The present invention provides at least one compound of formula I

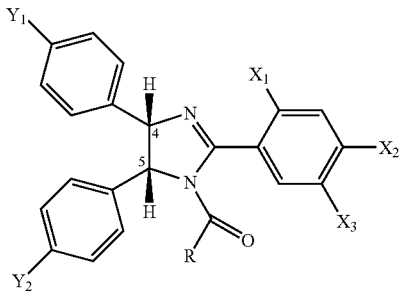

and the pharmaceutically acceptable salts and esters thereof, wherein
$X_1$ is selected from the group consisting of lower alkoxy, and lower alkoxy substituted by trifluoromethyl or fluorine;
$X_2$ is selected from the group consisting of hydrogen, halogen, lower alkyl, and —$C(X_4X_5)$—$X_6$;
$X_3$ is selected from the group consisting of hydrogen, lower alkoxy, halogen, and —$C(X_4X_5)$—$X_6$; with the proviso that when $X_2$ is hydrogen, halogen or lower alkyl, $X_3$ is —$C(X_4X_5)$—$X_6$;
$X_4$ and $X_5$ are lower alkyl and can be connected together to form a cycloalkyl;
$X_6$ is selected from the group consisting of lower alkyl, cyano, —$CH_2$—OH, —$CH_2$—O-lower alkyl, —$CH_2$—O-lower alkyl substituted by lower alkoxy, —$C(O)X_7$, and —$CH_2$—$NX_8X_9$;
$X_7$ is selected from the group consisting of hydroxy, lower alkoxy, morpholino, and —$NX_8X_9$;
$X_8$ and $X_9$ are independently selected from the group consisting of hydrogen, lower alkyl, lower alkyl substituted by lower alkoxy or cyano, and lower alkoxy;
$Y_1$ and $Y_2$ are independently selected from the group consisting of halogen, cyano, and acetylene;
R is selected from the group consisting of piperidinyl substituted by five or six membered heterocycle, piperidinyl substituted by —$NX_8X_9$, and

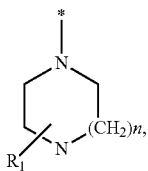

wherein
n=1 or 2,
$R_1$ can be one or more substituents selected from the group consisting of hydrogen, oxo, lower alkyl substituted by $R_2$, —$C(O)R_3$, and —$SO_2$-lower alkyl;
$R_2$ is selected from the group consisting of hydroxy, lower alkoxy, trifluoromethyl, -cyano, —NH—$SO_2$-lower alkyl, —NH—C(O)-lower alkyl, —C(O)-lower alkyl, —$C(O)R_4$, —C(O)—$NX_8X_9$, —$SO_2$-lower alkyl, —$SO_2$—$NX_8X_9$,
$R_3$ is selected from the group consisting of five membered heterocycle, lower alkyl, lower alkoxy, and lower alkyl substituted by lower alkoxy;
$R_4$ is selected from the group consisting of hydroxy, lower alkoxy, morpholino, and —$NX_8X_9$;

Preferred compounds are compounds of formula I wherein $Y_1$ and $Y_2$ are each independently selected from —Cl and —Br.

Further preferred compounds are compounds of formula I wherein R is piperazinyl substituted by oxo or lower alkyl substituted by $R_2$.

Also preferred compounds are compounds in which the two hydrogen atoms of the imidazoline ring are in a cis configuration to each other. The compounds may be in a racemic form and may be optically active. The preferred absolute stereochemistry at the 4 and 5 position of the imidazoline ring are S and R, respectively.

Such compounds are for example:
[(4S,5R)-2-(4-tert-Butyl-2-ethoxy-phenyl)-4,5-bis-(4-fluoro-phenyl)-4,5-dihydro-imidazol-1-yl]-[4-(2-methanesulfonyl-ethyl)-piperazin-1-yl]-methanone hydrochloride;
4-[(4S,5R)-2-(4-tert-Butyl-2-ethoxy-phenyl)-4,5-bis-(4-fluoro-phenyl)-4,5-dihydro-imidazole-1-carbonyl]-piperazin-2-one hydrochloride;
2-{4-[(4S,5R)-2-(4-tert-Butyl-2-ethoxy-phenyl)-4,5-bis-(4-fluoro-phenyl)-4,5-dihydro-imidazole-1-carbonyl]-piperazin-1-yl}-1-morpholin-4-yl-ethanone hydrochloride;
2-{4-[(4S,5R)-2-(4-tert-Butyl-2-ethoxy-phenyl)-4,5-bis-(4-fluoro-phenyl)-4,5-dihydro-imidazole-1-carbonyl]-piperazin-1-yl}-N,N-dimethyl-acetamide hydrochloride;
4-[(4S,5R)-4,5-Bis-(4-bromo-phenyl)-2-(4-tert-butyl-2-ethoxy-phenyl)-4,5-dihydro-imidazole-1-carbonyl]-piperazin-2-one;
1-[(4S,5R)-4,5-Bis-(4-bromo-phenyl)-2-(4-tert-butyl-2-ethoxy-phenyl)-4,5-dihydro-imidazole-1-carbonyl]-[1,4]diazepan-5-one;
[(4S,5R)-4,5-Bis-(4-bromo-phenyl)-2-(4-tert-butyl-2-ethoxy-phenyl)-4,5-dihydro-imidazol-1-yl]-[4-(2-methanesulfonyl-ethyl)-piperazin-1-yl]-methanone hydrochloride;
2-{4-[(4S,5R)-4,5-Bis-(4-bromo-phenyl)-2-(4-tert-butyl-2-ethoxy-phenyl)-4,5-dihydro-imidazole-1-carbonyl]-piperazin-1-yl}-1-morpholin-4-yl-ethanone hydrochloride;
4-[(4S,5R)-2-(4-tert-Butyl-2-ethoxy-phenyl)-4,5-bis-(4-ethynyl-phenyl)-4,5-dihydro-imidazole-1-carbonyl]-piperazin-2-one;
[(4S,5R)-2-(4-tert-Butyl-2-ethoxy-phenyl)-4,5-bis-(4-ethynyl-phenyl)-4,5-dihydro-imidazol-1-yl]-[4-(2-methanesulfonyl-ethyl)-piperazin-1-yl]-methanone hydrochloride;
2-{4-[(4S,5R)-2-(4-tert-Butyl-2-ethoxy-phenyl)-4,5-bis-(4-ethynyl-phenyl)-4,5-dihydro-imidazole-1-carbonyl]-piperazin-1-yl}-1-morpholin-4-yl-ethanone hydrochloride;
4-[(4S,5R)-2-(5-tert-Butyl-2-ethoxy-phenyl)-4,5-bis-(4-chloro-phenyl)-4,5-dihydro-imidazole-1-carbonyl]-piperazin-2-one;
1-[(4S,5R)-2-(5-tert-Butyl-2-ethoxy-phenyl)-4,5-bis-(4-chloro-phenyl)-4,5-dihydro-imidazole-1-carbonyl]-[1,4]diazepan-5-one;
[(4S,5R)-2-(5-tert-Butyl-2-ethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride;
2-{4-[(4S,5R)-2-(5-tert-Butyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride;
2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N-tert-butyl-acetamide;

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-acetamide;

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N,N-bis-(2-methoxy-ethyl)-acetamide;

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N-(2-methoxy-1-methyl-ethyl)-acetamide;

2-(3-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-phenyl)-2-methyl-propionitrile;

2-{3-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-phenyl}-2-methyl-propionitrile;

N-[2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-ethyl]-methanesulfonamide;

2-(3-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-phenyl)-2-methyl-propionitrile;

2-(3-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-phenyl)-2-methyl-propionitrile;

2-(3-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-phenyl)-2-methyl-propionitrile;

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N,N-dimethyl-acetamide;

4-[(4S,5R)-2-(4-tert-Butyl-2-ethoxy-phenyl)-4,5-bis-(4-chloro-phenyl)-4,5-dihydro-imidazole-1-carbonyl]-piperazin-2-one hydrochloride;

[(4S,5R)-2-(4-tert-Butyl-2-ethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-N,N-dimethyl-acetamide hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride;

1-[(4S,5R)-2-(4-tert-Butyl-2-ethoxy-phenyl)-4,5-bis-(4-chloro-phenyl)-4,5-dihydro-imidazole-1-carbonyl]-[1,4]diazepan-5-one hydrochloride;

4-[(4S,5R)-2-(4-tert-Butyl-2,5-diethoxy-phenyl)-4,5-bis-(4-chloro-phenyl)-4,5-dihydro-imidazole-1-carbonyl]-piperazin-2-one hydrochloride;

[(4S,5R)-2-(4-tert-Butyl-2,5-diethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride;

2-{4-[(4S,5R)-2-(4-tert-Butyl-2,5-diethoxy-phenyl)-4,5-bis-(4-chloro-phenyl)-4,5-dihydro-imidazole-1-carbonyl]-piperazin-1-yl}-1-morpholin-4-yl-ethanone hydrochloride;

2-{4-[(4S,5R)-2-(4-tert-Butyl-2,5-diethoxy-phenyl)-4,5-bis-(4-chloro-phenyl)-4,5-dihydro-imidazole-1-carbonyl]-piperazin-1-yl}-N,N-dimethyl-acetamide hydrochloride;

1-[(4S,5R)-2-(4-tert-Butyl-2,5-diethoxy-phenyl)-4,5-bis-(4-chloro-phenyl)-4,5-dihydro-imidazole-1-carbonyl]-[1,4]diazepan-5-one hydrochloride;

4-[(4S,5R)-2-(4-tert-Butyl-2-ethoxy-phenyl)-4,5-bis-(4-chloro-phenyl)-4,5-dihydro-imidazole-1-carbonyl]-piperazine-1-carboxylic acid tert-butyl ester;

1-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-ethanone hydrochloride;

[(4S,5R)-2-(4-tert-Butyl-2-ethoxy-phenyl)-4,5-bis-(4-chloro-phenyl)-4,5-dihydro-imidazol-1-yl]-[4-(2-methoxy-ethyl)-piperazin-1-yl]-methanone hydrochloride;

[(4S,5R)-2-(4-tert-Butyl-2-ethoxy-phenyl)-4,5-bis-(4-chloro-phenyl)-4,5-dihydro-imidazol-1-yl]-[4-(2-hydroxy-ethyl)-piperazin-1-yl]-methanone hydrochloride;

[(4S,5R)-2-(4-tert-Butyl-2-ethoxy-phenyl)-4,5-bis-(4-chloro-phenyl)-4,5-dihydro-imidazol-1-yl]-piperazin-1-yl-methanone hydrochloride;

1-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-2-methoxy-ethanone;

[(4S,5R)-2-(4-tert-Butyl-2-ethoxy-phenyl)-4,5-bis-(4-chloro-phenyl)-4,5-dihydro-imidazol-1-yl]-[4-(2-hydroxy-2-methyl-propyl)-piperazin-1-yl]-methanone hydrochloride;

[(4S,5R)-2-(4-tert-Butyl-2-ethoxy-phenyl)-4,5-bis-(4-chloro-phenyl)-4,5-dihydro-imidazol-1-yl]-[4-(3,3,3-trifluoro-2-hydroxy-propyl)-piperazin-1-yl]-methanone hydrochloride;

4-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-butan-2-one hydrochloride;

[(4S,5R)-2-(4-tert-Butyl-2-ethoxy-phenyl)-4,5-bis-(4-chloro-phenyl)-4,5-dihydro-imidazol-1-yl]-(4-pyrrolidin-1-yl-piperidin-1-yl)-methanone hydrochloride;

3-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-propionic acid hydrochloride;

3-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-propionitrile hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-acetamide hydrochloride;

N-tert-Butyl-2-{4-[(4S,5R)-2-(4-tert-butyl-2-ethoxy-phenyl)-4,5-bis-(4-chloro-phenyl)-4,5-dihydro-imidazole-1-carbonyl]-piperazin-1-yl}-acetamide hydrochloride;

{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-acetonitrile hydrochloride;

[(4S,5R)-2-(4-tert-Butyl-2-ethoxy-phenyl)-4,5-bis-(4-chloro-phenyl)-4,5-dihydro-imidazol-1-yl]-[4-(2,2,2-trifluoro-ethyl)-piperazin-1-yl]-methanone hydrochloride;

[(4S,5R)-2-(4-tert-Butyl-2-ethoxy-phenyl)-4,5-bis-(4-chloro-phenyl)-4,5-dihydro-imidazol-1-yl]-[4-(3,3,3-trifluoro-propyl)-piperazin-1-yl]-methanone hydrochloride;

[(4S,5R)-2-(4-tert-Butyl-2-ethoxy-phenyl)-4,5-bis-(4-chloro-phenyl)-4,5-dihydro-imidazol-1-yl]-(4-methanesulfonyl-piperazin-1-yl)-methanone;

4-[(4S,5R)-2-(4-tert-Butyl-2-ethoxy-phenyl)-4,5-bis-(4-chloro-phenyl)-4,5-dihydro-imidazole-1-carbonyl]-1-(2-methanesulfonyl-ethyl)-piperazin-2-one;

1-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-3,3-dimethyl-butan-2-one hydrochloride;

[(4S,5R)-2-(4-tert-Butyl-2-ethoxy-phenyl)-4,5-bis-(4-chloro-phenyl)-4,5-dihydro-imidazol-1-yl]-[4-(3-methanesulfonyl-propyl)-piperazin-1-yl]-methanone hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-[1,4]diazepan-1-yl}-1-morpholin-4-yl-ethanone hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-[1,4]diazepan-1-yl}-N,N-dimethyl-acetamide hydrochloride;

[(4S,5R)-2-(4-tert-Butyl-2-ethoxy-phenyl)-4,5-bis-(4-chloro-phenyl)-4,5-dihydro-imidazol-1-yl]-[4-(2-methanesulfonyl-ethyl)-[1,4]diazepan-1-yl]-methanone hydrochloride;

N-(2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-ethyl)-methanesulfonamide hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-N-methoxy-N-methyl-acetamide hydrochloride;

4-{(4S,5R)-4,5-Bis-(4-chloro-phenyl)-2-[2-ethoxy-4-(2-hydroxy-1,1-dimethyl-ethyl)-phenyl]-4,5-dihydro-imidazole-1-carbonyl}-piperazin-2-one;

{(4S,5R)-4,5-Bis-(4-chloro-phenyl)-2-[2-ethoxy-4-(2-hydroxy-1,1-dimethyl-ethyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-4-(2-hydroxy-1,1-dimethyl-ethyl)-phenyl]-4,5-dihydro-imidazole-1-carbonyl}-piperazin-1-yl)-1-morpholin-4-yl-ethanone hydrochloride;

2-(4-{(4S,5R)-4,5-Bis-(4-chloro-phenyl)-2-[2-ethoxy-4-(2-hydroxy-1,1-dimethyl-ethyl)-phenyl]-4,5-dihydro-imidazole-1-carbonyl}-piperazin-1-yl)-N-methoxy-N-methyl-acetamide hydrochloride;

{(4S,5R)-4,5-Bis-(4-chloro-phenyl)-2-[2-ethoxy-4-(2-hydroxy-1,1-dimethyl-ethyl)-phenyl]-4,5-dihydro-imidazol-1-yl}-[4-(3-methanesulfonyl-propyl)-piperazin-1-yl]-methanone hydrochloride;

[(4S,5R)-2-(4-tert-Butyl-5-chloro-2-ethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride;

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-N,N-dimethyl-acetamide hydrochloride;

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride;

4-[(4S,5R)-2-(4-tert-Butyl-2-isopropoxy-phenyl)-4,5-bis-(4-chloro-phenyl)-4,5-dihydro-imidazole-1-carbonyl]-piperazin-2-one;

[(4S,5R)-2-(4-tert-Butyl-2-isopropoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride;

[(4S,5R)-2-(4-tert-Butyl-2-isopropoxy-phenyl)-4,5-bis-(4-chloro-phenyl)-4,5-dihydro-imidazol-1-yl]-[4-(3-methanesulfonyl-propyl)-piperazin-1-yl]-methanone hydrochloride;

N-(2-{4-[(4S,5R)-2-(4-tert-Butyl-2-isopropoxy-phenyl)-4,5-bis-(4-chloro-phenyl)-4,5-dihydro-imidazole-1-carbonyl]-piperazin-1-yl}-ethyl)-methanesulfonamide hydrochloride;

2-{4-[(4S,5R)-2-(4-tert-Butyl-2-isopropoxy-phenyl)-4,5-bis-(4-chloro-phenyl)-4,5-dihydro-imidazole-1-carbonyl]-piperazin-1-yl}-N,N-dimethyl-acetamide hydrochloride;

2-{4-[(4S,5R)-2-(4-tert-Butyl-2-isopropoxy-phenyl)-4,5-bis-(4-chloro-phenyl)-4,5-dihydro-imidazole-1-carbonyl]-piperazin-1-yl}-1-morpholin-4-yl-ethanone hydrochloride;

[(4S,5R)-2-(4-tert-Butyl-5-chloro-2-ethoxy-phenyl)-4,5-bis-(4-chloro-phenyl)-4,5-dihydro-imidazol-1-yl]-[4-(3-methanesulfonyl-propyl)-piperazin-1-yl]-methanone hydrochloride;

N-(2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-ethyl)-methanesulfonamide hydrochloride;

[(4S,5R)-2-(4-tert-Butyl-5-chloro-2-ethoxy-phenyl)-4,5-bis-(4-chloro-phenyl)-4,5-dihydro-imidazol-1-yl]-(4-ethanesulfonyl-piperazin-1-yl)-methanone hydrochloride;

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-N-methoxy-N-methyl-acetamide hydrochloride;

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-N-isopropyl-N-methyl-acetamide hydrochloride;

4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-2-one;

N-(2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-ethyl)-acetamide hydrochloride;

N-(2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-ethyl)-acetamide hydrochloride;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-tert-butyl-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N,N-bis-(2-methoxy-ethyl)-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-(2-methoxy-1-methyl-ethyl)-acetamide;

2-(4-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-3-ethoxy-phenyl)-2-methyl-propionitrile;

2-{4-[(4S,5R)-4,5-Bis-(4-chloro-phenyl)-1-(4-ethanesulfonyl-piperazine-1-carbonyl)-4,5-dihydro-1H-imidazol-2-yl]-3-ethoxy-phenyl}-2-methyl-propionitrile;

N-[2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-ethyl]-methanesulfonamide;

2-(4-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-3-ethoxy-phenyl)-2-methyl-propionitrile;

2-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-2-methyl-propionitrile;

2-(4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-phenyl)-2-methyl-propionitrile;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N,N-dimethyl-acetamide;

N-tert-Butyl-2-{4-[(4S,5R)-2-[5-chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N,N-bis-(2-methoxy-ethyl)-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-methoxy-N-methyl-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-isopropyl-N-methyl-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-(2-cyano-ethyl)-N-methyl-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-(2-methoxy-1-methyl-ethyl)-acetamide;

2-(4-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-2-chloro-5-ethoxy-phenyl)-2-methyl-propionitrile;

2-{4-[(4S,5R)-4,5-Bis-(4-chloro-phenyl)-1-(4-ethanesulfonyl-piperazine-1-carbonyl)-4,5-dihydro-1H-imidazol-2-yl]-2-chloro-5-ethoxy-phenyl}-2-methyl-propionitrile;

N-(2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-ethyl)-methanesulfonamide;

2-(4-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-2-chloro-5-ethoxy-phenyl)-2-methyl-propionitrile;

2-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-5-ethoxy-phenyl)-2-methyl-propionitrile;

2-(4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-5-ethoxy-phenyl)-2-methyl-propionitrile;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N,N-dimethyl-acetamide;

4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-2-one;

[(4S,5R)-2-[4-tert-Butyl-2-(2,2,2-trifluoro-ethoxy)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;

[(4S,5R)-2-[4-tert-Butyl-2-(2,2,2-trifluoro-ethoxy)-phenyl]-4,5-bis-(4-chloro-phenyl)-4,5-dihydro-imidazol-1-yl]-[4-(3-methanesulfonyl-propyl)-piperazin-1-yl]-methanone hydrochloride;

N-(2-{4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-1-yl}-ethyl)-acetamide hydrochloride;

2-{4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-1-yl}-N,N-dimethyl-acetamide hydrochloride;

2-{4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-1-yl}-1-morpholin-4-yl-ethanone hydrochloride;

2-{4-[(4S,5R)-2-[4-tert-Butyl-2-(2-fluoro-ethoxy)-phenyl]-4,5-bis-(4-chloro-phenyl)-4,5-dihydro-imidazole-1-carbonyl]-piperazin-1-yl}-1-morpholin-4-yl-ethanone hydrochloride;

[(4S,5R)-2-[4-tert-Butyl-2-(2-fluoro-ethoxy)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;

[1,4']Bipiperidinyl-1'-yl-[(4S,5R)-2-(4-tert-butyl-2-ethoxy-phenyl)-4,5-bis-(4-chloro-phenyl)-4,5-dihydro-imidazol-1-yl]-methanone;

[(4S,5R)-2-(4-tert-Butyl-2-ethoxy-phenyl)-4,5-bis-(4-chloro-phenyl)-4,5-dihydro-imidazol-1-yl]-(4-morpholin-4-yl-piperidin-1-yl)-methanone;

4-{(4S,5R)-4,5-Bis-(4-chloro-phenyl)-2-[2-ethoxy-4-(2-methoxy-1,1-dimethyl-ethyl)-phenyl]-4,5-dihydro-imidazole-1-carbonyl}-piperazin-2-one;

{(4S,5R)-4,5-Bis-(4-chloro-phenyl)-2-[2-ethoxy-4-(2-methoxy-1,1-dimethyl-ethyl)-phenyl]-4,5-dihydro-imidazol-1-yl}-[4-(2-methanesulfonyl-ethyl)-piperazin-1-yl]-methanone;

2-(4-{(4S,5R)-4,5-Bis-(4-chloro-phenyl)-2-[2-ethoxy-4-(2-methoxy-1,1-dimethyl-ethyl)-phenyl]-4,5-dihydro-imidazole-1-carbonyl}-piperazin-1-yl)-1-morpholin-4-yl-ethanone;

cis-2-(4-{4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-N,N-diethyl-isobutyramide;

cis-2-(4-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-phenyl)-N,N-diethyl-isobutyramide and

[2-(4-tert-Butyl-2-ethoxy-phenyl)-4,5-bis-(4-chloro-phenyl)-4,5-dihydro-imidazol-1-yl]-(4-dimethylamino-piperidin-1-yl)-methanone hydrochloride.

"Effective amount" means an amount that is effective to prevent, alleviate or ameliorate symptoms of disease or prolong the survival of the subject being treated.

"Halogen" means fluorine, chlorine, bromine or iodine.

"Hetero atom" means an atom selected from N, O and S.

"$IC_{50}$" refers to the concentration of a particular compound required to inhibit 50% of a specific measured activity. $IC_{50}$ can be measured, inter alia, as is described subsequently.

"Alkyl" denotes a straight-chained or branched saturated aliphatic hydrocarbon.

"Cycloalkyl" means a non-aromatic, partially or completely saturated monovalent cyclic hydrocarbon radical containing 3 to 8 atoms. Preferred examples of cycloalkyl groups are cyclopropyl, cyclobutyl, and cyclopentyl.

"Lower alkyl" groups denote C1-C6 alkyl groups and include methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl.

"Alkoxy" denotes —O-alkyl. "Lower alkoxy" denotes —O-lower alkyl.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted" means that the substitution can occur at one or more positions and, unless otherwise indicated, that the substituents at each substitution site are independently selected from the specified options.

"Therapeutically effective amount" means an amount of at least one designated compound, that significantly inhibits proliferation and/or prevents differentiation of a human tumor cell, including human tumor cell lines.

Compounds of the present invention as exemplified advantageously show IC50s from about 0.005 uM to about 20 uM.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention also provides pharmaceutical compositions comprising at least one compound of formula I, or a pharmaceutically acceptable salt or ester thereof, and a pharmaceutically acceptable carrier or excipient.

The compounds of the present invention can be prepared according to the following scheme 1.

Scheme I

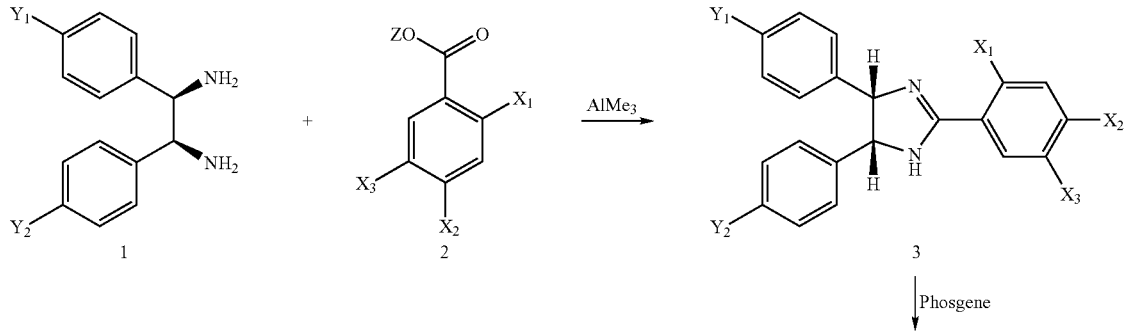

-continued

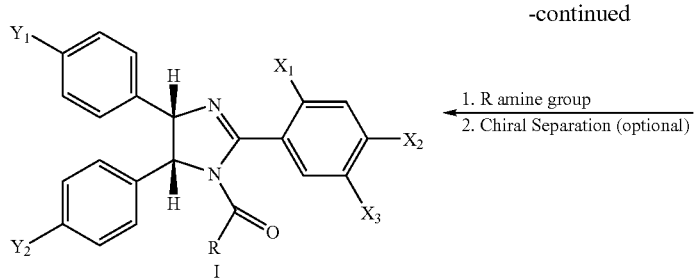
I

1. R amine group
2. Chiral Separation (optional)

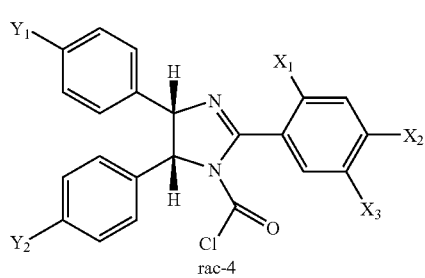
rac-4

R amine group

Chiral Separation (optional)

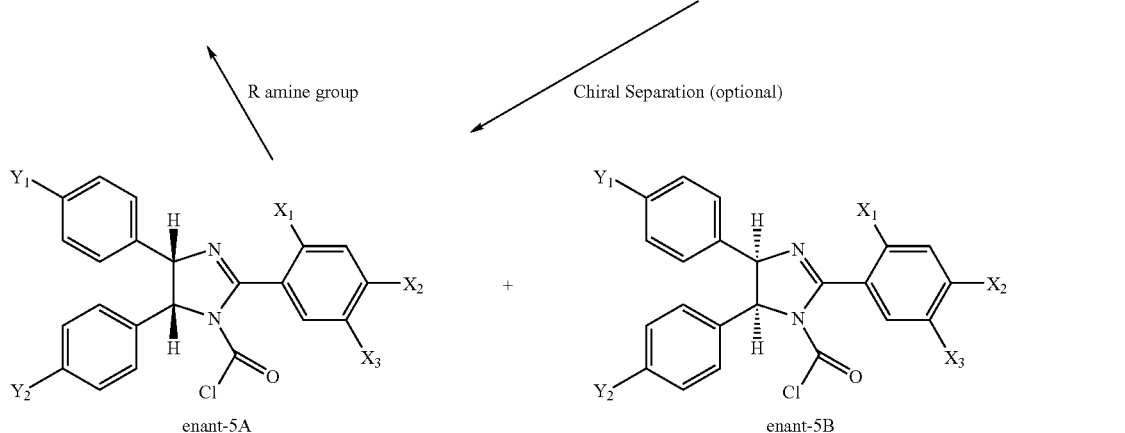
enant-5A       +       enant-5B

The synthesis commences with the coupling reaction of the benzoic acid ester 2 (Z=methyl, ethyl, etc.) with diamine 1 (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40) using trimethylaluminum as a catalyst in a solvent such as toluene with heating at reflux (Moormann, A. E. et al *J. Med. Chem.* 1990, 33, 614-626). Benzoic acid esters 2 are prepared using the procedures known in the art. Treatment of the cis-imidazoline 3 with phosgene in the presence of a base such as triethylamine gives the racemic carbamoyl chloride 4. Coupling of the racemic carbamoyl chloride 4 with appropriate R amine groups provides the compounds of the formula I as racemic mixtures. Many R amine groups are commercially available. If it is desired, R amine groups can be prepared using synthetic methods known in the art. Suitable processes for making these R amine groups are provided in the examples.

If it is desired to prepare the optically active compounds of formula I, the enantiomers of the carbamoyl chloride rac-4 can be separated using chiral chromatography. The chiral stationary phase R,R-Whelk-O1, available through Regis Technologies, can be used. Coupling of the desired enantiomer 5A with appropriate R amine groups provides the compounds of the formula I.

Also the optically active compounds of formula I can be obtained by chiral separation of the racemic mixtures of I. The chiral stationary phase Diacel ChiralPak OD or AD can be used.

The absolute stereochemistry of the preferred enantiomer of I is determined based on the crystal structure of its complex with the human MDM2 (Vassilev et al. *Science*, 2004, 303, 844-848).

The following examples and references are provided to aid the understanding of the present invention, the true scope of which is set forth in the appended claims.

Example 1

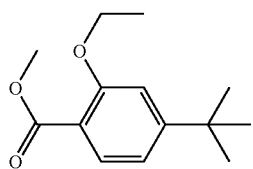

a) Methyl 4-tert-butyl-2-ethoxybenzoate

A solution of 3-tert-butylphenol (100 g, 665.7 mmol, TCI) and potassium hydroxide (37.35 g, 665.7 mmol) in 260 mL of water was added to a vigorously stirred solution of iodine (202.8 g, 798.8 mmol) and potassium hydroxide (89.95 g, 1598 mmol) in 1100 mL of water. The combined solution immediately turned white. It was stirred for 5 min. A small sample of the reaction mixture was removed, acidified and extracted with ethyl acetate. Thin layer chromatography (silica gel, 30% methylene chloride in hexane) showed the product (lower Rf) and some starting material. Methylene chloride (450 mL) was added, and sulfuric acid solution was added until a permanent brown color appeared (pH ~7). The layers were separated, and the organic layer was washed with water until it was neutral. The solvents were evaporated to dryness to give a reddish oil (162 g). The crude oil was purified by flash column chromatography (silica gel, eluting with hexane, 5-10% methylene chloride in hexane) to give 5-tert-butyl-2-iodo-phenol (132.7 g) as an amber oil (solidified upon standing).

The mixture of 5-tert-butyl-2-iodo-phenol (132.7 g, 480.6 mmol), potassium carbonate (265.7 g, 1923 mmol) and ethyl iodide (76.9 mL, 961.3 mmol) in ethanol (1.125 mL) was heated at reflux overnight. Upon cooling to room temperature, the reaction mixture was diluted with diethyl ether. The white solids were filtered off, and the filtrate was concentrated in vacuo to give 4-tert-butyl-2-ethoxy-1-iodo-benzene (144.7 g) as pale yellow oil.

In a 2 L pressure reaction flask was placed 4-tert-butyl-2-ethoxy-1-iodo-benzene (142 g, 466.9 mmol), dimethylformamide (275 mL), methanol (500 mL) and triethylamine (130 mL, 933.7 mmol). Argon was bubbled through the mixture for 1 h. Bis(triphenylphosphine)-palladium(II) chloride (19.69 g, 28.05 mmol) was added. The flask was evacuated then pressurized with carbon monoxide (40 psi) five times. The reaction was heated overnight at 65° C. under carbon monoxide pressure (40 psi). Upon cooling to room temperature, the reaction mixture was diluted with ethyl acetate (1400 mL) and washed with water (2×600 mL), brine (1×200 mL), and dried over anhydrous magnesium sulfate. The solids were filtered off, and the filtrate was concentrated to dryness to give dark oil (160 g). It was taken in ethyl acetate (160 mL), and hexane (1200 mL) was added while stirring vigorously. After the mixture was settled, the supernatant was removed. The same procedure was repeated two more times with ethyl acetate and hexane. The combined supernatant was treated with charcoal then filtered. The filtrate was concentrated in vacuo. It may be necessary to repeat the same procedure with ethyl acetate and hexane if there are still more solids present. The crude product was purified by flash chromatography (silica gel, eluting with 4% ethyl acetate in hexane) to give 93.5 g of methyl 4-tert-butyl-2-ethoxy-benzoate as a red oil.

b) Methyl 4-tert-butyl-2,5-diethoxybenzoate: prepared from 2-tert-butylhydroquinone in an analogous manner as described in example 1a.

Example 2

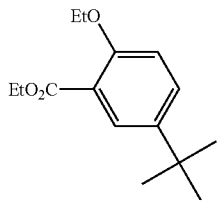

Ethyl 5-tert-butyl-2-ethoxybenzoate 5-tert-Butyl-2-hydroxy-benzaldehyde (1.4 g, 6.0 mmol, prepared according to Smith W. E. *J. Org. Chem.* 1972, 37, 3972-3973) was taken up in 30 mL of a 2M solution of 2-methyl-2-butene in tetrahydrofuran. t-Butanol (30 mL) was added. Sodium dihydrogenphosphate (2.6 g, 18.8 mmol) and sodium chlorite (1.4 g, 12.3 mmol) were then added as a solution in 12 mL of water. The reaction mixture was stirred at room temperature for 2 h. It was diluted with ethyl acetate and washed with 1N hydrochloric acid. The aqueous layers were extracted three times with ethyl acetate. The combined organic layers were washed with a saturated solution of $Na_2S_2O_3$, brine, and dried over anhydrous magnesium sulfate. The solids were filtered off, and the filtrate was concentrated to give 5-tert-butyl-2-hydroxy-benzoic acid (1.5 g, quant.), which was used in the next step without further purification.

Potassium carbonate (9.4 g, 68.0 mmol) and iodoethane (3.3 mL, 41.3 mmol) were added to a stirred solution of 5-tert-butyl-2-hydroxy-benzoic acid (1.3 g, 6.8 mmol) in 2-butanone (50 mL). The resulting mixture was heated at 80° C. (oil bath) for 16 h and then allowed to cool. The solution was concentrated and redisolved in methylene chloride. The organic phase was washed with water, brine, and dried over anhydrous magnesium sulfate. The solids were filtered off, and the filtrate was concentrated. Purification of the crude residue by flash chromatography (silica gel, eluting with 5-10% ethyl acetate in hexanes) gave ethyl 5-tert-butyl-2-ethoxy-benzoate (1.2 g, 81%) as a yellow oil.

Example 3

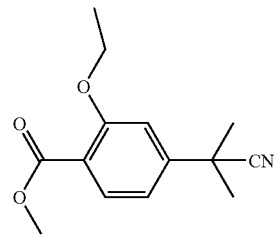

Methyl 4-(cyano-dimethylmethyl)-2-ethoxy-benzoate 2-(3-Ethoxy-phenyl)-2-methyl-propionitrile was prepared using a procedure adapted from literature (Organic Syntheses, Vol. 79, pp. 209-215). To a solution of 1-ethoxy-3-fluoro benzene (3.0 g, 19.4 mmol) in 25 mL of toluene was added solid potassium bis(trimethylsilyl)amide (5.84 g, 29.2 mmol, 1.5 eq) followed by isobutyronitrile (7.08 mL, 77.8 mmol, 4 eq). The reaction mixture was stirred at 100° C. for 12 hr. It was diluted with 75 mL of ethyl acetate and 75 mL of 1N aqueous hydrochloric acid. The layers were separated, and the aqueous layer was extracted with ethyl acetate. The combined organic layers were washed with water (1×50 mL), brine (1×50 mL), and dried over anhydrous magnesium sulfate. The solids were filtered off, and the filtrate was concentrated in vacuo. The residue was dissolved in 5 mL of methylene chloride and applied to a 40 g silica gel cartridge. The product was eluted using a gradient of ethyl acetate in hexanes to yield 2.96 g (15.6 mmol, 80%) of pure 2-(3-ethoxy-phenyl)-2-methyl-propionitrile. LR-MS: 190.12 [(M+H)+]

2-(3-Ethoxy-phenyl)-2-methyl-propionitrile (2.96 grams, 15.65 mmol) was dissolved in a freshly prepared acetic acid solution of iodine monochloride (20 mL of a 1.54 M iodine monochloride solution in acetic acid, 30.8 mmol). The reaction was slightly exothermic. The reaction mixture was allowed to stand at room temperature for 3 d. The reaction mixture was concentrated, and the residue was partitioned between ethyl acetate and water. The organic layer was washed with 10% sodium carbonate (1×), brine (1×), and dried (anhydrous magnesium sulfate). The solids were filtered off, and the filtrate was concentrated to dryness. The residue was purified by flash chromatography 110 g of silica gel, eluting with a gradient of ethyl acetate in hexanes) to give 2-(3-ethoxy-4-iodo-phenyl)-2-methyl-propionitrile (2.53 g, 51%). LR-MS: 316.21 [(M+H)+]

Nitrogen gas was bubbled through a solution of (3-ethoxy-4-iodo-phenyl)-2-methyl-propionitrile (2.53 grams, 8 mmol) and diisopropylethylamine (2.09 mL, 12 mmol) in methanol (10 mL). Using a balloon filled with carbon monoxide gas (CO) and equipped with a needle, CO was bubbled through the mixture until it was saturated. Palladium (II) acetate (100 mg) was added, and the mixture was stirred under an atmosphere of CO at 60° C. for 6 d. The reaction mixture was filtered and concentrated. The residue was partitioned between methylene chloride and 1.0M hydrochloric acid. The organic layer was dried (anhydrous magnesium sulfate), filtered. The residue was purified by flash chromatography (120 g of silica gel, eluting with a gradient of ethyl acetate in hexanes) to give methyl 4-(cyano-dimethylmethyl)-2-ethoxy-benzoate (1.09 g, 55%). LR-MS: 248.19 [(M+H)$^+$]

Example 4

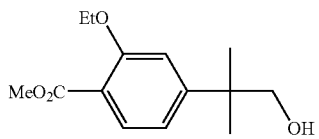

Methyl 2-ethoxy-4-(2-hydroxy-1,1-dimethylethyl)benzoate

Potassium carbonate (65.3 g, 473 mmol) and iodoethane (25.5 mL, 324 mmol) were added to a stirred solution of 3-hydroxyphenylacetic acid (12.0 g, 79 mmol) in 2-butanone (125 mL). The resulting mixture was heated in an oil bath (80° C.) for 16 h and then allowed to cool. The mixture was concentrated and methylene chloride was added. The organic layer was washed with water, brine, and dried over anhydrous magnesium sulfate. The solids were filtered off, and the filtrate was concentrated to give ethyl 3-ethoxyphenylacetate (12.7 g, 78%) as a clear oil.

Potassium hydride (32 g, 240 mmol, 30% in mineral oil) was washed twice with hexanes and dried. To this was added dropwise with ice-cooled tetrahydrofuran (60 mL), followed by a solution of ethyl 3-ethoxyphenylacetate (12.7 g, 61 mmol) in tetrahydrofuran (20 mL) and finally methyl iodide (8.4 mL, 134 mmol). The reaction mixture was stirred at room temperature overnight and partitioned between aqueous sodium bicarbonate and methylene chloride. The organic layer was dried over anhydrous magnesium sulfate and concentrated to give ethyl dimethyl-3-ethoxyphenylacetate (13.6 g, 94%) as a pale yellow oil.

To a cooled solution (5° C.) of ethyl dimethyl-3-ethoxyphenylacetate (5.0 g, 21.1 mmol) in acetic acid (40 mL) was added dropwise a solution of iodine monochloride (5.0 g, 30.9 mmol) in acetic acid. The reaction was stirred at room temperature for 18 h and diluted with water and extracted with methylene chloride. The combined organic layers were washed with aqueous sodium thiosulfate, aqueous sodium bicarbonate and brine. The solution was dried over anhydrous magnesium sulfate, filtered and concentrated to give ethyl dimethyl-(3-ethoxy-4-iodophenyl)acetate (6.25 g, 82%) as a yellow oil.

Boran dimethylsulfide (33 mL, 66 mmol, 2M in tetrahydrofuran) was added to a solution of ethyl dimethyl-(3-ethoxy-4-iodophenyl)acetate (4.83 g, 13.3 mmol) in ethyl ether (40 mL). The reaction was stirred at room temperature for 3 d and stirred for an additional hour with 2-propanol (10 mL) to quench the excess borane. The solution was partitioned between aqueous sodium bicarbonate and methylene chloride. The organic layer was washed with brine, dried over anhydrous magnesium sulfate and concentrated to give 2-ethoxy-4-(2-hydroxy-1,1-dimethylethyl)iodobenzene (4.23 g, 99%) as a yellow oil.

Triethylamine (3.5 mL, 25.1 mmol) was added to a solution 2-ethoxy-4-(2-hydroxy-1,1-dimethylethyl)iodobenzene (4.0 g, 12.5 mmol) in methanol (20 mL) under an atmosphere of nitrogen. The reaction was purged twice with carbon monoxide, and palladium (II) acetate (0.2 g, 0.9 mmol) was added. The reaction was stirred at 80° C. for 18 h under a positive pressure of carbon monoxide. The reaction was diluted with ether, washed with 10% hydrochloric acid, aqueous sodium bicarbonate, brine, dried over anhydrous magnesium sulfate and concentrated. Purification of the crude residue by flash chromatography over silica gel using 20-75% ethyl acetate in hexanes gave methyl 2-ethoxy-4-(2-hydroxy-1,1-dimethylethyl)benzoate (1.5 g, 48%) as a yellow oil and 0.91 g of unreacted 2-ethoxy-4-(2-hydroxy-1,1-dimethylethyl)iodobenzene.

Example 5

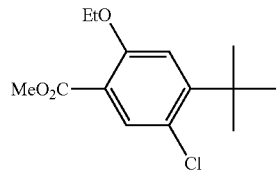

Ethyl 4-tert-butyl-5-chloro-2-ethoxybenzoate

Potassium carbonate (8.0 g, 58.0 mmol) and iodoethane (3.0 mL, 37.7 mmol) were added to a stirred solution of 5-t-butyl-4-chloro-2-iodophenol (2.4 g, 8.1 mmol; prepared according to Fukata et al. *Bull. Chem. Soc. Jpn.* 1994, 67, 592-594) in 2-butanone (50 mL). The resulting mixture was heated in an oil bath (80° C.) for 16 h and then allowed to cool. The solution was concentrated and redissolved in methylene chloride. The organic layer was washed with water, brine, dried over anhydrous magnesium sulfate and concentrated to give 4-tert-butyl-5-chloro-2-ethoxy-1-iodobenzene (2.2 g, 85%) as a yellow oil.

To a degassed solution of 4-tert-butyl-5-chloro-2-ethoxy-1-iodobenzene (2.2 g, 6.4 mmol), sodium methoxide (0.52 g, 9.6 mmol) and dichlorobistriphenylphosphinepalladium (0.25 g, 0.4 mmol) in dioxane (20 mL) was added methylformate (1.2 mL, 19.4 mmol). The resulting mixture was heated in an oil bath (60° C.) for 18 h and then allowed to cool. The solution was diluted with dioxane and filtered through a plug of Celite and concentrated. Purification of the crude residue by flash chromatography over silica gel using 5-20% ethyl acetate in hexanes gave ethyl 4-tert-butyl-5-chloro-2-ethoxybenzoate (1.39 g, 80%) as a clear oil.

Example 6

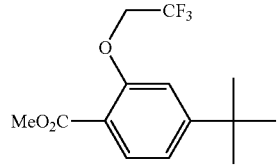

Methyl 4-tert-butyl-2-(2,2,2-trifluoroethoxy)benzoate

Potassium carbonate (3.8 g, 27.6 mmol) and 2,2,2-trifluoroethyl trifluoromethanesulfonate (2.4 g, 10.3 mmol) were added to a stirred solution of 4-t-butyl-2-iodophenol (1.9 g, 6.9 mmol, prepared according to the procedure as described in example 1a) in 2-butanone (30 mL). The resulting mixture was heated in an oil bath (60° C.) for 16 h and then allowed to cool. The solution was diluted with ethyl acetate and washed with water, brine, and dried over anhydrous magnesium sulfate. The solids were filtered off, and the filtrate was concentrated to give 4-tert-butyl-1-iodo-2-(2,2,2-trifluoro-ethoxy) benzene (2.4 g, 96%) as a yellow oil.

To a degassed solution of 4-tert-butyl-1-iodo-2-(2,2,2-trifluoro-ethoxy)benzene (2.5 g, 6.9 mmol), sodium methoxide (0.57 g, 10.4 mmol) and dichlorobistriphenylphosphinepalladium (0.25 g, 0.3 mmol) in dioxane (6 mL) was added methylformate (0.86 mL, 14.0 mmol). The resulting mixture was heated in an oil bath (60° C.) for 18 h and then allowed to cool. The solution was diluted with dioxane and filtered through a plug of Celite and concentrated. Purification of the crude residue by flash chromatography over silica gel using 5-15% ethyl acetate in hexane gave ethyl 4-tert-butyl-2-(2,2,2-trifluoroethoxy)benzoate (1.1 g, 55%) as a clear oil.

Example 7

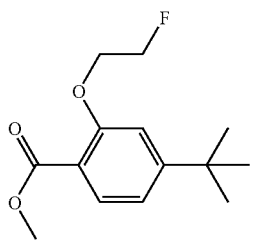

Methyl 4-tert-butyl-2-(2-fluoro-ethoxy)-benzoate: prepared from 4-t-butyl-2-iodophenol and 1-bromo-2-fluoro-ethane in an analogous manner as described in example 6.

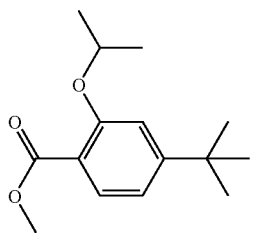

Methyl 4-tert-Butyl-2-isopropoxy-benzoate: prepared from 4-t-butyl-2-iodophenol and isopropyl iodide in an analogous manner as described in example 6.

Example 8

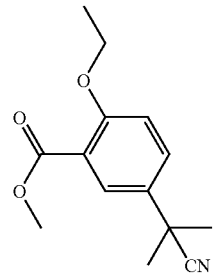

Methyl 5-(cyano-dimethylmethyl)-2-ethoxy-benzoate: prepared from 1-ethoxy-4-fluoro-benzene in an analogous manner as described in example 3.

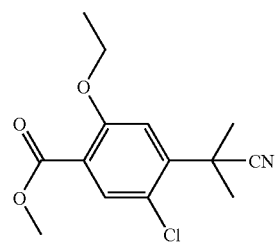

Methyl 5-(cyano-dimethylmethyl)-2-ethoxy-benzoate: prepared from 1-chloro-4-ethoxy-2-fluoro-benzene in an analogous manner as described in example 3.

Example 9

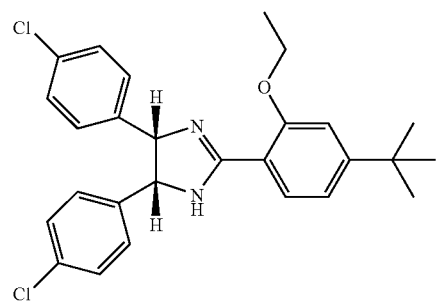

2-(4-tert-Butyl-2-ethoxy-phenyl)-4,5-bis-(4-chlorophenyl)-4,5-dihydro-1H-imidazole Trimethylaluminum (71.15 mL, 142.3 mmol, 2 M solution in toluene, Aldrich) was added to a flask via syringe and cooled to 0° C. A mixture of meso-1,2-bis-(4-chlorophenyl)-ethane-1,2-diamine (40 g, 142.3 mmol, prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40) in about 400-500 ml of toluene was added dropwise over a period of 30 min. After the addition was completed, the cooling bath was removed, and the mixture was stirred at room temperature for 15 min, at 50-60° C. for 30 min, and then 80-90° C. for 30 min. When the temperature was cooled back to 60° C., a solution of methyl 4-tert-butyl-2-ethoxy-benzoate (40 g, 142.3 mmol, example 1) in toluene (100 ml) was added. The reaction mixture was heated at reflux for 3 h. The progress of the reaction was monitored by thin layer chromatography (silica gel, eluting with ethyl acetate). The reaction mixture was then cooled in ice bath to 10° C., Rochelle salt solution (300 mL, 1 M) was added. The ice bath was removed, and the biphasic mixture was stirred vigorously for 30 min. Ethyl acetate (300 mL) was added and stirring was continued overnight. When the layers were separated, the organic layer was decanted off. More ethyl acetate (500 mL) and Rochelle salt solution (200 mL, 1 M) were added, and the mixture were transferred to a separatory funnel. The layers were separated. The combined organic extracts were washed with saturated solution of sodium bicarbonate (200 ml), brine (100 mL), and dried over anhydrous magnesium sulfate. The solids were filtered off, and the filtrate was concentrated in vacuo to give a yellow oil (69 g). The crude product was purified by a silica gel plug (600 g, eluting with 50% methylene chloride in hexane, methylene chloride, ethyl acetate, then 7.5% methanol in ethyl acetate) to give 2-(4-tert-butyl-2-ethoxy-phenyl)-4,5-bis-(4-chloro-phenyl)-4,5-dihydro-1H-imidazole (51.5 g). HR-MS (ES, m/z) calculated for $C_{27}H_{29}N_2OCl_2$ $[(M+H)^+]$ 467.1652, observed 467.1648.

Example 10

In an analogous manner as described in example 9, there were obtained:

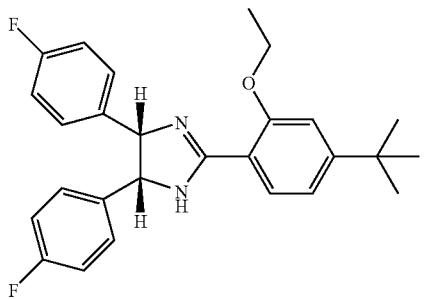

a) 2-(4-tert-Butyl-2-ethoxy-phenyl)-4,5-bis-(4-fluorophenyl)-4,5-dihydro-1H-imidazole: prepared from methyl 4-tert-butyl-2-ethoxy-benzoate (example 1a) and meso-1,2-bis-(4-fluorophenyl)-ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 435.4 $[(M+H)^+]$.

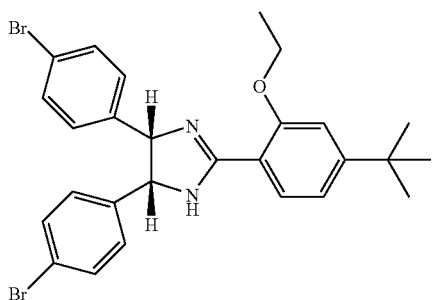

b) 4,5-Bis-(4-bromo-phenyl)-2-(4-tert-butyl-2-ethoxyphenyl)-4,5-dihydro-1H-imidazole: prepared from methyl 4-tert-butyl-2-ethoxy-benzoate (example 1a) and meso-1,2-bis-(4-bromophenyl)-ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 557.1 $[(M+H)^+]$.

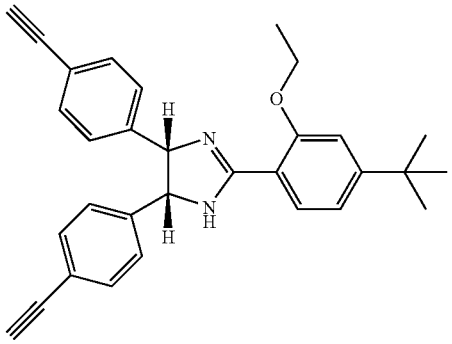

c) 2-(4-tert-Butyl-2-ethoxy-phenyl)-4,5-bis-(4-ethynylphenyl)-4,5-dihydro-1H-imidazole: prepared from methyl 4-tert-butyl-2-ethoxy-benzoate (example 1a) and meso-1,2-bis-(4-ethynyl phenyl)-ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 447.4 $[(M+H)^+]$.

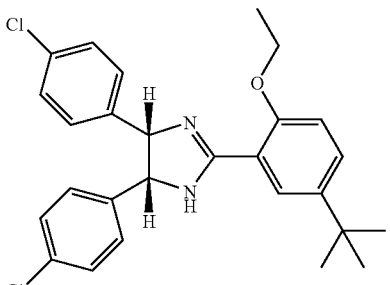

d) 2-(5-tert-Butyl-2-ethoxy-phenyl)-4,5-bis-(4-chlorophenyl)-4,5-dihydro-1H-imidazole: prepared from ethyl 5-tert-butyl-2-ethoxy-benzoate (example 2) and meso-1,2-bis-(4-chlorophenyl)-ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 467.3 $[(M+H)^+]$.

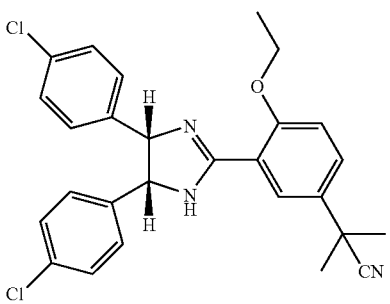

e) 2-{3-[4,5-Bis-(4-chloro-phenyl)-4,5-dihydro-1H-imidazol-2-yl]-4-ethoxy-phenyl}-2-methyl-propionitrile: prepared from methyl 5-(cyano-dimethyl-methyl)-2-ethoxybenzoate (example 8a) and meso-1,2-bis-(4-chlorophenyl)- ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 478.2 [(M+H)+].

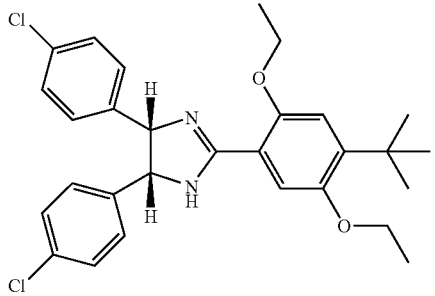

f) 2-(4-tert-Butyl-2,5-diethoxy-phenyl)-4,5-bis-(4-chloro-phenyl)-4,5-dihydro-1H-imidazole: prepared from methyl 4-tert-butyl-2,5-diethoxybenzoate (example 1b) and meso-1,2-bis-(4-chlorophenyl)-ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 511.3 [(M+H)+].

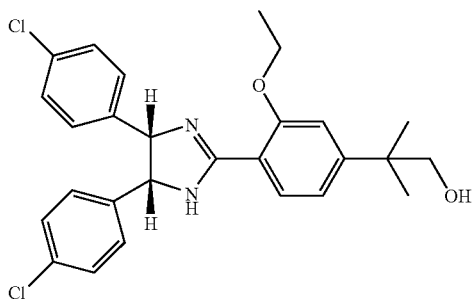

g) 2-{4-[4,5-Bis-(4-chloro-phenyl)-4,5-dihydro-1H-imidazol-2-yl]-3-ethoxy-phenyl}-2-methyl-propan-1-ol: prepared from methyl 2-ethoxy-4-(2-hydroxy-1,1-dimethyl-ethyl)benzoate (example 4) and meso-1,2-bis-(4-chlorophenyl)-ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 483.3 [(M+H)+].

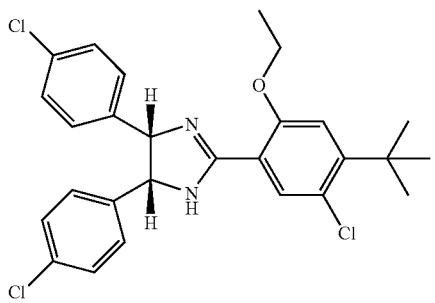

h) 2-(4-tert-Butyl-5-chloro-2-ethoxy-phenyl)-4,5-bis-(4-chloro-phenyl)-4,5-dihydro-1H-imidazole: prepared from methyl 4-tert-butyl-5-chloro-2-ethoxy-benzoate (example 5) and meso-1,2-bis-(4-chlorophenyl)-ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 501.4 [(M+H)+].

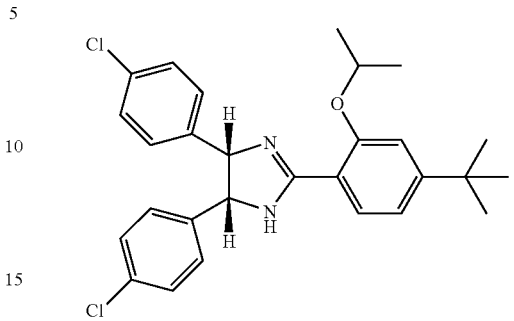

i) 2-(4-tert-Butyl-2-isopropoxy-phenyl)-4,5-bis-(4-chloro-phenyl)-4,5-dihydro-1H-imidazole: prepared from methyl 4-tert-butyl-2-isopropoxy-benzoate (example 7B) and meso-1,2-bis-(4-chlorophenyl)-ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 481.4 [(M+H)+].

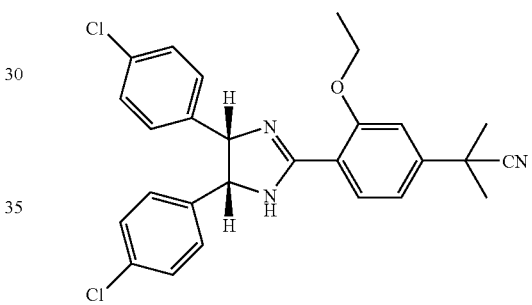

j) 2-{4-[4,5-Bis-(4-chloro-phenyl)-4,5-dihydro-1H-imidazol-2-yl]-3-ethoxy-phenyl}-2-methyl-propionitrile: prepared from methyl 4-(cyano-dimethyl-methyl)-2-ethoxy-benzoate (example 3) and meso-1,2-bis-(4-chlorophenyl)-ethane-1,2-diamine (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40). LR-MS: 478.2 [(M+H)+].

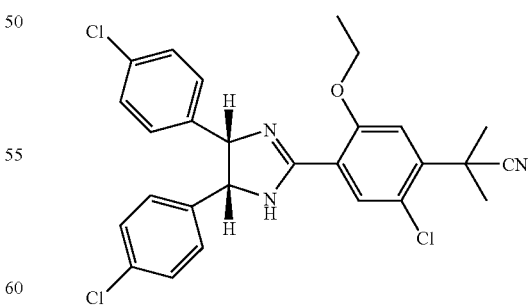

k) 2-{4-[(4,5-Bis-(4-chloro-phenyl)-4,5-dihydro-1H-imidazol-2-yl]-2-chloro-5-ethoxy-phenyl}-2-methyl-propionitrile: prepared from methyl 5-chloro-4-(cyano-dimethyl-methyl)-2-ethoxy-benzoate (example 8B) and meso-1,2-bis-(4-chlorophenyl)-ethane-1,2-diamine (prepared according to the procedure described by Jennerwein, M. et al. *Cancer Res.*

Clin. Oncol. 1988, 114, 347-58; Vogtle, F.; Goldschmitt, E. Chem. Ber. 1976, 109, 1-40). LR-MS: 512.2 [(M+H)+].

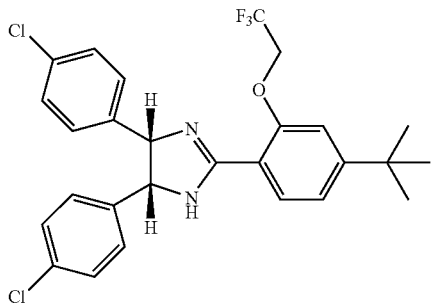

l) 2-[4-tert-Butyl-2-(2,2,2-trifluoro-ethoxy)-phenyl]-4,5-bis-(4-chloro-phenyl)-4,5-dihydro-1H-imidazole: prepared from ethyl 4-tert-butyl-2-(2,2,2-trifluoroethoxy)benzoate (example 6) and meso-1,2-bis-(4-chlorophenyl)-ethane-1,2-diamine (prepared according to the procedure described by Jennerwein, M. et al. Cancer Res. Clin. Oncol. 1988, 114, 347-58; Vogtle, F.; Goldschmitt, E. Chem. Ber. 1976, 109, 1-40). LR-MS: 521.4 [(M+H)+].

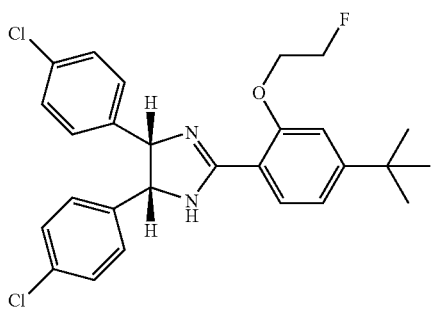

m) 2-[4-tert-Butyl-2-(2-fluoro-ethoxy)-phenyl]-4,5-bis-(4-chloro-phenyl)-4,5-dihydro-1H-imidazole: prepared from methyl 4-tert-butyl-2-(2-fluoro-ethoxy)-benzoate (example 7a) and meso-1,2-bis-(4-chlorophenyl)-ethane-1,2-diamine (prepared according to the procedure described by Jennerwein, M. et al. Cancer Res. Clin. Oncol. 1988, 114, 347-58; Vogtle, F.; Goldschmitt, E. Chem. Ber. 1976, 109, 1-40). LR-MS: 485.4 [(M+H)+].

Example 11

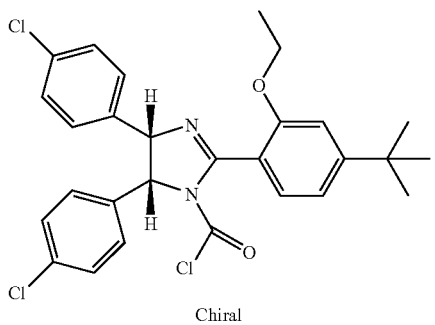

Chiral (4S,5R)-2-(4-tert-butyl-2-ethoxy-phenyl)-4,5-bis-(4-chloro-phenyl)-4,5-dihydro-imidazole-1-carbonyl chloride To a solution of 2-(4-tert-butyl-2-ethoxy-phenyl)-4,5-bis-(4-chloro-phenyl)-4,5-dihydro-1H-imidazole (19.7 g, 42.144 mmol) and triethylamine (17.6 mL, 126.432 mmol) in methylene chloride (200 mL) cooled to 0° C. was added phosgene (44.6 mL, 84.288 mmol, 20% solution in toluene, Fluka). The reaction mixture was stirred at 0° C. for 30 min then concentrated to dryness. The orange residue was taken in methylene chloride (100 mL), and the solution was filtered through a plug of silica gel (50 g). It was washed with methylene chloride (~600 mL). The filtrate was concentrated, and the residue was purified by flash chromatography (silica gel, eluting with 10% ethyl acetate in hexane) to give racemic-2-(4-tert-butyl-2-ethoxy-phenyl)-4,5-bis-(4-chloro-phenyl)-4,5-dihydro-imidazole-1-carbonyl chloride as white solids (12.650 g). The enantiomers of 2-(4-tert-butyl-2-ethoxy-phenyl)-4,5-bis-(4-chloro-phenyl)-4,5-dihydro-imidazole-1-carbonyl chloride were separated by chiral chromatography using a Waters Delta Prep 4000 and Modcol spring column (50 mm×70 cm) packed with R,R-Whelk-O1 spherical Kromasil silica gel (purchased from Regis Technologies). Eluent: 30% methylene chloride in hexane. Flowrate: 85 mL/min. Loading scale: 2.4-3.0 g. The first peak coming off the column is the desired (4S,5R)-2-(4-tert-butyl-2-ethoxy-phenyl)-4,5-bis-(4-chloro-phenyl)-4,5-dihydro-imidazole-1-carbonyl chloride.

Example 12

In an analogous manner as described in example 11, there were obtained:

a) (4S,5R)-2-(4-tert-Butyl-2-ethoxy-phenyl)-4,5-bis-(4-fluoro-phenyl)-4,5-dihydro-imidazole-1-carbonyl chloride: prepared from 2-(4-tert-butyl-2-ethoxy-phenyl)-4,5-bis-(4-fluoro-phenyl)-4,5-dihydro-1H-imidazole (example 10a).

b) (4S,5R)-4,5-Bis-(4-bromo-phenyl)-2-(4-tert-butyl-2-ethoxy-phenyl)-4,5-dihydro-imidazole-1-carbonyl chloride: prepared from 4,5-bis-(4-bromo-phenyl)-2-(4-tert-butyl-2-ethoxy-phenyl)-4,5-dihydro-1H-imidazole (example 10b).

c) (4S,5R)-2-(4-tert-Butyl-2-ethoxy-phenyl)-4,5-bis-(4-ethynyl-phenyl)-4,5-dihydro-imidazole-1-carbonyl chloride: prepared from 2-(4-tert-butyl-2-ethoxy-phenyl)-4,5-bis-(4-ethynyl-phenyl)-4,5-dihydro-1H-imidazole (example 10c).

d) (4S,5R)-2-(5-tert-Butyl-2-ethoxy-phenyl)-4,5-bis-(4-chloro-phenyl)-4,5-dihydro-imidazole-1-carbonyl chloride: prepared from 2-(5-tert-butyl-2-ethoxy-phenyl)-4,5-bis-(4-chloro-phenyl)-4,5-dihydro-1H-imidazole (example 10d).

e) (4S,5R)-4,5-Bis-(4-chloro-phenyl)-2-[5-(cyano-dimethyl-methyl)-2-ethoxy-phenyl]-4,5-dihydro-imidazole-1-carbonyl chloride: prepared from 2-{3-[4,5-bis-(4-chloro-phenyl)-4,5-dihydro-1H-imidazol-2-yl]-4-ethoxy-phenyl}-2-methyl-propionitrile (example 10e).

f) (4S,5R)-2-(4-tert-Butyl-2,5-diethoxy-phenyl)-4,5-bis-(4-chloro-phenyl)-4,5-dihydro-imidazole-1-carbonyl chloride: prepared from 2-(4-tert-butyl-2,5-diethoxy-phenyl)-4,5-bis-(4-chloro-phenyl)-4,5-dihydro-1H-imidazole (example 10f).

g) (4S,5R)-4,5-Bis-(4-chloro-phenyl)-2-[2-ethoxy-4-(2-hydroxy-1,1-dimethyl-ethyl)-phenyl]-4,5-dihydro-imidazole-1-carbonyl chloride: prepared from 2-{4-[4,5-bis-(4-chloro-phenyl)-4,5-dihydro-1H-imidazol-2-yl]-3-ethoxy-phenyl}-2-methyl-propan-1-ol (example 10g).

h) (4S,5R)-2-(4-tert-Butyl-5-chloro-2-ethoxy-phenyl)-4,5-bis-(4-chloro-phenyl)-4,5-dihydro-imidazole-1-carbonyl chloride: prepare from 2-(4-tert-butyl-5-chloro-2-ethoxy-phenyl)-4,5-bis-(4-chloro-phenyl)-4,5-dihydro-1H-imidazole (example 10h).

i) (4S,5R)-2-(4-tert-Butyl-2-isopropoxy-phenyl)-4,5-bis-(4-chloro-phenyl)-4,5-dihydro-imidazole-1-carbonyl chloride: prepared from 2-(4-tert-butyl-2-isopropoxy-phenyl)-4,5-bis-(4-chloro-phenyl)-4,5-dihydro-1H-imidazole (example 10i).

j) (4S,5R)-4,5-Bis-(4-chloro-phenyl)-2-[4-(cyano-dimethyl-methyl)-2-ethoxy-phenyl]-4,5-dihydro-imidazole-1-carbonyl chloride: prepared from 2-{4-[4,5-bis-(4-chloro-phenyl)-4,5-dihydro-1H-imidazol-2-yl]-3-ethoxy-phenyl}-2-methyl-propionitrile (example 10j).

k) (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride: prepared from 2-{4-[(4,5-bis-(4-chloro-phenyl)-4,5-dihydro-1H-imidazol-2-yl]-2-chloro-5-ethoxy-phenyl}-2-methyl-propionitrile (example 10k).

l) (4S,5R)-2-[4-tert-Butyl-2-(2,2,2-trifluoro-ethoxy)-phenyl]-4,5-bis-(4-chloro-phenyl)-4,5-dihydro-imidazole-1-carbonyl chloride: prepared from 2-[4-tert-butyl-2-(2,2,2-trifluoro-ethoxy)-phenyl]-4,5-bis-(4-chloro-phenyl)-4,5-dihydro-1H-imidazole (example 10l).

m) (4S,5R)-2-[4-tert-Butyl-2-(2-fluoro-ethoxy)-phenyl]-4,5-bis-(4-chloro-phenyl)-4,5-dihydro-imidazole-1-carbonyl chloride: prepared from 2-[4-tert-butyl-2-(2-fluoro-ethoxy)-phenyl]-4,5-bis-(4-chloro-phenyl)-4,5-dihydro-1H-imidazole (example 10m).

Example 13

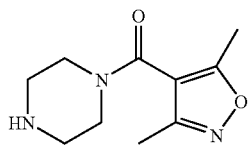

(3,5-Dimethyl-isoxazol-4-yl)-piperazin-1-yl-methanone

A solution of 1-tert-butyloxycarbonyl-piperazine (4.581 mmol, 0.9 eq) and diisopropylethylamine (5.09 mmol, 1.0 eq) in methylene chloride (5 mL) was added to a 40 mL vial. 3,5-Dimethyl-isoxazole-4-carbonyl chloride (5.09 mmol, 1.0 eq) was added to the vial and the reaction was shaken overnight at room temperature. When the reaction was complete, it was diluted with methylene chloride (5 mL) and washed with 4 mL of 1N HCl followed by 4 mL of 10% potassium carbonate. The organic layer was concentrated in vacuo. The crude residue was dissolved in 5 mL of dioxane and 5 mL of 4M hydrochloric acid in dioxane. The reaction mixture was shaken overnight at room temperature then centrifuged. The supernatant was removed and the remaining solid was shaken with hexane then centrifuged. The supernatant was removed, and the solids were collected and dried in vacuo to give (3,5-dimethyl-isoxazol-4-yl)-piperazin-1-yl-methanone. LR-MS: 210.2 [(M+H)+]

Example 14

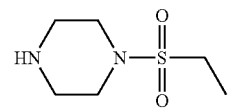

Ethanesulfonyl-piperazine: prepared from 1-tert-butyloxycarbonyl-piperazine and ethylsulfonyl chloride in an analogous manner as described in example 13.

Example 15

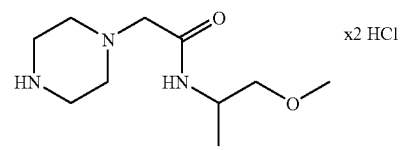

N-(2-Methoxy-1-methyl-ethyl)-2-piperazin-1-yl-acetamide dihydrochloride

Methoxy-1-methyl-ethylamine (15 mmol, 1.15 eq) and diisopropylethylamine (17 mmol, 1.3 eq) were diluted with methylene chloride to give a total volume of 8 mL. The amine solution was added in a portion-wise fashion via a syringe to a solution of chloroacetylchloride (13 mmol) in methylene chloride (10 mL) cooled to approximately −40° C. in a sealed 40 mL vial. The reaction mixture was stirred for 1 h at reduced temperature. The solution was then made acidic with 1N HCl and then diluted with 10 mL of methylene chloride. The vial was agitated and centrifuged. The organic layer was transferred to 40 ml, vials and concentrated in vacuo. The residue (1.69 g, 10.21 mmol) was diluted with 10 mL of dimethylformamide. Piperazine-1-carboxylic acid tert-butyl ester (8.67 mmol, 0.85 eq) and diisopropylethylamine (13.27 mmol, 1.3 eq) were added. The reaction mixture was shaken at 65° C. overnight and concentrated in vacuo. The crude residue was dissolved in 10 mL of dioxane and 10 mL of 4M hydrochloric acid in dioxane. The solution was shaken overnight at room temperature then centrifuged. The supernatant was removed, and the remaining solids were shaken with hexane then centrifuged. The supernatant was removed, and the solids was collected and dried in vacuo to give N-(2-methoxy-1-methylethyl)-2-piperazin-1-yl-acetamide dihydrochloride. LR-MS: 216.4 [(M+H)+]

Example 16

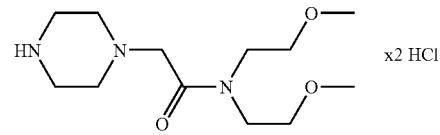

a) N,N-Bis-(2-methoxy-ethyl)-2-piperazin-1-yl-acetamide dihydrochloride: prepared from 1-tert-butyloxycarbonyl-piperazine, chloroacetylchloride and N,N-bis-(2-methoxy-ethyl)amine in an analogous manner as described in example 15.

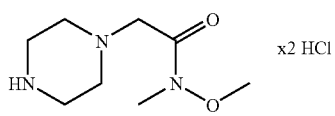

b) N-Methoxy-N-methyl-2-piperazin-1-yl-acetamide dihydrochloride: prepared from 1-tert-butyloxycarbonyl-piperazine, chloroacetylchloride and N-methoxy-N-methylamine in an analogous manner as described in example 15.

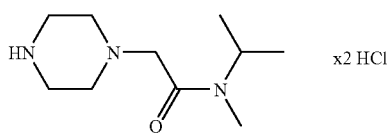

c) N-Isopropyl-N-methyl-2-piperazin-1-yl-acetamide dihydrochloride: prepared from 1-tert-butyloxycarbonyl-piperazine, chloroacetylchloride and N-isopropyl-N-methylamine in an analogous manner as described in example 15.

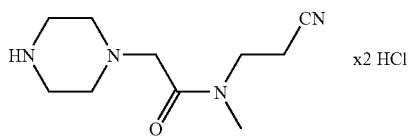

d) N-(2-Cyano-ethyl)-N-methyl-2-piperazin-1-yl-acetamide dihydrochloride: prepared from 1-tert-butyloxycarbonyl-piperazine, chloroacetylchloride and N-(2-cyanoethyl)-N-methylamine in an analogous manner as described in example 15.

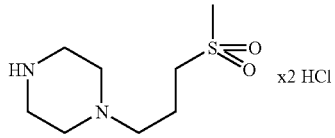

e) 1-(3-Methanesulfonyl-propyl)-piperazine dihydrochloride: prepared from 1-tert-butyloxycarbonyl-piperazine and methanesulfonic acid 3-methanesulfonyl-propyl ester (prepared according to Baerlocher, F. J. et al. *Aust. J. Chem.* 1999, 52, 167-172) in an analogous manner as described in example 15.

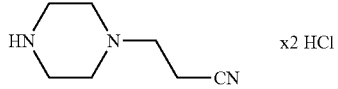

f) 3-piperazin-1-yl-propionitrile dihydrochloride: prepared from 1-tert-butyloxycarbonyl-piperazine and 3-bromopropionitrile in an analogous manner as described in example 15.

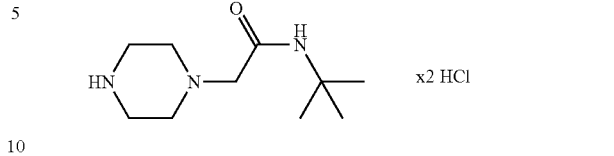

g) N-tert-Butyl-2-piperazin-1-yl-acetamide dihydrochloride: prepared from 1-tert-butyloxycarbonyl-piperazine, chloroacetylchloride and N-tert-butylamine in an analogous manner as described in example 15.

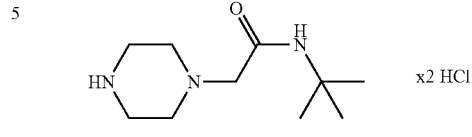

h) piperazin-1-yl-acetonitrile dihydrochloride: prepared from 1-tert-butyloxycarbonyl-piperazine and bromoacetonitrile in an analogous manner as described in example 15.

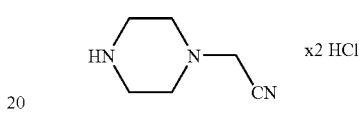

i) 1-(3,3,3-Trifluoro-propyl)-piperazine dihydrochloride: prepared from 1-tert-butyloxycarbonyl-piperazine and 3-bromo-1,1,1-trifluoropropane in an analogous manner as described in example 15.

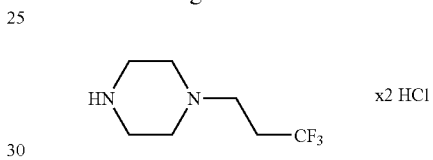

j) 3,3-Dimethyl-1-piperazin-1-yl-butan-2-one dihydrochloride: prepared from 1-tert-butyloxycarbonyl-piperazine and 1-chloro-3,3-dimethyl-butan-2-one (1-chloropinacolone) in an analogous manner as described in example 15.

Example 17

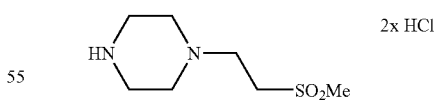

1-(2-Methanesulfonylethyl)piperazine dihydrochloride

Methyl vinyl sulfone (1.8 mL, 20.1 mmol) was added to a solution of 1-(tert-butyloxycarbonyl)piperazine (1.50 g, 8 mmol) in methanol (84 mL). The reaction mixture was stirred at room temperature for 4 h and concentrated to a white solid. Purification of the solid by flash column chromatography (silica gel, eluting with 1-5% methanol in methylene chloride) gave 1-tert-butyloxycarbonyl-4-(2-methanesulfonyl-ethyl)piperazine as a white solid (2.29 g, 95%).

Hydrochloric acid (42 mL, 168 mmol, 4 M in 1,4-dioxane) was added to a cooled solution of 1-tert-butyloxycarbonyl-4-(2-methanesulfonylethyl)piperazine (2.29 g, 7.8 mmol) in 1,4-dioxane (42 mL). The mixture was stirred at room temperature overnight then concentrated to give 1-(2-methanesulfonylethyl)piperazine dihydrochloride as a white solid (2.05 g).

Example 18

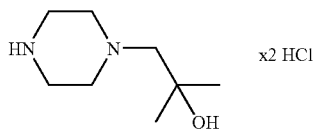

a) 2-Methyl-1-piperazin-1-yl-propan-2-ol dihydrochloride: prepared from 1-tert-butyloxycarbonyl-piperazine and 2,2-dimethyl-oxirane (1,2-epoxy-2-methylpropane) in an analogous manner as described in example 17.

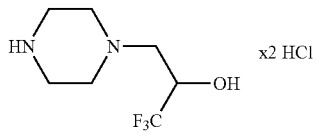

b) 1,1,1-Trifluoro-3-piperazin-1-yl-propan-2-ol dihydrochloride: prepared from 1-tert-butyloxycarbonyl-piperazine and 1,1,1-trifluoro-2,3-epoxypropane in an analogous manner as described in example 17.

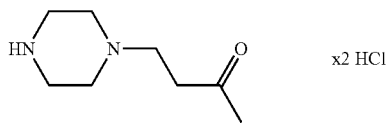

c) 4-Piperazin-1-yl-butan-2-one dihydrochloride: prepared from 1-tert-butyloxycarbonyl-piperazine and methyl vinyl ketone in an analogous manner as described in example 17.

Example 19

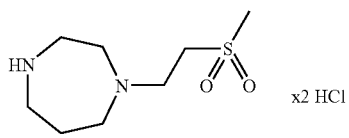

1-(2-Methanesulfonyl-ethyl)-[1,4]diazepane dihydrochloride was prepared from [1,4]diazepane-1-carboxylic acid tert-butyl ester and methyl vinyl sulfone using the same procedure as described in example 17.

Example 20

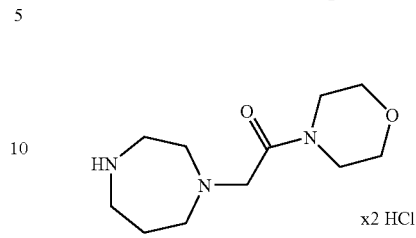

2-[1,4]Diazepan-1-yl-1-morpholin-4-yl-ethanone dihydrochloride: prepared from [1,4]diazepane-1-carboxylic acid tert-butyl ester, chloroacetylchloride and morpholine in an analogous manner as described in example 15.

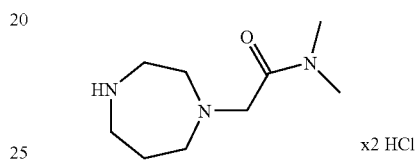

2-[1,4]Diazepan-1-yl-N,N-dimethyl-acetamide dihydrochloride: prepared from [1,4]diazepane-1-carboxylic acid tert-butyl ester, chloroacetylchloride and dimethylamine in an analogous manner as described in example 15.

Example 21

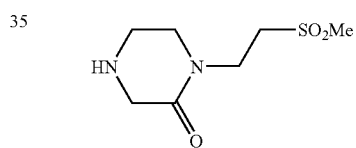

1-(2-Methanosulfonylethyl)-piperazine-2-one

Methyl vinyl sulfone (0.42 mL, 4.8 mmol) was added dropwise to a cooled solution of N-tert-butyloxycarbonyl-1,2-ethylenediamine hydrochloride (1.00 g, 5.1 mmol) and triethylamine (1.4 mL, 10.7 mmol) in methanol (20 mL). The reaction was stirred at room temperature for 18 h and concentrated. Purification of the crude residue by chromatography over silica gel using 0-5% methanol in methylene chloride gave 2-(N-tert-butyloxycarbonyl-2-aminoethylamino) ethyl methyl sulfone (1.05 g, 77%).

Chloroacetyl chloride (0.47 mL, 6.0 mmol) was added dropwise to a cooled solution 2-(N-tert-butyloxycarbonyl-2-aminoethylamino)ethyl methyl sulfone (1.05 g, 4.0 mmol) and triethylamine (1.1 mL, 8.0 mmol) in methylene chloride (50 mL). The reaction was stirred at room temperature for 2 h. The reaction was partitioned between aqueous sodium bicarbonate and methylene chloride. The organic phase was washed with brine, dried over anhydrous magnesium sulfate and concentrated. Purification of the crude residue by chromatography over silica gel using 0-10% methanol in methylene chloride gave {2-[(2-chloro-acetyl)-(2-methanesulfonyl-ethyl)-amino]-ethyl}-carbamic acid tert-butyl ester (1.20 g, 89%).

To a cooled solution of {2-[(2-chloro-acetyl)-(2-methanesulfonyl-ethyl)-amino]-ethyl}-carbamic acid tert-butyl ester (1.20 g, 3.5 mmol) in methylene chloride (20 mL) was added trifluoroacetic acid (5.0 mL), and the reaction was stirred at room temperature for 2 h and concentrated. The residue was dissolved in acetonitrile and triethylamine (1.5 mL, 10.8 mmol) was added. The reaction was stirred at room temperature for 18 h and concentrated. Purification of the crude residue by chromatography over silica gel using 0-20% methanol in methylene chloride gave 1-(2-methanosulfonyl-ethyl)-piperazine-2-one (0.36 g, 49%). LR-MS: 206.9 [(M+H)$^+$]

Example 22

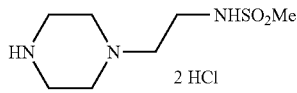

N-(2-methanosulfonylethyl)-piperazine dihydrochloride

Methanesulfonyl chloride (0.7 mL, 9.0 mmol) was added to a cooled solution of 4-(2-amino-ethyl)-piperazine-1-carboxylic acid tert-butyl ester (1.33 g, 5.8 mmol) in pyridine (25.0 mL). The reaction was stirred for 12 h and partitioned between partitioned between aqueous sodium bicarbonate and methylene chloride. The organic phase was washed with 1M hydrochloric acid, aqueous sodium bicarbonate, brine, dried over anhydrous magnesium sulfate and concentrated. Purification of the crude residue by chromatography over silica gel using 0-5% methanol in methylene chloride gave 4-(2-methanesulfonylamino-ethyl)-piperazine-1-carboxylic acid tert-butyl ester (0.70 g, 70%).

To a cooled solution of 4-(2-methanesulfonylamino-ethyl)-piperazine-1-carboxylic acid tert-butyl ester (0.64 g, 0.2 mmol) in dioxane (20 mL) was added hydrochloric acid (4M in dioxane, 10 mL) and the reaction was stirred at room temperature for 12 h and concentrated to give N-(2-methanosulfonylethyl)-piperazine dihydrochloride as a white solid (0.55 g, 95%).

Example 23

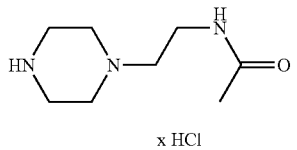

N-(2-piperazin-1-yl-ethyl)-acetamide hydrochloride was prepared from 4-(2-amino-ethyl)-piperazine-1-carboxylic acid tert-butyl ester and acetyl chloride in an analogous manner as described in example 22.

Example 24

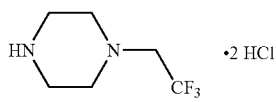

1-(2,2,2-Trifluoroethyl)piperazine dihydrochloride tert-Butyl-1-piperazinecarboxylate (1.00 g, 5.37 mmol) and pyridine (0.868 mL, 10.7 mmol) were combined in methylene chloride (27 mL) and cooled to 0° C. Trifluoroacetic anhydride (0.910 mL, 6.44 mmol) was then added and the reaction mixture was allowed to warm to ambient temperature and stirred 1 h. The reaction mixture was then diluted with ethyl acetate (150 mL) and washed with aqueous potassium hydrogen sulfate (2×50 mL), saturated aqueous sodium bicarbonate (50 mL) and brine (50 mL), then dried over sodium sulfate and evaporated to yield tert-butyl 4-(2,2,2-trifluoroacetyl)piperazine-1-carboxylate (1.50 g, 99%) as an oil which solidified over time.

tert-Butyl 4-(2,2,2-trifluoroacetyl)piperazine-1-carboxylate (0.908 g, 3.22 mmol) was added to a solution of borane-tetrahydrofuran complex (8 mmol) in tetrahydrofuran (24 mL) and the reaction mixture was heated at reflux for 2 h. After cooling, 2 N hydrochloric acid (4 mL) was carefully added and the reaction mixture was stirred until gas evolution ceased and then diluted with ethyl acetate (200 mL). Aqueous sodium hydroxide (0.2 M, 75 mL) was then added and the phases were separated. The organic layer was dried over sodium sulfate and evaporated. The residue was purified by column chromatography (eluting with 20% ethyl acetate in hexanes) to give tert-butyl 4-(2,2,2-trifluoroethyl)piperazine-1-carboxylate (0.627 g, 73%) as a white solid.

A solution of hydrochloric acid (4.0 M, 10 mL) in dioxane was added to a solution of tert-butyl 4-(2,2,2-trifluoroethyl)piperazine-1-carboxylate (0.736 g, 2.74 mmol) in dioxane (5 mL). The reaction mixture was stirred until analysis by thin layer chromatography indicated completion of reaction (approx. 3 h). The volatiles were evaporated and the residue was dried under vacuum to yield 1-(2,2,2-trifluoroethyl)piperazine dihydrochloride (0.631 g, 95%) as a white solid.

Example 25

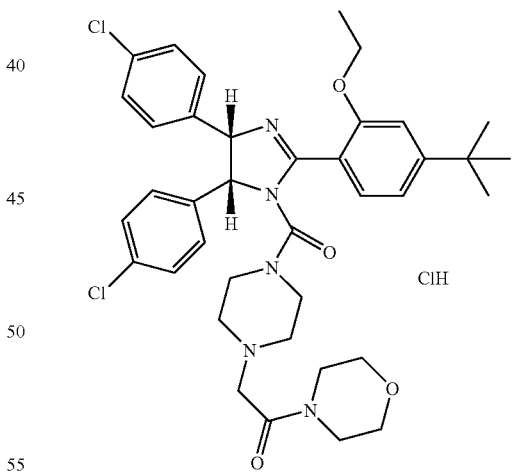

2-{4-[(4S,5R)-2-(4-tert-butyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride To a solution of (4S,5R)-2-(4-tert-butyl-2-ethoxy-phenyl)-4,5-bis-(4-chloro-phenyl)-4,5-dihydro-imidazole-1-carbonyl chloride (7.967 g, 15.03 mmol, example 11) in methylene chloride (60 mL) cooled to 0° C. were added triethylamine (4.19 mL) and 1-morpholin-4-yl-2-piperazin-1-yl-ethanone (3.366 g, 15.78 mmol, Oakwood Products), respectively. The ice bath was removed, and the reaction mixture was stirred at room temperature for 30 min. The reaction was monitored by thin layer chromatography (silica gel, 20% ethyl acetate in hexane). The reaction mixture was concentrated to dryness, and the crude residue was purified by flash column chromatography (silica gel, eluting with 0.1% triethylamine in ethyl acetate) to give 2-{4-[(4S,5R)-2-(4-tert-butyl-2-ethoxy-phenyl)-4,5-bis-(4-chloro-phenyl)-4,5-dihydro-imidazole-1-carbonyl]-piperazin-1-yl}-1-morpholin-4-yl-ethanone as white foam. The white foam was taken in 100 ml of ethyl acetate then filtered. Hydrogen chloride (18.04 mL, 1 M solution in diethyl ether) was added dropwise to the filtrate. The white solids formed were filtered off and dried in vacuo to give 2-{4-[(4S,5R)-2-(4-tert-butyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride (9.3 g). HR-MS (ES, m/z) calculated for $C_{38}H_{46}N_5O_4Cl_2$ [(M+H)$^+$] 706.2922, observed 706.2917.

Example 26

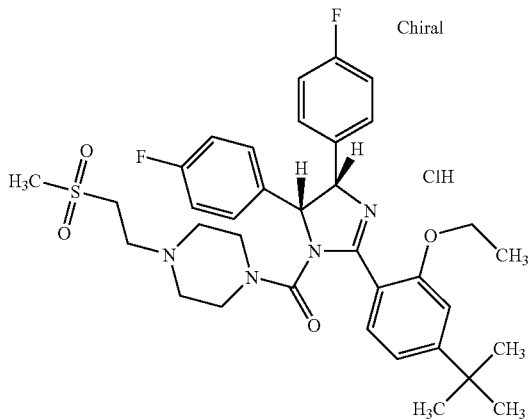

[(4S,5R)-2-(4-tert-Butyl-2-ethoxy-phenyl)-4,5-bis-(4-fluoro-phenyl)-4,5-dihydro-imidazol-1-yl]-[4-(2-methanesulfonyl-ethyl)-piperazin-1-yl]-methanone hydrochloride was prepared from (4S,5R)-2-(4-tert-butyl-2-ethoxy-phenyl)-4,5-bis-(4-fluoro-phenyl)-4,5-dihydro-imidazole-1-carbonyl chloride (example 12a) and 1-(2-methanesulfonyl-ethyl)piperazine dihydrochloride (example 17) in an analogous manner as described in example 25. LR-MS: 653.4 [(M+H)$^+$]

Example 27

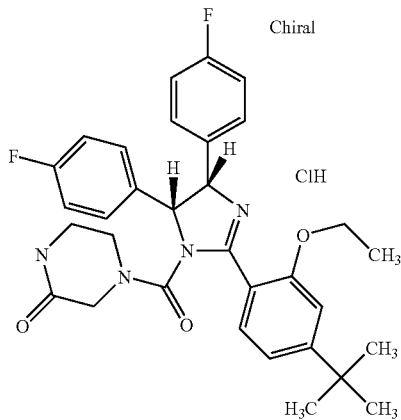

4-[(4S,5R)-2-(4-tert-Butyl-2-ethoxy-phenyl)-4,5-bis-(4-fluoro-phenyl)-4,5-dihydro-imidazole-1-carbonyl]-piperazin-2-one hydrochloride was prepared from (4S,5R)-2-(4-tert-butyl-2-ethoxy-phenyl)-4,5-bis-(4-fluoro-phenyl)-4,5-dihydro-imidazole-1-carbonyl chloride (example 12a) and 2-piperazinone (Avocado Organics) in an analogous manner as described in example 25. LR-MS: 561.4 [(M+H)$^+$]

Example 28

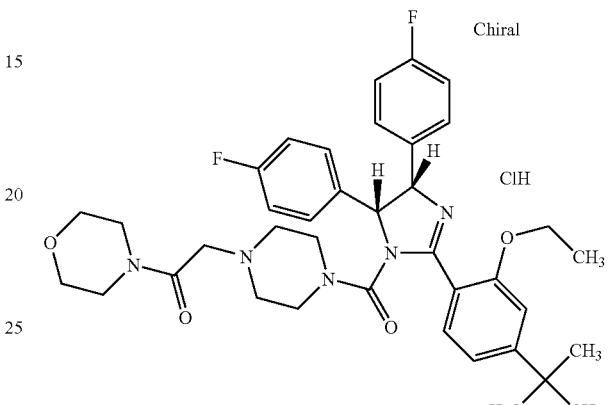

2-{4-[(4S,5R)-2-(4-tert-Butyl-2-ethoxy-phenyl)-4,5-bis-(4-fluoro-phenyl)-4,5-dihydro-imidazole-1-carbonyl]-piperazin-1-yl}-1-morpholin-4-yl-ethanone hydrochloride was prepared from (4S,5R)-2-(4-tert-butyl-2-ethoxy-phenyl)-4,5-bis-(4-fluoro-phenyl)-4,5-dihydro-imidazole-1-carbonyl chloride (example 12a) and 1-morpholin-4-yl-2-piperazin-1-yl-ethanone (Oakwood Products) in an analogous manner as described in example 25. LR-MS: 674.5 [(M+H)$^+$]

Example 29

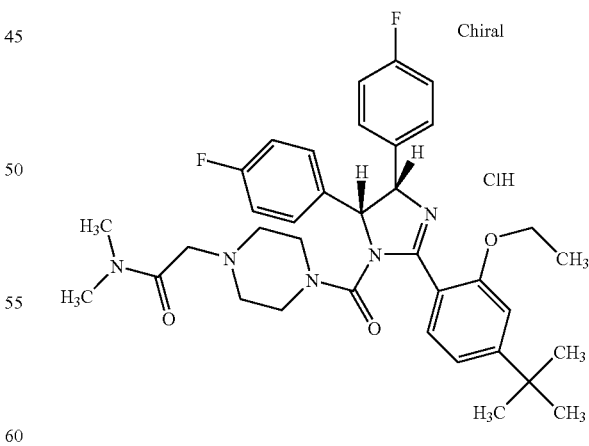

2-{4-[(4S,5R)-2-(4-tert-Butyl-2-ethoxy-phenyl)-4,5-bis-(4-fluoro-phenyl)-4,5-dihydro-imidazole-1-carbonyl]-piperazin-1-yl}-N,N-dimethyl-acetamide hydrochloride was prepared from (4S,5R)-2-(4-tert-butyl-2-ethoxy-phenyl)-4,5-bis-(4-fluoro-phenyl)-4,5-dihydro-imidazole-1-carbonyl chloride (example 12a) and N,N-dimethyl-2-piperazin-1-ylacetamide (Oakwood Products) in an analogous manner as described in example 25. LR-MS: 632.8 [(M+H)⁺]

Example 30

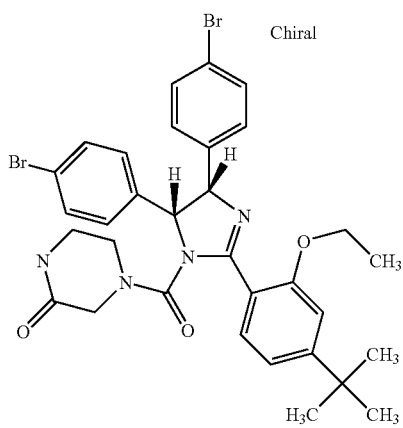

4-[(4S,5R)-4,5-Bis-(4-bromo-phenyl)-2-(4-tert-butyl-2-ethoxy-phenyl)-4,5-dihydro-imidazole-1-carbonyl]-piperazin-2-one was prepared from (4S,5R)-4,5-bis-(4-bromo-phenyl)-2-(4-tert-butyl-2-ethoxy-phenyl)-4,5-dihydro-imidazole-1-carbonyl chloride (example 12b) and 2-piperazinone (Avocado Organics) in an analogous manner as described in example 25. LR-MS: 681.3 [(M+H)⁺]

Example 31

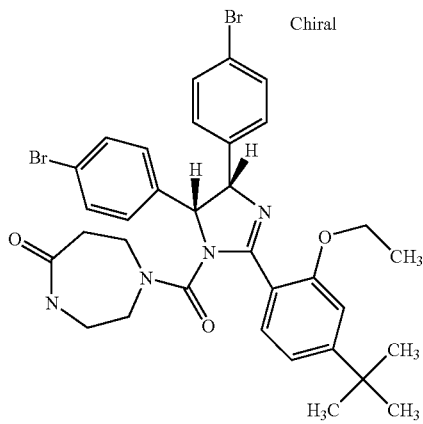

1-[(4S,5R)-4,5-Bis-(4-bromo-phenyl)-2-(4-tert-butyl-2-ethoxy-phenyl)-4,5-dihydro-imidazole-1-carbonyl]-[1,4]diazepan-5-one was prepared from (4S,5R)-4,5-bis-(4-bromo-phenyl)-2-(4-tert-butyl-2-ethoxy-phenyl)-4,5-dihydro-imidazole-1-carbonyl chloride (example 12b) and [1,4]diazepan-5-one (Oakwood Products) in an analogous manner as described in example 25. LR-MS: 695.3 [(M+H)⁺]

Example 32

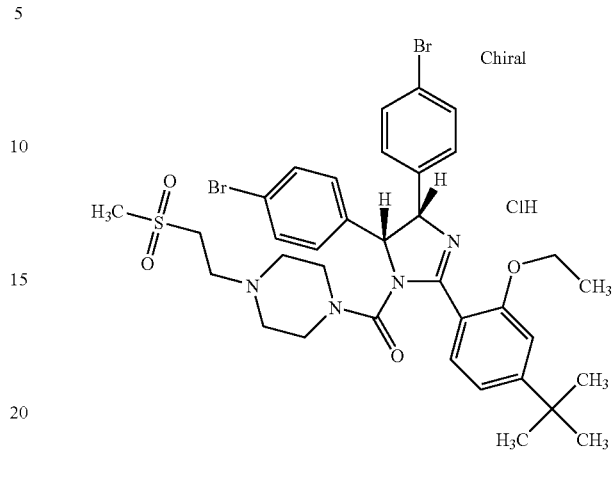

[(4S,5R)-4,5-Bis-(4-bromo-phenyl)-2-(4-tert-butyl-2-ethoxy-phenyl)-4,5-dihydro-imidazol-1-yl]-[4-(2-methanesulfonyl-ethyl)-piperazin-1-yl]-methanone hydrochloride was prepared from (4S,5R)-4,5-bis-(4-bromo-phenyl)-2-(4-tert-butyl-2-ethoxy-phenyl)-4,5-dihydro-imidazole-1-carbonyl chloride (example 12b) and 1-(2-methanesulfonylethyl)piperazine dihydrochloride (example 17) in an analogous manner as described in example 25. LR-MS: 773.3 [(M+H)⁺]

Example 33

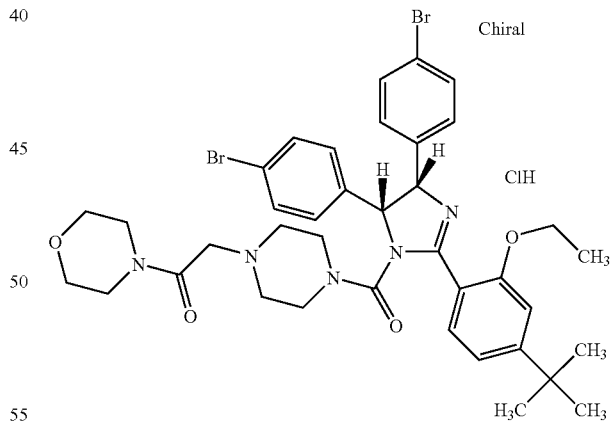

2-{4-[(4S,5R)-4,5-Bis-(4-bromo-phenyl)-2-(4-tert-butyl-2-ethoxy-phenyl)-4,5-dihydro-imidazole-1-carbonyl]-piperazin-1-yl}-1-morpholin-4-yl-ethanone hydrochloride was prepared from (4S,5R)-4,5-bis-(4-bromo-phenyl)-2-(4-tert-butyl-2-ethoxy-phenyl)-4,5-dihydro-imidazole-1-carbonyl chloride (example 12b) and 1-morpholin-4-yl-2-piperazin-1-yl-ethanone (Oakwood Products) in an analogous manner as described in example 25. LR-MS: 794.3 [(M+H)⁺]

Example 34

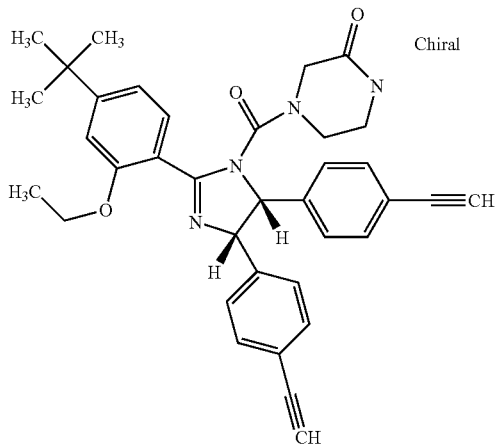

4-[(4S,5R)-2-(4-tert-Butyl-2-ethoxy-phenyl)-4,5-bis-(4-ethynyl-phenyl)-4,5-dihydro-imidazole-1-carbonyl]-piperazin-2-one was prepared from (4S,5R)-2-(4-tert-butyl-2-ethoxy-phenyl)-4,5-bis-(4-ethynyl-phenyl)-4,5-dihydro-imidazole-1-carbonyl chloride (example 12c) and 2-piperazinone (Avocado Organics) in an analogous manner as described in example 25. LR-MS: 573.5 [(M+H)$^+$]

Example 35

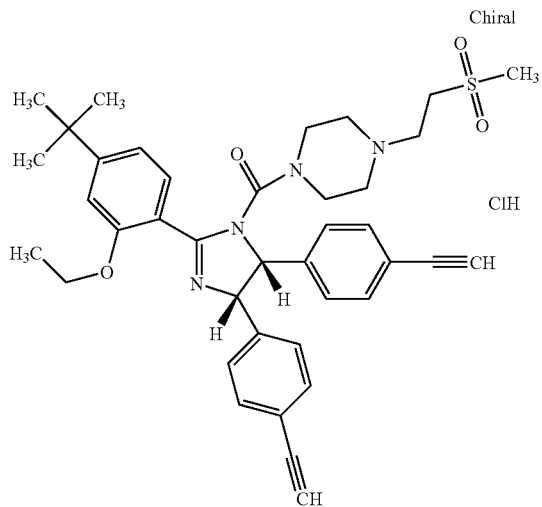

[(4S,5R)-2-(4-tert-Butyl-2-ethoxy-phenyl)-4,5-bis-(4-ethynyl-phenyl)-4,5-dihydro-imidazol-1-yl]-[4-(2-methanesulfonyl-ethyl)-piperazin-1-yl]-methanone hydrochloride was prepared from (4S,5R)-2-(4-tert-butyl-2-ethoxy-phenyl)-4,5-bis-(4-ethynyl-phenyl)-4,5-dihydro-imidazole-1-carbonyl chloride (example 12c) and 1-(2-methanesulfonyl-ethyl)-piperazine dihydrochloride (example 17) in an analogous manner as described in example 25. LR-MS: 665.5 [(M+H)$^+$]

Example 36

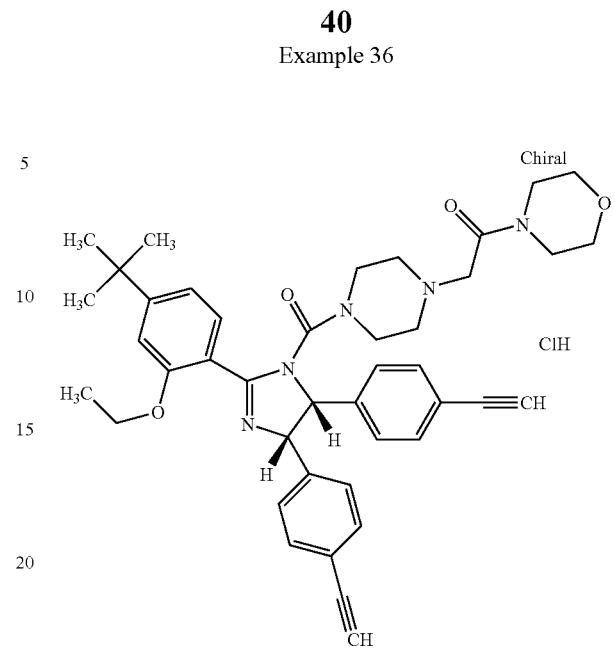

2-{4-[(4S,5R)-2-(4-tert-Butyl-2-ethoxy-phenyl)-4,5-bis-(4-ethynyl-phenyl)-4,5-dihydro-imidazole-1-carbonyl]-piperazin-1-yl}-1-morpholin-4-yl-ethanone hydrochloride was prepared from (4S,5R)-2-(4-tert-butyl-2-ethoxy-phenyl)-4,5-bis-(4-ethynyl-phenyl)-4,5-dihydro-imidazole-1-carbonyl chloride (example 12c) and 1-morpholin-4-yl-2-piperazin-1-yl-ethanone (Oakwood Products) in an analogous manner as described in example 25. LR-MS: 686.6 [(M+H)$^+$]

Example 37

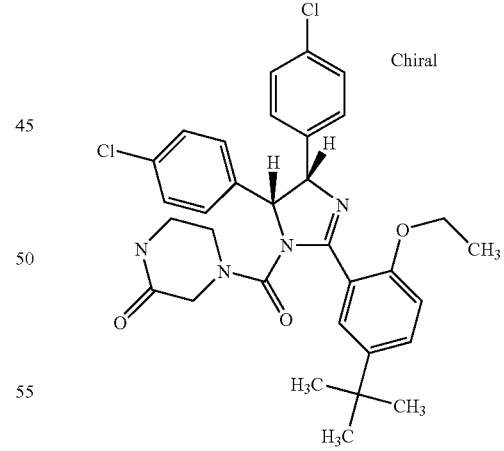

4-[(4S,5R)-2-(5-tert-Butyl-2-ethoxy-phenyl)-4,5-bis-(4-chloro-phenyl)-4,5-dihydro-imidazole-1-carbonyl]-piperazin-2-one was prepared from (4S,5R)-2-(5-tert-butyl-2-ethoxy-phenyl)-4,5-bis-(4-chloro-phenyl)-4,5-dihydro-imidazole-1-carbonyl chloride (example 12d) and 2-piperazinone (Avocado Organics) in an analogous manner as described in example 25. LR-MS: 593.3 [(M+H)$^+$]

Example 38

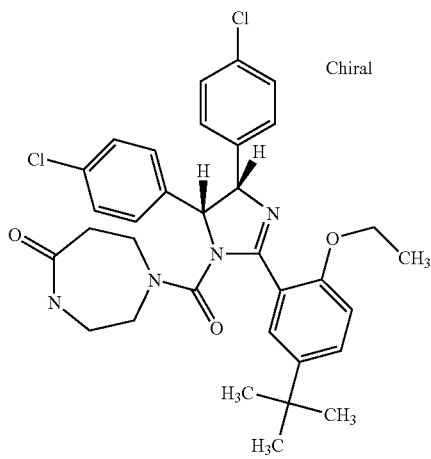

1-[(4S,5R)-2-(5-tert-Butyl-2-ethoxy-phenyl)-4,5-bis-(4-chloro-phenyl)-4,5-dihydro-imidazole-1-carbonyl]-[1,4]diazepan-5-one was prepared from (4S,5R)-2-(5-tert-butyl-2-ethoxy-phenyl)-4,5-bis-(4-chloro-phenyl)-4,5-dihydro-imidazole-1-carbonyl chloride (example 12d) and [1,4]diazepan-5-one (Oakwood Products) in an analogous manner as described in example 25. LR-MS: 607.3 [(M+H)$^+$]

Example 39

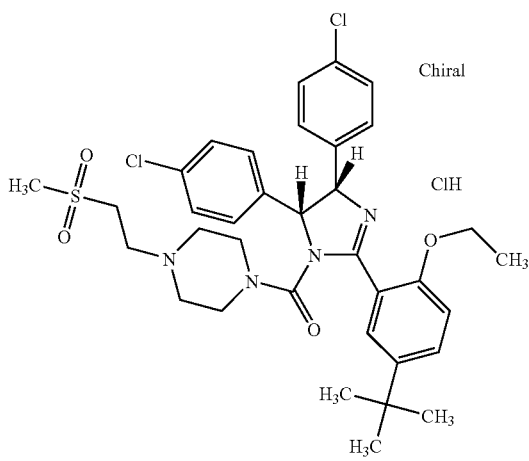

[(4S,5R)-2-(5-tert-Butyl-2-ethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride was prepared from (4S,5R)-2-(5-tert-butyl-2-ethoxy-phenyl)-4,5-bis-(4-chloro-phenyl)-4,5-dihydro-imidazole-1-carbonyl chloride (example 12d) and 1-(2-methanesulfonyl-ethyl)piperazine dihydrochloride (example 17) in an analogous manner as described in example 25. LR-MS: 685.3 [(M+H)$^+$]

Example 40

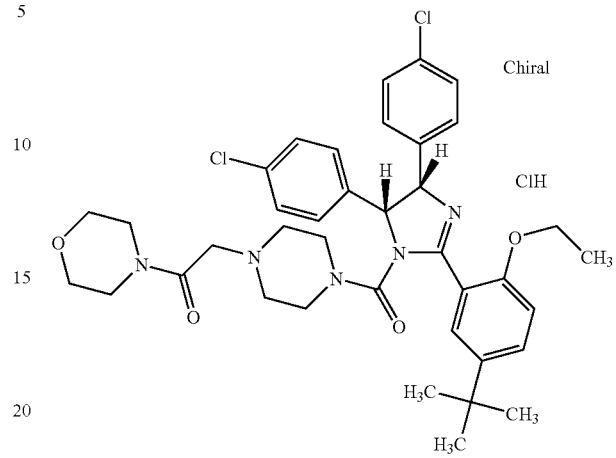

2-{4-[(4S,5R)-2-(5-tert-Butyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride was prepared from (4S,5R)-2-(5-tert-butyl-2-ethoxy-phenyl)-4,5-bis-(4-chloro-phenyl)-4,5-dihydro-imidazole-1-carbonyl chloride (example 12d) and 1-morpholin-4-yl-2-piperazin-1-yl-ethanone (Oakwood Products) in an analogous manner as described in example 25. LR-MS: 706.4 [(M+H)$^+$]

Example 41

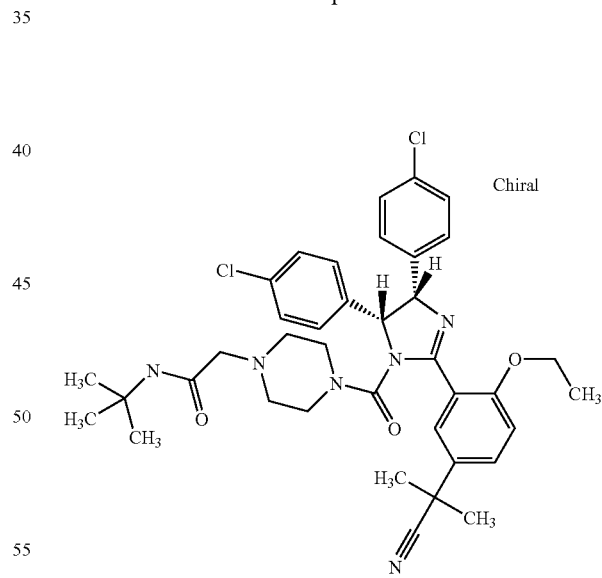

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N-tert-butyl-acetamide was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and 3-piperazin-1yl-propionitrile (example 16f) in an analogous manner as described in example 25. LR-MS: 703.4 [(M+H)$^+$]

Example 42

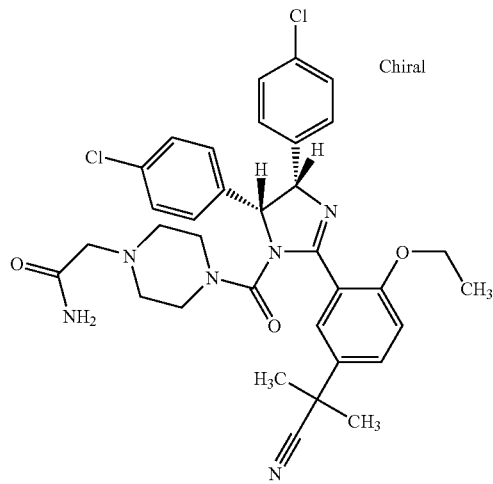

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-acetamide was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and 2-piperazin-1-yl-acetamide (Matrix) in an analogous manner as described in example 25. LR-MS: 647.2 [(M+H)$^+$]

Example 43

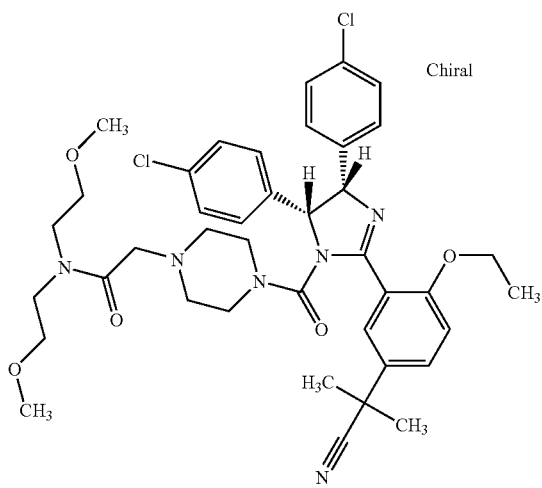

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N,N-bis-(2-methoxy-ethyl)-acetamide was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and N,N-bis-(2-methoxy-ethyl)-2-piperazin-1-yl-acetamide (example 16) in an analogous manner as described in example 25. LR-MS: 763.4 [(M+H)$^+$]

Example 44

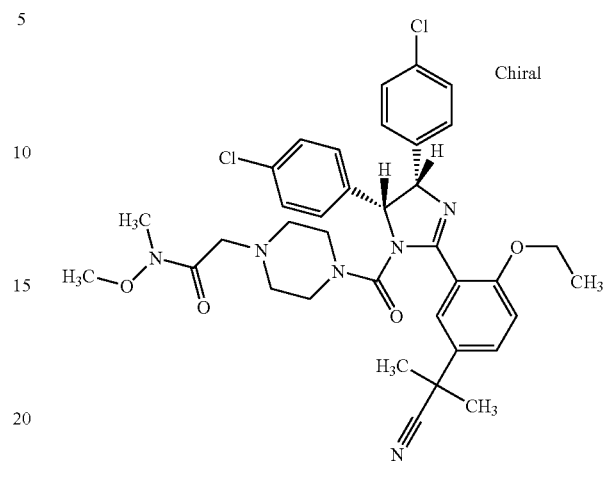

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N-methoxy-N-methyl-acetamide was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and N-methoxy-N-methyl-2-piperazin-1-yl-acetamide (example 16b) in an analogous manner as described in example 25. LR-MS: 691.3 [(M+H)$^+$]

Example 45

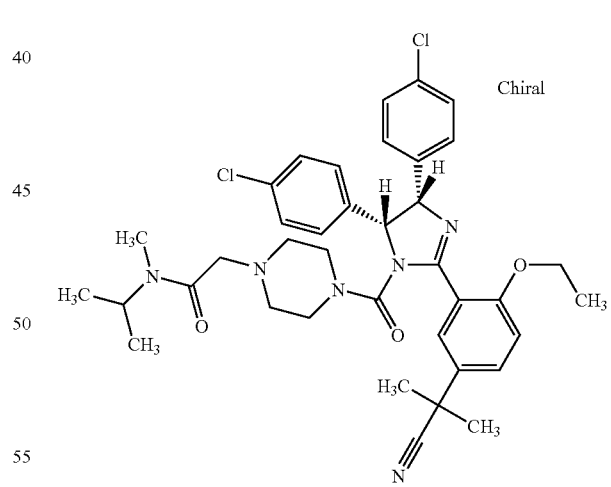

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin 1-yl)-N-isopropyl-N-methyl-acetamide was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and N-isopropyl-N-methyl-2-piperazin-1-yl-acetamide (example 16c) in an analogous manner as described in example 25. LR-MS: 703.4 [(M+H)$^+$]

Example 46

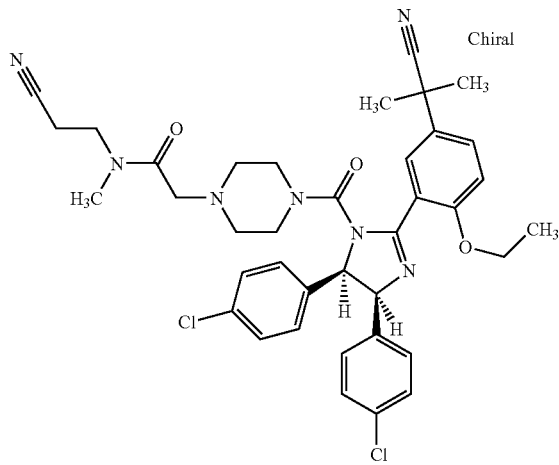

2-(4-{(4S,5R)-4,5-Bis-(4-chloro-phenyl)-2-[5-(cyano-dimethyl-methyl)-2-ethyl-phenyl]-4,5-dihydro-imidazole-1-carbonyl}-piperazin-1-yl)-N-(2-cyano-ethyl)-N-methyl-acetamide was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and N-(2-cyano-ethyl)-N-methyl-2-piperazin-1-yl-acetamide (example 16d) in an analogous manner as described in example 25. LR-MS: 714.3 [(M+H)+]

Example 47

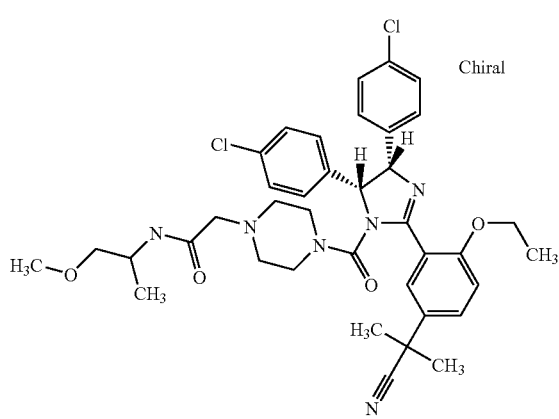

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N-(2-methoxy-1-methyl-ethyl)-acetamide was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and N-(2-methoxy-1-methylethyl)-2-piperazin-1-yl-acetamide (example 15) in an analogous manner as described in example 25. LR-MS: 719.4 [(M+H)+]

Example 48

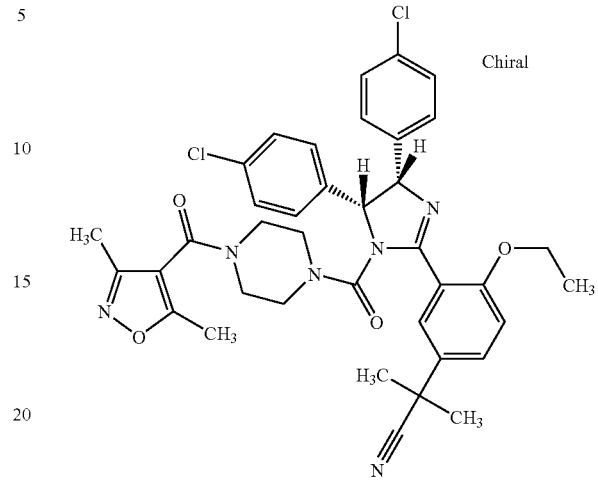

2-(3-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-phenyl)-2-methyl-propionitrile was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and (3,5-dimethyl-isoxazol-4-yl)-piperazin-1-yl-methanone (example 13) in an analogous manner as described in example 25. LR-MS: 713.3 [(M+H)+]

Example 49

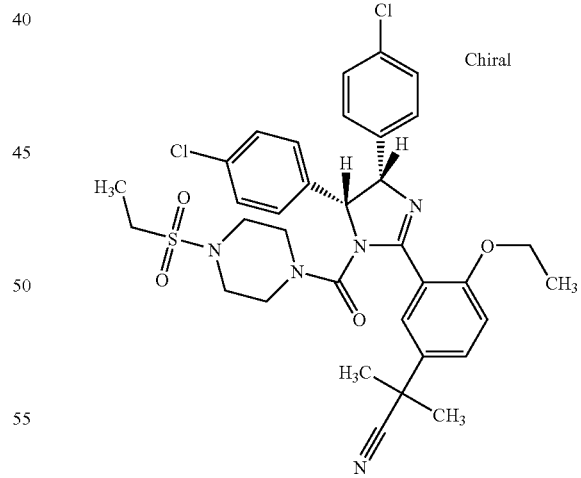

2-{3-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-phenyl}-2-methyl-propionitrile was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and 1-ethanesulfonyl-piperazine (example 14) in an analogous manner as described in example 25. LR-MS: 682.3 [(M+H)+]

Example 50

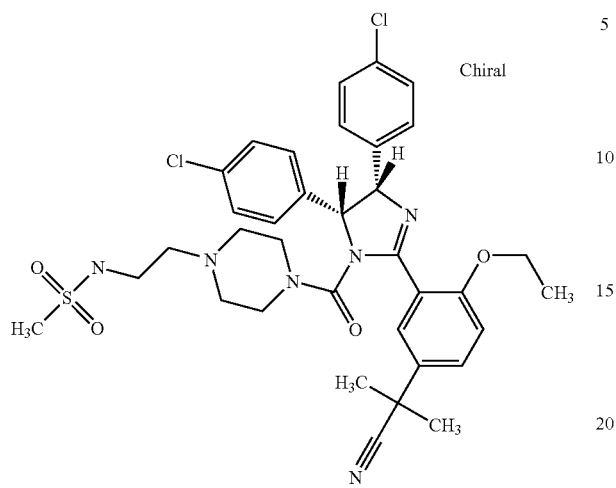

N-[2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-ethyl]-methanesulfonamide was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and N-(2-methanosulfonylethyl)-piperazine hydrochloride (example 22) in an analogous manner as described in example 25. LR-MS: 711.4 [(M+H)$^+$]

Example 52

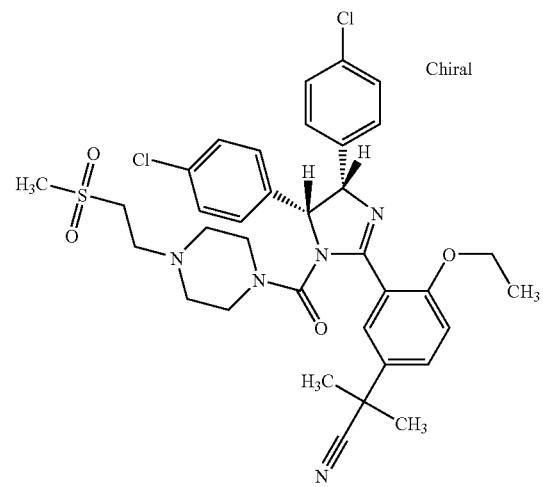

2-(3-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-phenyl)-2-methyl-propionitrile was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and 1-(2-methanesulfonylethyl)piperazine dihydrochloride (example 17) in an analogous manner as described in example 25. LR-MS: 696.3 [(M+H)$^+$]

Example 51

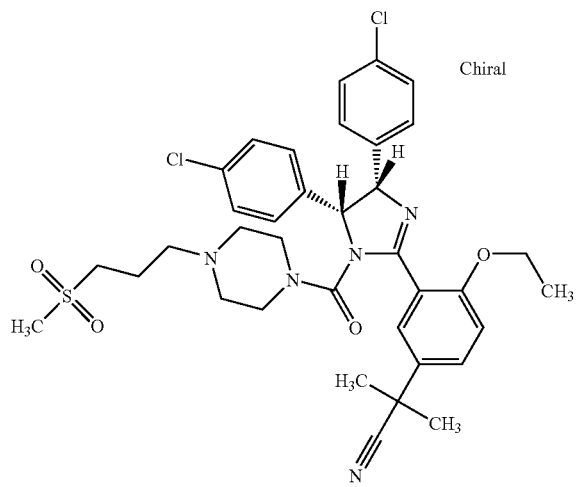

2-(3-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-phenyl)-2-methyl-propionitrile was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and 1-(3-methanesulfonyl-propyl)-piperazine (example 16e) in an analogous manner as described in example 25. LR-MS: 710.4 [(M+H)$^+$]

Example 53

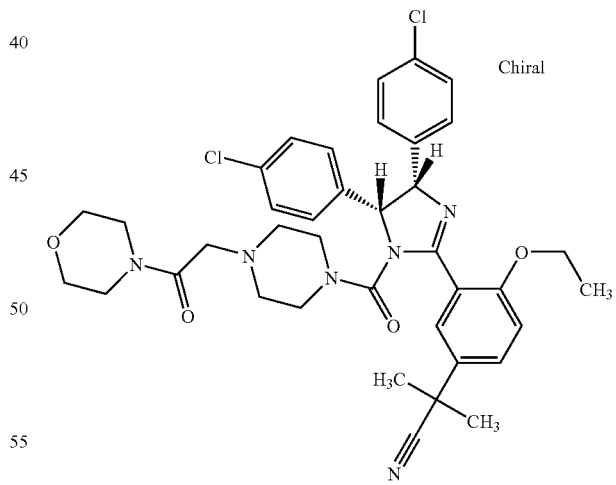

2-(3-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-phenyl)-2-methyl-propionitrile was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and 1-morpholin-4-yl-2-piperazin-1-yl-ethanone (Oakwood Products) in an analogous manner as described in example 25. LR-MS: 717.3 [(M+H)$^+$]

Example 54

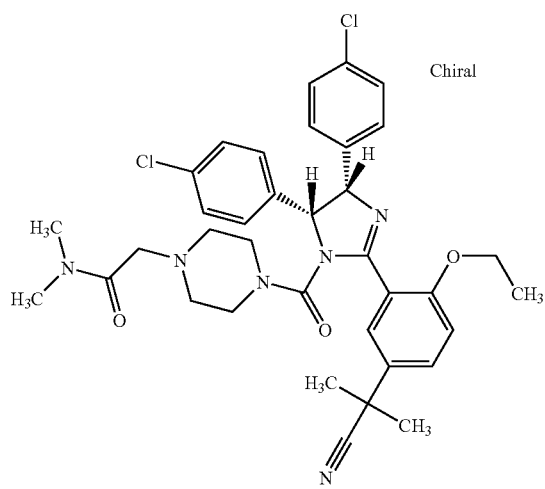

2-(4-{(4S,5R)-4,5-Bis-(4-chloro-phenyl)-2-[5-(cyano-dimethyl-methyl)-2-ethoxy-phenyl]-4,5-dihydro-imidazole-1-carbonyl}-piperazin-1-yl)-N,N-dimethyl-acetamide was prepared from (4S,5R)-4,5-bis-(4-chloro-phenyl)-2-[5-(cyano-dimethyl-methyl)-2-ethoxy-phenyl]-4,5-dihydro-imidazole-1-carbonyl chloride (example 12e) and N,N-dimethyl-2-piperazin-1-yl-acetamide (Oakwood Products) in an analogous manner as described in example 25. LR-MS: 675.3 [(M+H)+]

Example 55

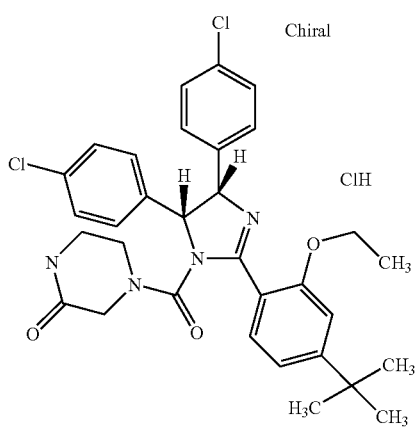

4-[(4S,5R)-2-(4-tert-Butyl-2-ethoxy-phenyl)-4,5-bis-(4-chloro-phenyl)-4,5-dihydro-imidazole-1-carbonyl]-piperazin-2-one hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 2-piperazinone (Avocado Organics) in an analogous manner as described in example 25. LR-MS: 593.4 [(M+H)+]

Example 56

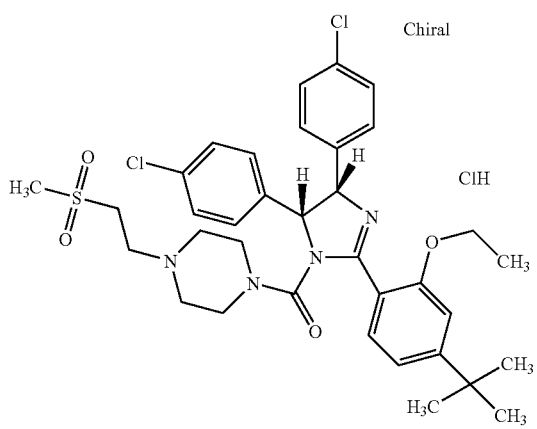

[(4S,5R)-2-(4-tert-Butyl-2-ethoxy-phenyl)-4,5-bis-(4-chloro-phenyl)-4,5-dihydro-imidazol-1-yl-]-[4-(2-methane-sulfonyl-ethyl)-piperazin-1-yl]-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-(2-methanesulfonyl-ethyl)piperazine dihydrochloride (example 17) in an analogous manner as described in example 25. LR-MS: 685.3 [(M+H)+]

Example 57

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-N,N-dimethyl-acetamide hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and N,N-dimethyl-2-piperazin-1-yl-acetamide (Oakwood Products) in an analogous manner as described in example 25. LR-MS: 664.4 [(M+H)+]

Example 58

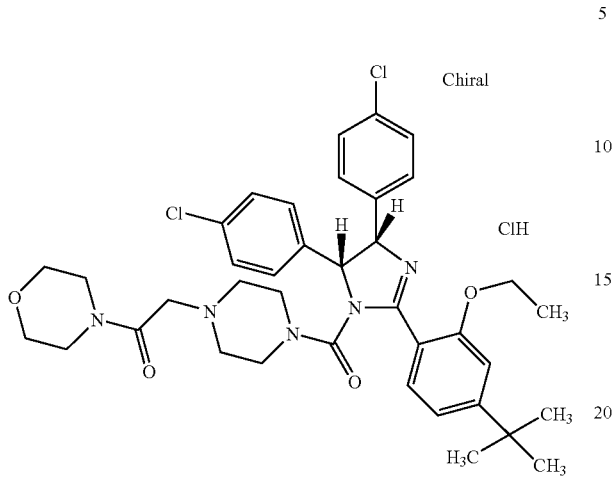

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-morpholin-4-yl-2-piperazin-1-yl-ethanone (Oakwood Products) in an analogous manner as described in example 25. LR-MS: 706.5 [(M+H)$^+$]

Example 59

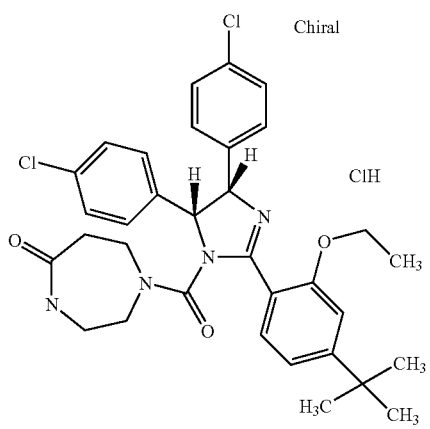

1-[(4S,5R)-2-(4-tert-Butyl-2-ethoxy-phenyl)-4,5-bis-(4-chloro-phenyl)-4,5-dihydro-imidazole-1-carbonyl]-[1,4]diazepan-5-one hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and [1,4]diazepan-5-one (Oakwood Products) in an analogous manner as described in example 25. LR-MS: 607.4 [(M+H)$^+$]

Example 60

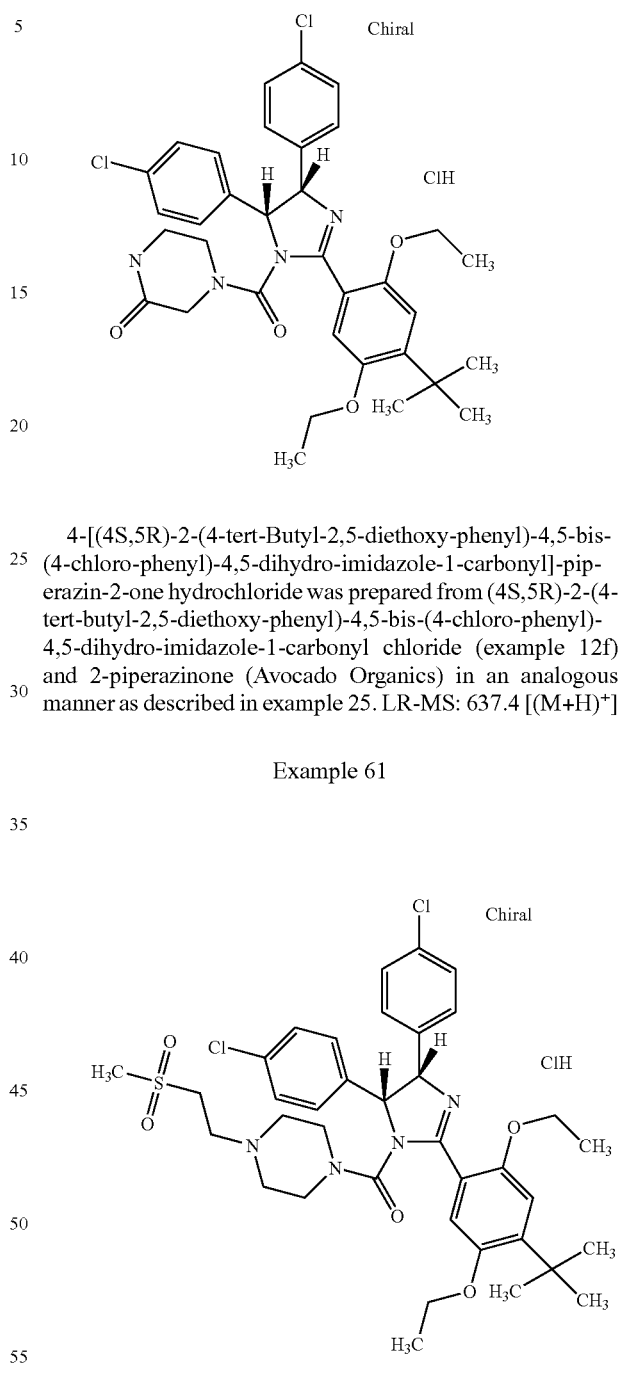

4-[(4S,5R)-2-(4-tert-Butyl-2,5-diethoxy-phenyl)-4,5-bis-(4-chloro-phenyl)-4,5-dihydro-imidazole-1-carbonyl]-piperazin-2-one hydrochloride was prepared from (4S,5R)-2-(4-tert-butyl-2,5-diethoxy-phenyl)-4,5-bis-(4-chloro-phenyl)-4,5-dihydro-imidazole-1-carbonyl chloride (example 12f) and 2-piperazinone (Avocado Organics) in an analogous manner as described in example 25. LR-MS: 637.4 [(M+H)$^+$]

Example 61

[(4S,5R)-2-(4-tert-Butyl-2,5-diethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride was prepared from (4S,5R)-2-(4-tert-butyl-2,5-diethoxy-phenyl)-4,5-bis-(4-chloro-phenyl)-4,5-dihydro-imidazole-1-carbonyl chloride (example 12f) and 1-(2-methanesulfonylethyl)piperazine dihydrochloride (example 17) in an analogous manner as described in example 25. LR-MS: 729.4 [(M+H)$^+$]

Example 62

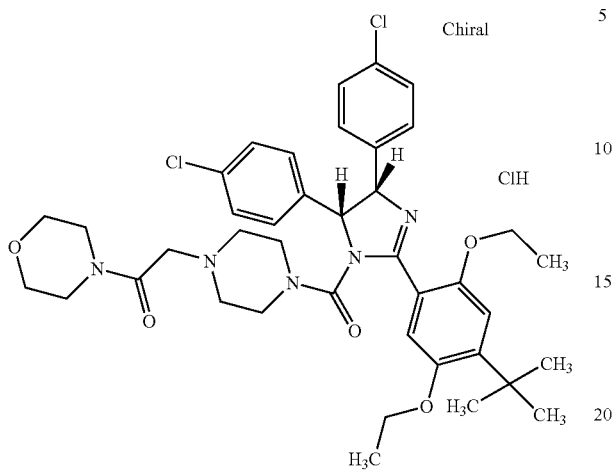

2-{4-[(4S,5R)-2-(4-tert-Butyl-2,5-diethoxy-phenyl)-4,5-bis-(4-chloro-phenyl)-4,5-dihydro-imidazole-1-carbonyl]-piperazin-1-yl}-1-morpholin-4-yl-ethanone hydrochloride was prepared from (4S,5R)-2-(4-tert-butyl-2,5-diethoxy-phenyl)-4,5-bis-(4-chloro-phenyl)-4,5-dihydro-imidazole-1-carbonyl chloride (example 12f) and 1-morpholin-4-yl-2-piperazin-1-yl-ethanone (Oakwood Products) in an analogous manner as described in example 25. LR-MS: 750.4 [(M+H)$^+$]

Example 63

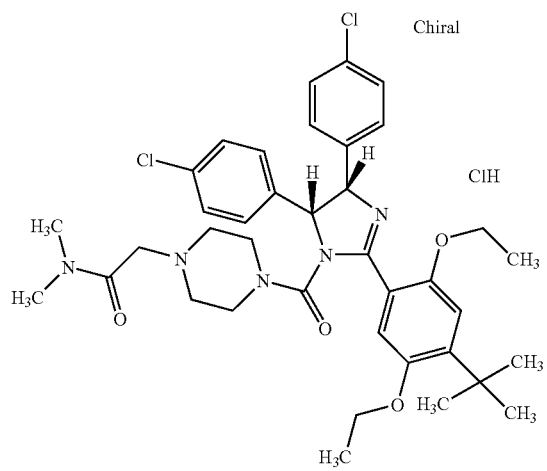

2-{4-[(4S,5R)-2-(4-tert-Butyl-2,5-diethoxy-phenyl)-4,5-bis-(4-chloro-phenyl)-4,5-dihydro-imidazole-1-carbonyl]-piperazin-1-yl}-N,N-dimethyl-acetamide hydrochloride was prepared from (4S,5R)-2-(4-tert-butyl-2,5-diethoxy-phenyl)-4,5-bis-(4-chloro-phenyl)-4,5-dihydro-imidazole-1-carbonyl chloride (example 12f) and N,N-dimethyl-2-piperazin-1-yl-acetamide (Oakwood Products) in an analogous manner as described in example 25. LR-MS: 708.4 [(M+H)$^+$]

Example 64

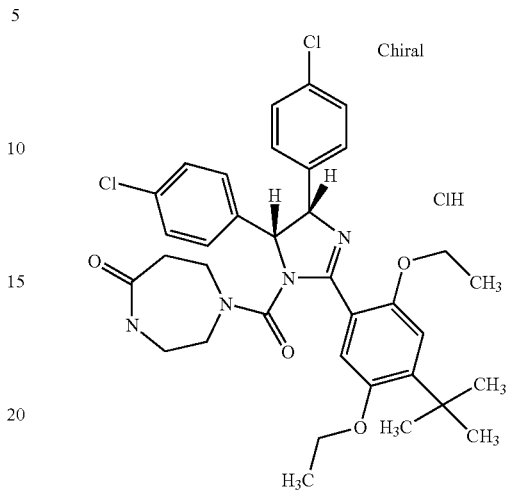

1-[(4S,5R)-2-(4-tert-Butyl-2,5-diethoxy-phenyl)-4,5-bis-(4-chloro-phenyl)-4,5-dihydro-imidazole-1-carbonyl]-[1,4]diazepan-5-one hydrochloride was prepared from (4S,5R)-2-(4-tert-butyl-2,5-diethoxy-phenyl)-4,5-bis-(4-chloro-phenyl)-4,5-dihydro-imidazole-1-carbonyl chloride (example 12f) and [1,4]diazepan-5-one (Oakwood Products) in an analogous manner as described in example 25. LR-MS: 651.4 [(M+H)$^+$]

Example 65

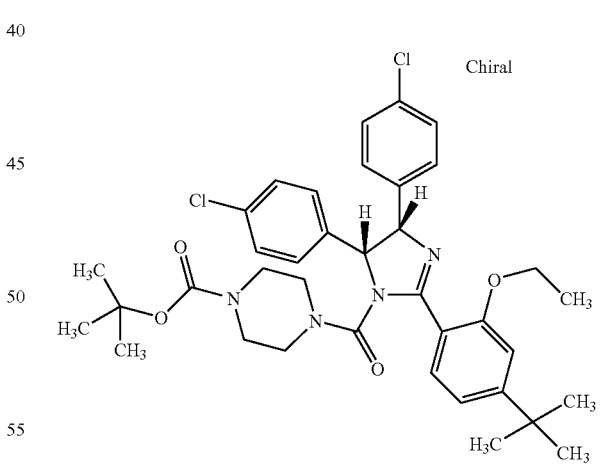

4-[(4S,5R)-2-(4-tert-Butyl-2-ethoxy-phenyl)-4,5-bis-(4-chloro-phenyl)-4,5-dihydro-imidazole-1-carbonyl]-piperazine-1-carboxylic acid tert-butyl ester was prepared from (4S,5R)-2-(4-tert-butyl-2-ethoxy-phenyl)-4,5-bis-(4-chloro-phenyl)-4,5-dihydro-imidazole-1-carbonyl chloride (example 11) and tert-butyl piperazine-1-carboxylate in an analogous manner as described in example 25. LR-MS: 679.4 [(M+H)$^+$]

Example 66

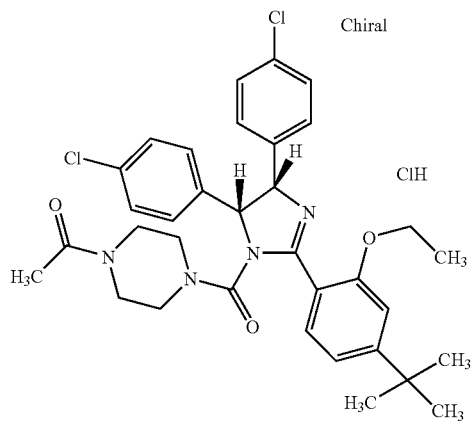

1-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-ethanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-acetyl-piperazine in an analogous manner as described in example 25. LR-MS: 621.4 [(M+H)$^+$]

Example 67

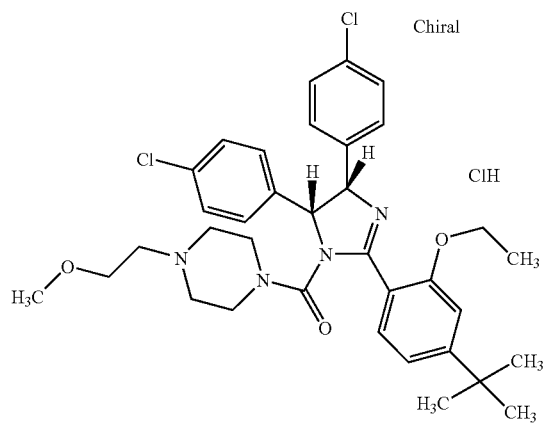

[(4S,5R)-2-(4-tert-Butyl-2-ethoxy-phenyl)-4,5-bis-(4-chloro-phenyl)-4,5-dihydro-imidazol-1-yl]-[4-(2-methoxy-ethyl)-piperazin-1-yl]-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-(2-methoxy-ethyl)-piperazine in an analogous manner as described in example 25. LR-MS: 637.4 [(M+H)$^+$]

Example 68

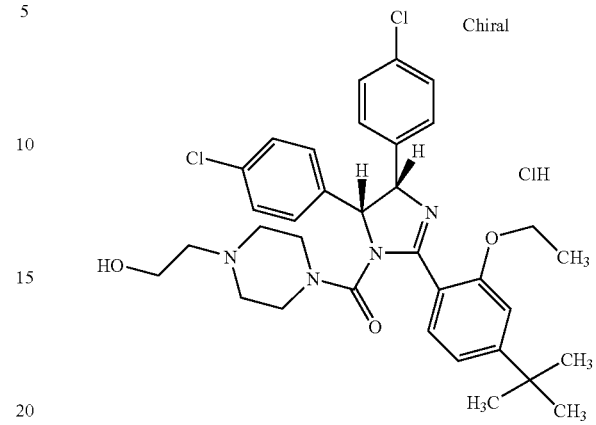

[(4S,5R)-2-(4-tert-Butyl-2-ethoxy-phenyl)-4,5-bis-(4-chloro-phenyl)-4,5-dihydro-imidazol-1-yl]-[4-(2-hydroxy-ethyl)-piperazin-1-yl]-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-(2-hydroxy-ethyl)-piperazine in an analogous manner as described in example 25. LR-MS: 623.4 [(M+H)$^+$]

Example 69

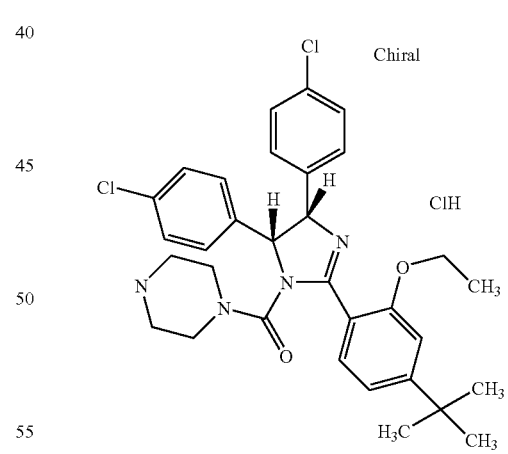

[(4S,5R)-2-(4-tert-Butyl-2-ethoxy-phenyl)-4,5-bis-(4-chloro-phenyl)-4,5-dihydro-imidazol-1-yl]-piperazin-1-yl-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and piperazine in an analogous manner as described in example 25. LR-MS: 579.4 [(M+H)$^+$]

Example 70

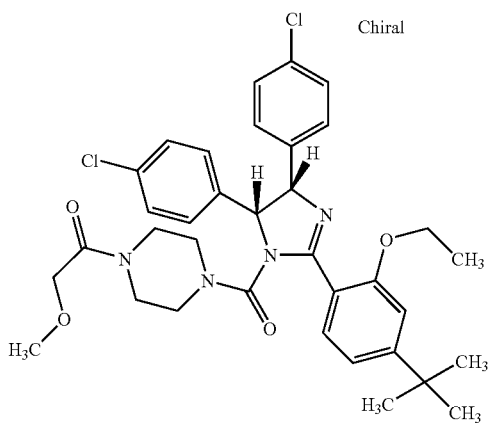

1-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-2-methoxy-ethanone was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 2-methoxy-1-piperazin-1-yl-ethanone in an analogous manner as described in example 25. LR-MS: 651.4 [(M+H)]

Example 71

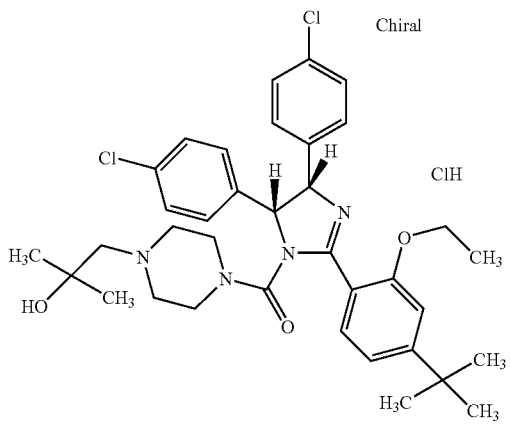

[(4S,5R)-2-(4-tert-Butyl-2-ethoxy-phenyl)-4,5-bis-(4-chloro-phenyl)-4,5-dihydro-imidazol-1-yl]-[4-(2-hydroxy-2-methyl-propyl)-piperazin-1-yl]-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 2-methyl-1-piperazin-1-yl-propan-2-ol (example 18a) in an analogous manner as described in example 25. LR-MS: 651.4 [(M+H)$^+$]

Example 72

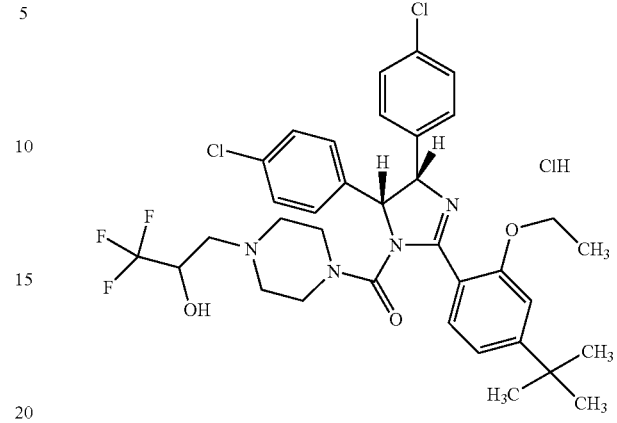

[(4S,5R)-2-(4-tert-Butyl-2-ethoxy-phenyl)-4,5-bis-(4-chloro-phenyl)-4,5-dihydro-imidazol-1-yl]-[4-(3,3,3-trifluoro-2-hydroxy-propyl)-piperazin-1-yl]-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1,1,1-trifluoro-3-piperazin-1-yl-propan-2-ol (example 18b) in an analogous manner as described in example 25. LR-MS: 691.4 [(M+H)$^+$]

Example 73

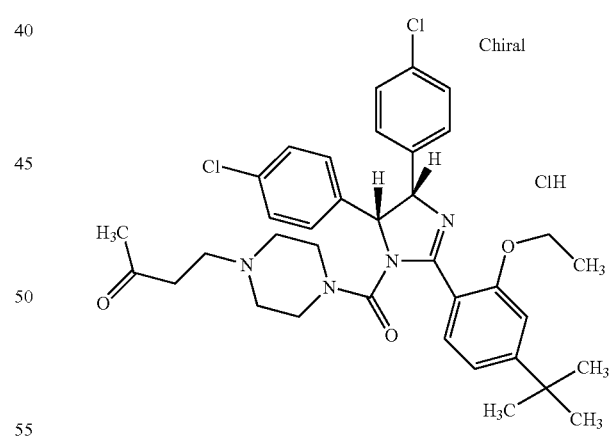

4-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-butan-2-one hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 4-piperazin-1-yl-butan-2-one (example 18c) in an analogous manner as described in example 25. LR-MS: 649.4 [(M+H)$^+$]

Example 74

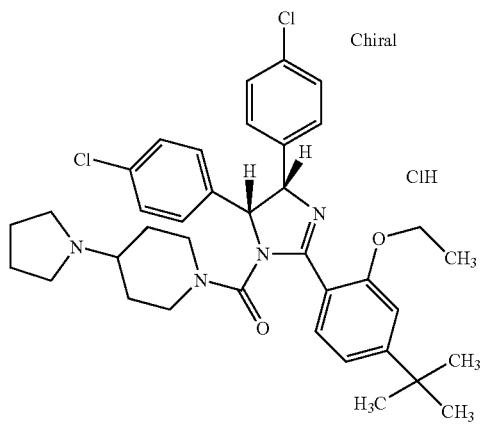

[(4S,5R)-2-(4-tert-Butyl-2-ethoxy-phenyl)-4,5-bis-(4-chloro-phenyl)-4,5-dihydro-imidazol-1-yl]-(4-pyrrolidin-1-yl-piperidin-1-yl)-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 4-pyrrolidin-1-yl-piperidine in an analogous manner as described in example 25. LR-MS: 647.4 [(M+H)$^+$]

Example 76

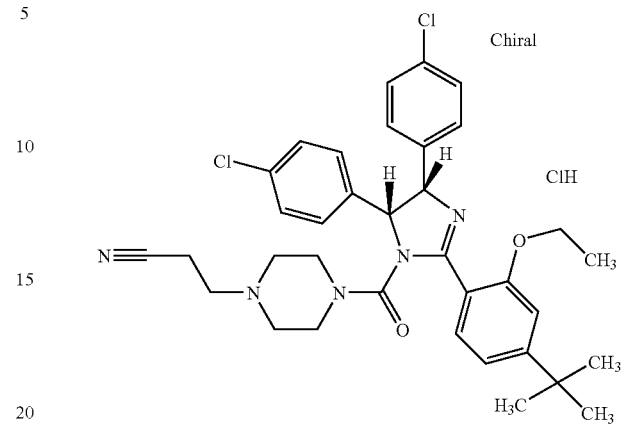

3-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-propionitrile hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 3-piperazin-1-yl-propionitrile (example 16f) in an analogous manner as described in example 25. LR-MS: 632.4 [(M+H)$^+$]

Example 75

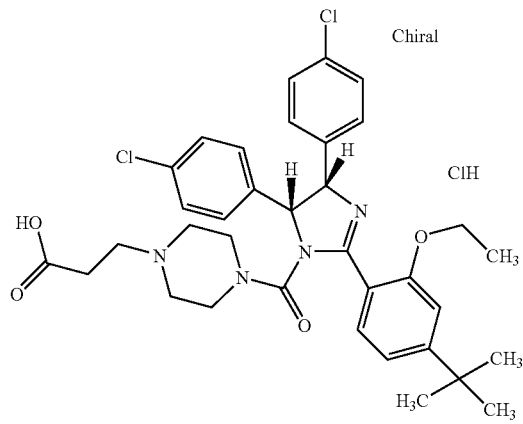

3-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-propionic acid hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 3-piperazin-1-yl-propionic acid in an analogous manner as described in example 25. LR-MS: 651.4 [(M+H)$^+$]

Example 77

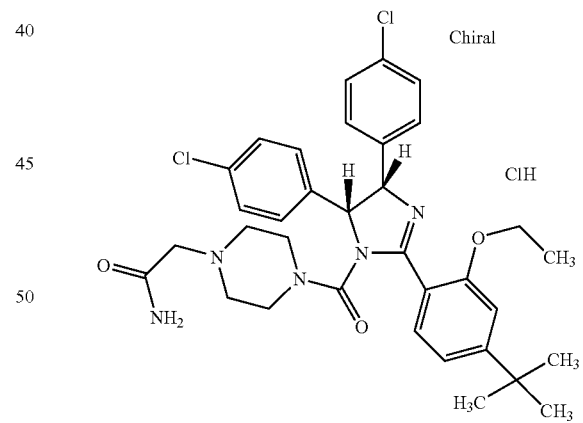

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-acetamide hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 2-piperazin-1-yl-acetamide (Oakwood Products) in an analogous manner as described in example 25. LR-MS: 636.4 [(M+H)$^+$]

Example 78

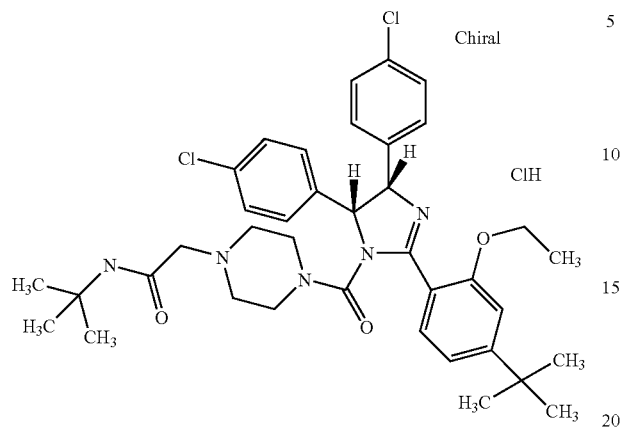

N-tert-Butyl-2-{4-[(4S,5R)-2-(4-tert-butyl-2-ethoxy-phenyl)-4,5-bis-(4-chloro-phenyl)-4,5-dihydro-imidazole-1-carbonyl]-piperazin-1-yl}-acetamide hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and N-tert-butyl-2-piperazin-1-yl-acetamide (example 16g) in an analogous manner as described in example 25. LR-MS: 692.5 [(M+H)$^+$]

Example 79

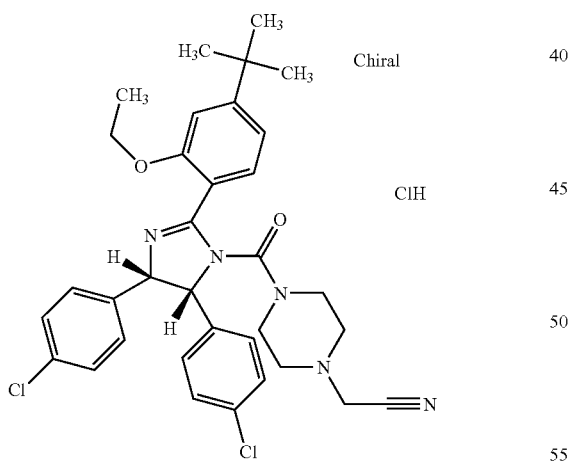

{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-acetonitrile hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and piperazin-1-yl-acetonitrile (example 16h) in an analogous manner as described in example 25. LR-MS: 618.5 [(M+H)$^+$]

Example 80

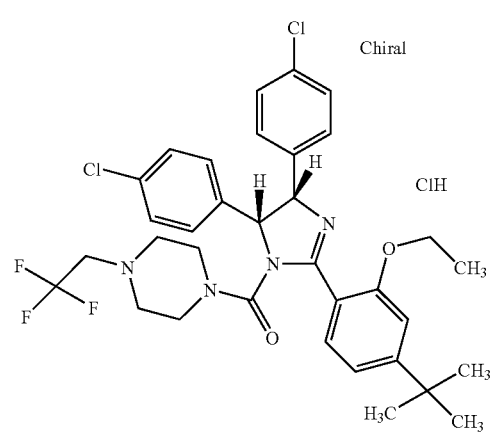

[(4S,5R)-2-(4-tert-Butyl-2-ethoxy-phenyl)-4,5-bis-(4-chloro-phenyl)-4,5-dihydro-imidazol-1-yl]-[4-(2,2,2-trifluoro-ethyl)-piperazin-1-yl]-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-(2,2,2-trifluoroethyl)piperazine dihydrochloride (example 26) in an analogous manner as described in example 25. LR-MS: 661.4 [(M+H)$^+$]

Example 81

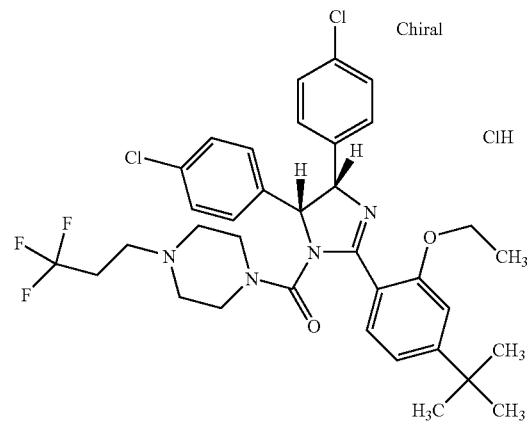

[(4S,5R)-2-(4-tert-Butyl-2-ethoxy-phenyl)-4,5-bis-(4-chloro-phenyl)-4,5-dihydro-imidazol-1-yl]-[4-(3,3,3-trifluoro-propyl)-piperazin-1-yl]-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-(3,3,3-trifluoro-propyl)-piperazine (example 16i) in an analogous manner as described in example 25. LR-MS: 675.4 [(M+H)$^+$]

Example 82

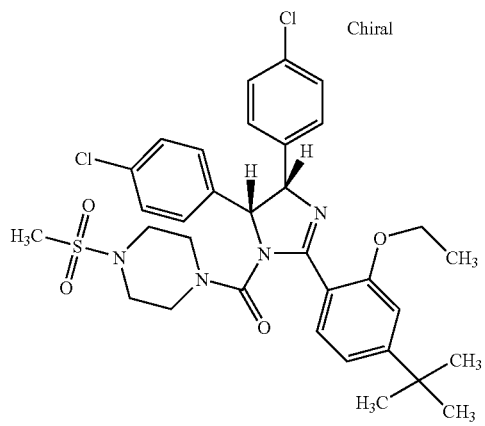

[(4S,5R)-2-(4-tert-Butyl-2-ethoxy-phenyl)-4,5-bis-(4-chloro-phenyl)-4,5-dihydro-imidazol-1-yl]-(4-methanesulfonyl-piperazin-1-yl)-methanone was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-methanesulfonyl-piperazine in an analogous manner as described in example 25. LR-MS: 657.4 [(M+H)$^+$]

Example 83

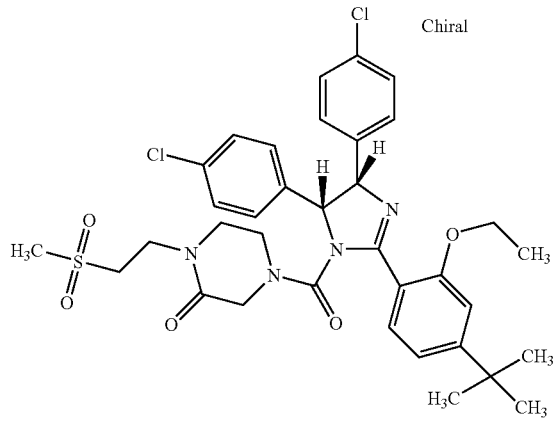

4-[(4S,5R)-2-(4-tert-Butyl-2-ethoxy-phenyl)-4,5-bis-(4-chloro-phenyl)-4,5-dihydro-imidazole-1-carbonyl]-1-(2-methanesulfonyl-ethyl)-piperazin-2-one was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-(2-methanosulfonylethyl)-piperazine-2-one (example 21) in an analogous manner as described in example 25. LR-MS: 699.3 [(M+H)$^+$]

Example 84

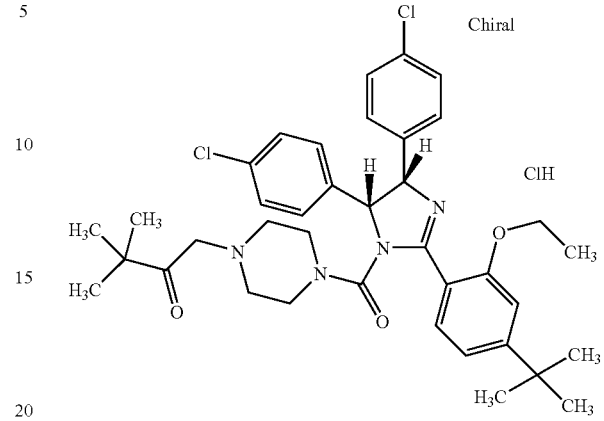

1-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-3,3-dimethyl-butan-2-one hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 3,3-dimethyl-1-piperazin-1-yl-butan-2-one (example 16j) in an analogous manner as described in example 25. LR-MS: 677.5 [(M+H)$^+$]

Example 85

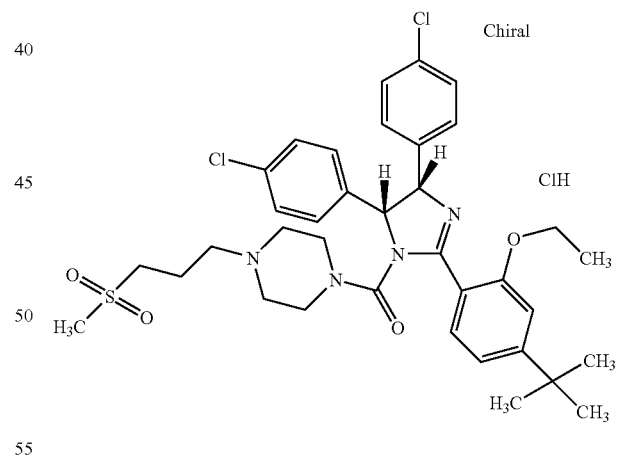

[(4S,5R)-2-(4-tert-Butyl-2-ethoxy-phenyl)-4,5-bis-(4-chloro-phenyl)-4,5-dihydro-imidazol-1-yl]-[4-(3-methanesulfonyl-propyl)-piperazin-1-yl]-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-(3-methanesulfonyl-propyl)-piperazine (example 16e) in an analogous manner as described in example 25. LR-MS: 699.3 [(M+H)$^+$]

Example 86

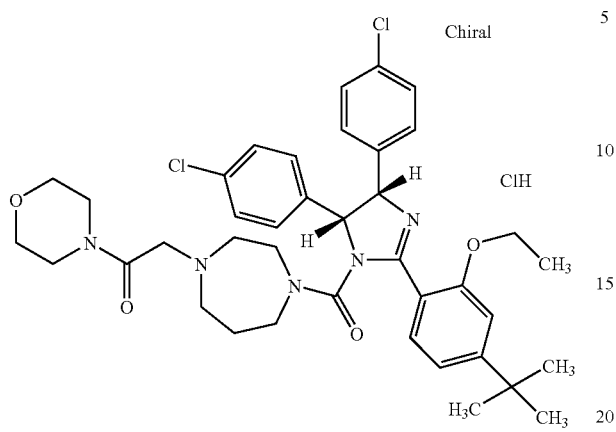

2-{4-[(4S,5R)-2-(4-tert-Butyl-2-ethoxy-phenyl)-4,5-bis-(4-chloro-phenyl)-4,5-dihydro-imidazole-1-carbonyl]-[1,4]diazepan-1-yl}-1-morpholin-4-yl-ethanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 2-[1,4]diazepan-1-yl-1-morpholin-4-yl-ethanone (example 20a) in an analogous manner as described in example 25. LR-MS: 720.5 [(M+H)+]

Example 87

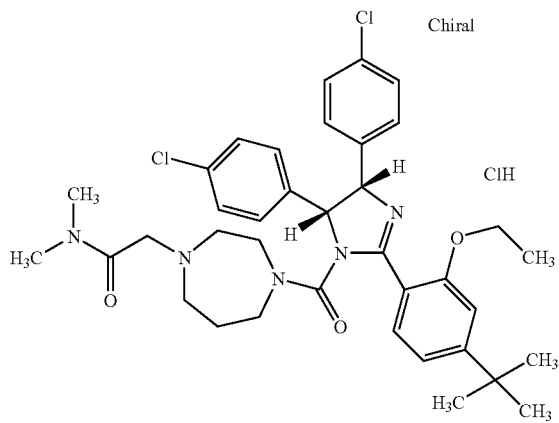

2-{4-[(4S,5R)-2-(4-tert-Butyl-2-ethoxy-phenyl)-4,5-bis-(4-chloro-phenyl)-4,5-dihydro-imidazole-1-carbonyl]-[1,4]diazepan-1-yl}-N,N-dimethyl-acetamide hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 2-[1,4]diazepan-1-yl-N,N-dimethyl-acetamide (example 20b) in an analogous manner as described in example 25. LR-MS: 678.5 [(M+H)+]

Example 88

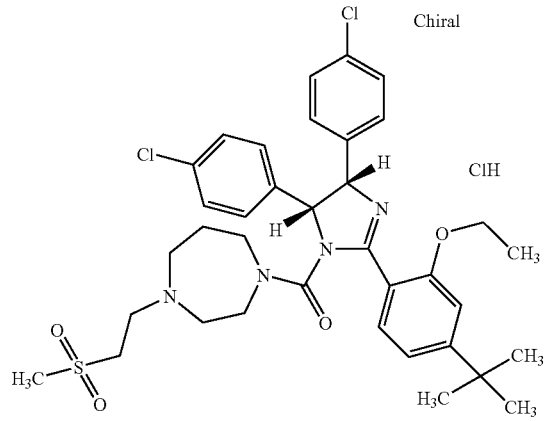

[(4S,5R)-2-(4-tert-Butyl-2-ethoxy-phenyl)-4,5-bis-(4-chloro-phenyl)-4,5-dihydro-imidazol-1-yl]-[4-(2-methanesulfonyl-ethyl)-[1,4]diazepan-1-yl]-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 1-(2-methanesulfonyl-ethyl)-[1,4]diazepane (example 19) in an analogous manner as described in example 25. LR-MS: 699.4 [(M+H)+]

Example 89

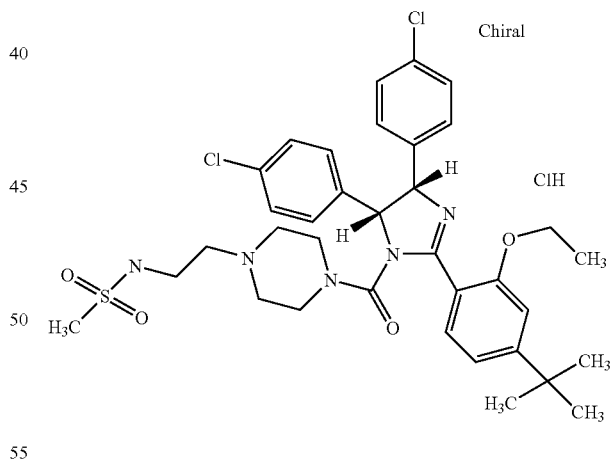

N-(2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-ethyl)-methanesulfonamide hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and N-(2-methanosulfonyl-ethyl)-piperazine hydrochloride (example 22) in an analogous manner as described in example 25. LR-MS: 700.4 [(M+H)+]

Example 90

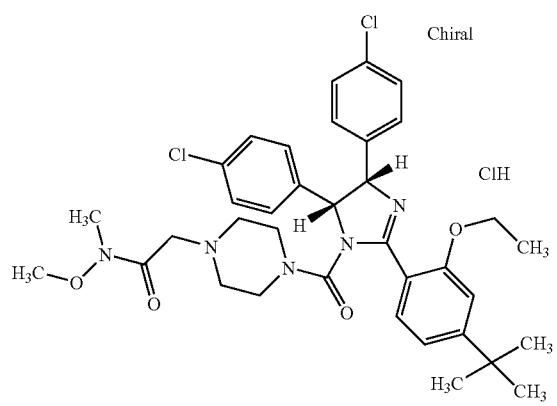

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-N-methoxy-N-methyl-acetamide hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and N-methoxy-N-methyl-2-piperazin-1-yl-acetamide (example 16b) in an analogous manner as described in example 25. LR-MS: 680.5 [(M+H)⁺]

Example 91

4-{(4S,5R)-4,5-Bis-(4-chloro-phenyl)-2-[2-ethoxy-4-(2-hydroxy-1,1-dimethyl-ethyl)-phenyl]-4,5-dihydro-imidazole-1-carbonyl}-piperazin-2-one was prepared from (4S,5R)-4,5-bis-(4-chloro-phenyl)-2-[2-ethoxy-4-(2-hydroxy-1,1-dimethyl-ethyl)-phenyl]-4,5-dihydro-imidazole-1-carbonyl chloride (example 12g) and 2-piperazinone (Avocado Organics) in an analogous manner as described in example 25. LR-MS: 609.4 [(M+H)⁺]

Example 92

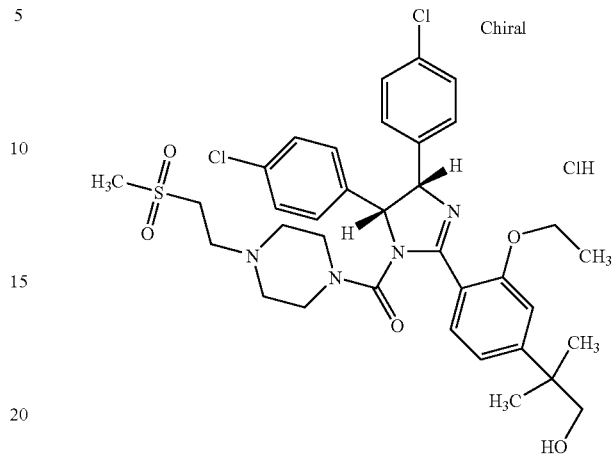

{(4S,5R)-4,5-Bis-(4-chloro-phenyl)-2-[2-ethoxy-4-(2-hydroxy-1,1-dimethyl-ethyl)-phenyl]-4,5-dihydro-imidazol-1-yl}-[4-(2-methanesulfonyl-ethyl)-piperazin-1-yl]-methanone hydrochloride was prepared from (4S,5R)-4,5-bis-(4-chloro-phenyl)-2-[2-ethoxy-4-(2-hydroxy-1,1-dimethyl-ethyl)-phenyl]-4,5-dihydro-imidazole-1-carbonyl chloride (example 12g) and 1-(2-methanesulfonylethyl)piperazine dihydrochloride (example 17) in an analogous manner as described in example 25. LR-MS: 701.4 [(M+H)⁺]

Example 93

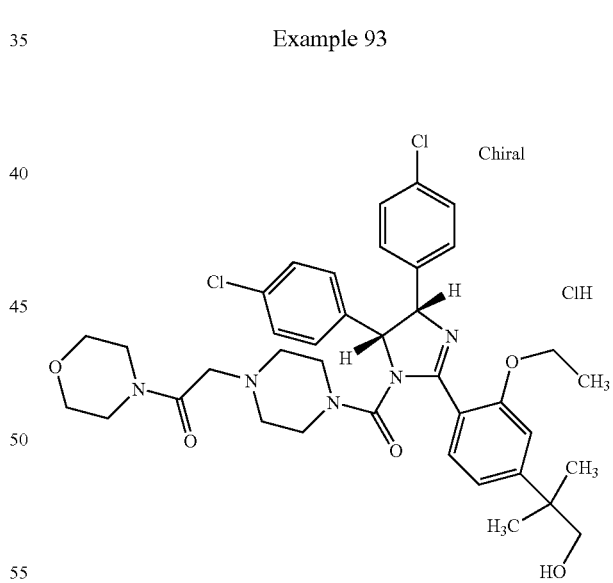

2-(4-{(4S,5R)-4,5-Bis-(4-chloro-phenyl)-2-[2-ethoxy-4-(2-hydroxy-1,1-dimethyl-ethyl)-phenyl]-4,5-dihydro-imidazole-1-carbonyl}-piperazin-1-yl)-1-morpholin-4-yl-ethanone hydrochloride was prepared from (4S,5R)-4,5-bis-(4-chloro-phenyl)-2-[2-ethoxy-4-(2-hydroxy-1,1-dimethyl-ethyl)-phenyl]-4,5-dihydro-imidazole-1-carbonyl chloride (example 12g) and 1-morpholin-4-yl-2-piperazin-1-yl-ethanone (Oakwood Products) in an analogous manner as described in example 25. LR-MS: 722.5 [(M+H)⁺]

Example 94

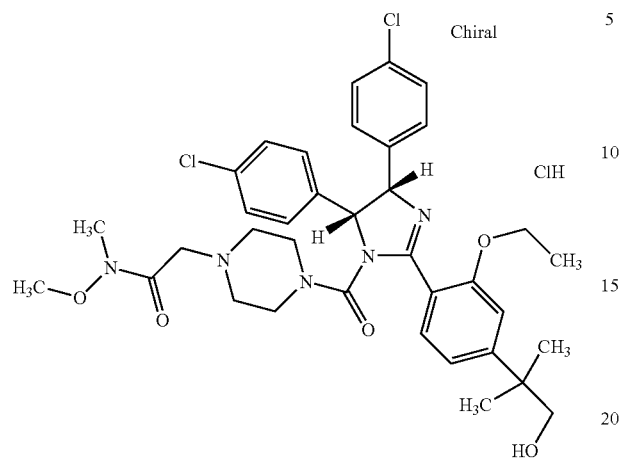

2-(4-{(4S,5R)-4,5-Bis-(4-chloro-phenyl)-2-[2-ethoxy-4-(2-hydroxy-1,1-dimethyl-ethyl)-phenyl]-4,5-dihydro-imidazole-1-carbonyl}-piperazin-1-yl)-N-methoxy-N-methyl-acetamide hydrochloride was prepared from (4S,5R)-4,5-bis-(4-chloro-phenyl)-2-[2-ethoxy-4-(2-hydroxy-1,1-dimethyl-ethyl)-phenyl]-4,5-dihydro-imidazole-1-carbonyl chloride (example 12g) and N-methoxy-N-methyl-2-piperazin-1-yl-acetamide (example 16b) in an analogous manner as described in example 25. LR-MS: 696.5 [(M+H)$^+$]

Example 95

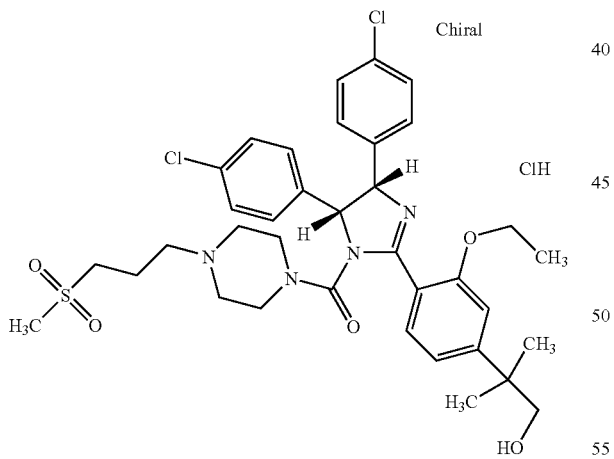

{(4S,5R)-4,5-Bis-(4-chloro-phenyl)-2-[2-ethoxy-4-(2-hydroxy-1,1-dimethyl-ethyl)-phenyl]-4,5-dihydro-imidazol-1-yl}-[4-(3-methanesulfonyl-propyl)-piperazin-1-yl]-methanone hydrochloride was prepared from (4S,5R)-4,5-bis-(4-chloro-phenyl)-2-[2-ethoxy-4-(2-hydroxy-1,1-dimethyl-ethyl)-phenyl]-4,5-dihydro-imidazole-1-carbonyl chloride (example 12g) and 1-(3-methanesulfonyl-propyl)-piperazine (example 16e) in an analogous manner as described in example 25. LR-MS: 715.4 [(M+H)$^+$]

Example 96

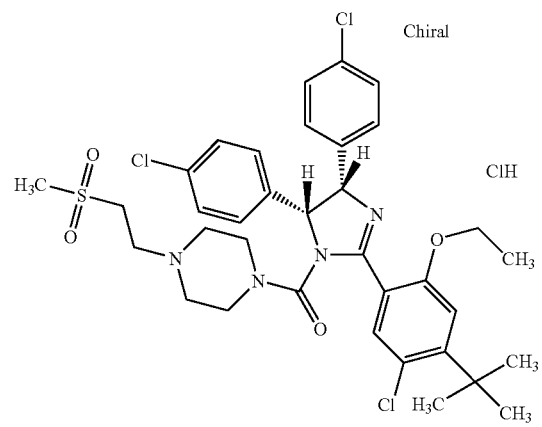

[(4S,5R)-2-(4-tert-Butyl-5-chloro-2-ethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and 1-(2-methanesulfonylethyl)piperazine dihydrochloride (example 17) in an analogous manner as described in example 25. LR-MS: 721.4 [(M+H)$^+$]

Example 97

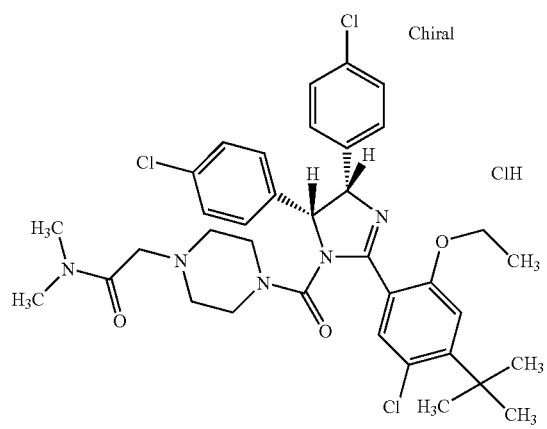

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-N,N-dimethyl-acetamide hydrochloride was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and N,N-dimethyl-2-piperazin-1-yl-acetamide (Oakwood Products) in an analogous manner as described in example 25. LR-MS: 698.4 [(M+H)$^+$]

Example 98

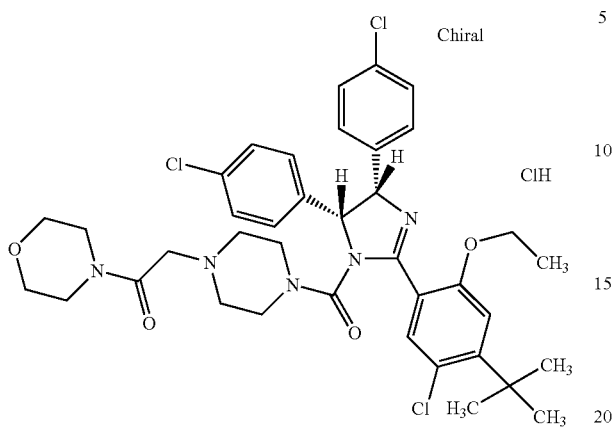

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and 1-morpholin-4-yl-2-piperazin-1-yl-ethanone (Oakwood Products) in an analogous manner as described in example 25. LR-MS: 742.4 [(M+H)$^+$]

Example 99

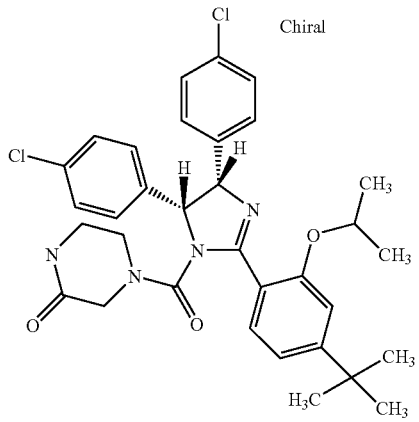

4-[(4S,5R)-2-(4-tert-Butyl-2-isopropoxy-phenyl)-4,5-bis-(4-chloro-phenyl)-4,5-dihydro-imidazole-1-carbonyl]-piperazin-2-one was prepared from (4S,5R)-2-(4-tert-butyl-2-isopropoxy-phenyl)-4,5-bis-(4-chloro-phenyl)-4,5-dihydro-imidazole-1-carbonyl chloride (example 12i) and 2-piperazinone (Avocado Organics) in an analogous manner as described in example 25. LR-MS: 607.4 [(M+H)$^+$]

Example 100

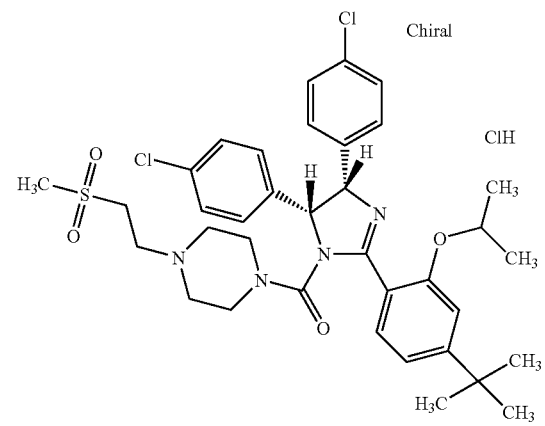

[(4S,5R)-2-(4-tert-Butyl-2-isopropoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride was prepared from (4S,5R)-2-(4-tert-butyl-2-isopropoxy-phenyl)-4,5-bis-(4-chloro-phenyl)-4,5-dihydro-imidazole-1-carbonyl chloride (example 12i) and 1-(2-methanesulfonylethyl)piperazine dihydrochloride (example 17) in an analogous manner as described in example 25. LR-MS: 699.4 [(M+H)$^+$]

Example 101

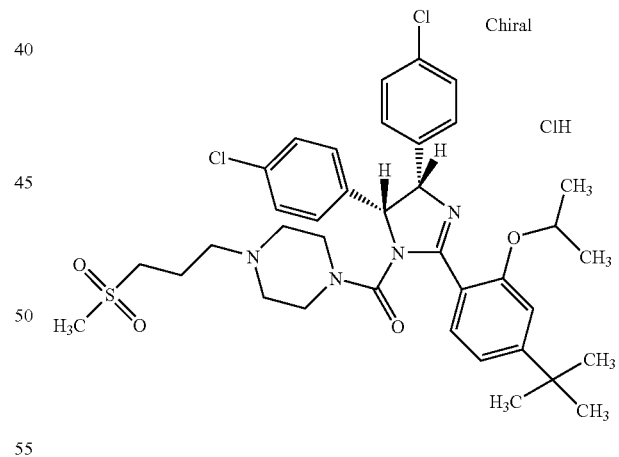

[(4S,5R)-2-(4-tert-Butyl-2-isopropoxy-phenyl)-4,5-bis-(4-chloro-phenyl)-4,5-dihydro-imidazol-1-yl]-[4-(3-methanesulfonyl-propyl)-piperazin-1-yl]-methanone hydrochloride was prepared from (4S,5R)-2-(4-tert-butyl-2-isopropoxy-phenyl)-4,5-bis-(4-chloro-phenyl)-4,5-dihydro-imidazole-1-carbonyl chloride (example 12i) and 1-(3-methanesulfonyl-propyl)-piperazine (example 16e) in an analogous manner as described in example 25. LR-MS: 713.4 [(M+H)$^+$]

Example 102

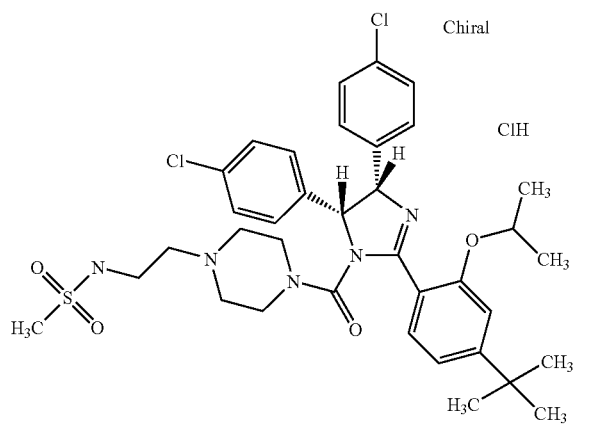

N-(2-{4-[(4S,5R)-2-(4-tert-Butyl-2-isopropoxy-phenyl)-4,5-bis-(4-chloro-phenyl)-4,5-dihydro-imidazole-1-carbonyl]-piperazin-1-yl}-ethyl)-methanesulfonamide hydrochloride was prepared from (4S,5R)-2-(4-tert-butyl-2-isopropoxy-phenyl)-4,5-bis-(4-chloro-phenyl)-4,5-dihydro-imidazole-1-carbonyl chloride (example 12i) and N-(2-methanosulfonylethyl)-piperazine hydrochloride (example 22) in an analogous manner as described in example 25. LR-MS: 714.4 [(M+H)$^+$]

Example 103

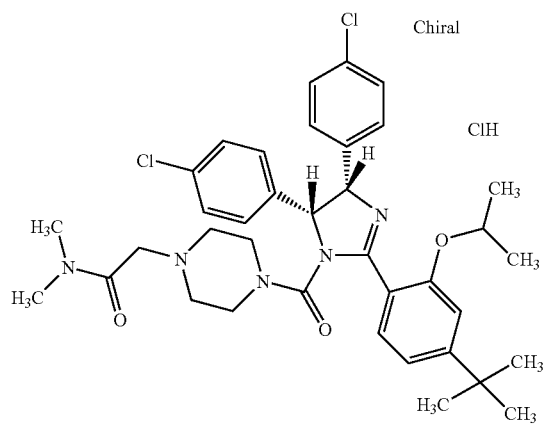

2-{4-[(4S,5R)-2-(4-tert-Butyl-2-isopropoxy-phenyl)-4,5-bis-(4-chloro-phenyl)-4,5-dihydro-imidazole-1-carbonyl]-piperazin-1-yl}-N,N-dimethyl-acetamide hydrochloride was prepared from (4S,5R)-2-(4-tert-butyl-2-isopropoxy-phenyl)-4,5-bis-(4-chloro-phenyl)-4,5-dihydro-imidazole-1-carbonyl chloride (example 12i) and N,N-dimethyl-2-piperazin-1-yl-acetamide (Oakwood Products) in an analogous manner as described in example 25. LR-MS: 678.5 [(M+H)$^+$]

Example 104

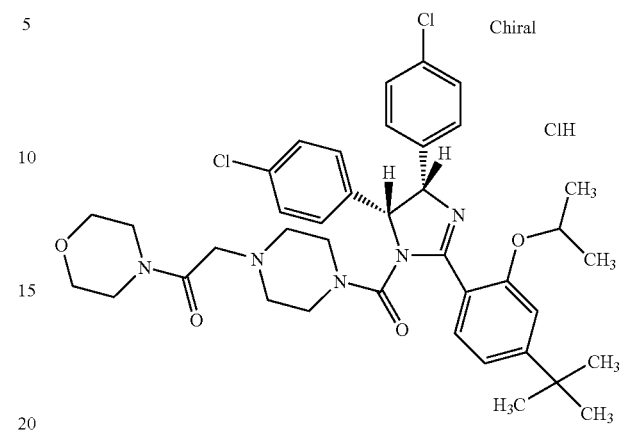

2-{4-[(4S,5R)-2-(4-tert-Butyl-2-isopropoxy-phenyl)-4,5-bis-(4-chloro-phenyl)-4,5-dihydro-imidazole-1-carbonyl]-piperazin-1-yl}-1-morpholin-4-yl-ethanone hydrochloride was prepared from (4S,5R)-2-(4-tert-butyl-2-isopropoxy-phenyl)-4,5-bis-(4-chloro-phenyl)-4,5-dihydro-imidazole-1-carbonyl chloride (example 12i) and 1-morpholin-4-yl-2-piperazin-1-yl-ethanone (Oakwood Products) in an analogous manner as described in example 25. LR-MS: 720.5 [(M+H)$^+$]

Example 105

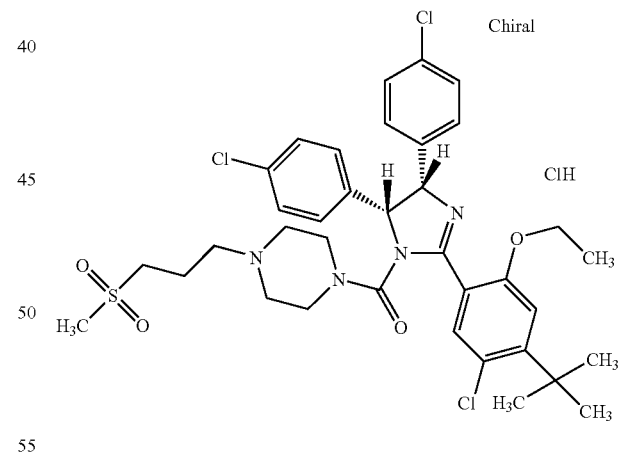

[(4S,5R)-2-(4-tert-Butyl-5-chloro-2-ethoxy-phenyl)-4,5-bis-(4-chloro-phenyl)-4,5-dihydro-imidazol-1-yl]-[4-(3-methanesulfonyl-propyl)-piperazin-1-yl]-methanone hydrochloride was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and 1-(3-methanesulfonyl-propyl)-piperazine (example 16e) in an analogous manner as described in example 25. LR-MS: 735.4 [(M+H)$^+$]

Example 106

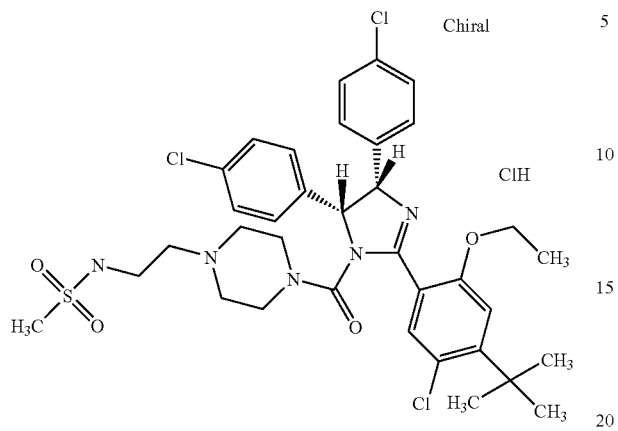

N-(2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-ethyl)-methanesulfonamide hydrochloride was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and N-(2-methanosulfonylethyl)-piperazine hydrochloride (example 22) in an analogous manner as described in example 25. LR-MS: 734.4 [(M+H)+]

Example 107

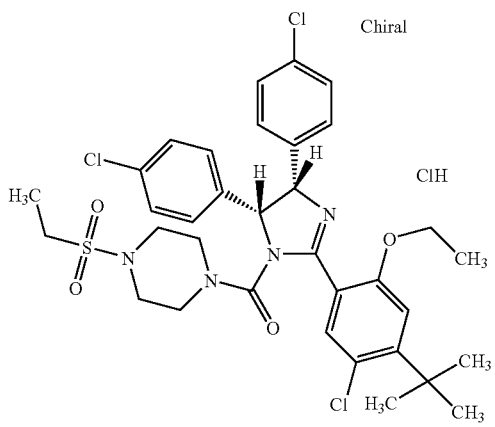

[(4S,5R)-2-(4-tert-Butyl-5-chloro-2-ethoxy-phenyl)-4,5-bis-(4-chloro-phenyl)-4,5-dihydro-imidazol-1-yl]-(4-ethanesulfonyl-piperazin-1-yl)-methanone hydrochloride was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and 1-ethanesulfonyl-piperazine (example 14) in an analogous manner as described in example 25. LR-MS: 707.4 [(M+H)+]

Example 108

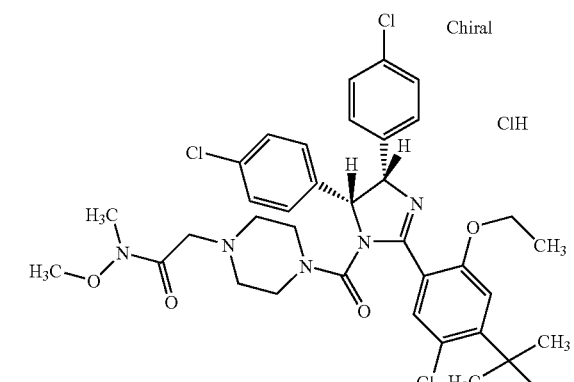

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-N-methoxy-N-methyl-acetamide hydrochloride was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and N-methoxy-N-methyl-2-piperazin-1-yl-acetamide (example 16b) in an analogous manner as described in example 25. LR-MS: 716.4 [(M+H)+]

Example 109

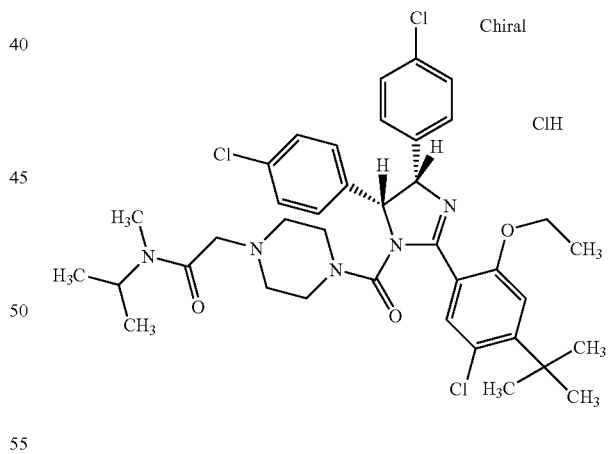

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-N-isopropyl-N-methyl-acetamide hydrochloride was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and N-isopropyl-N-methyl-2-piperazin-1-yl-acetamide (example 16c) in an analogous manner as described in example 25. LR-MS: 728.4 [(M+H)+]

Example 110

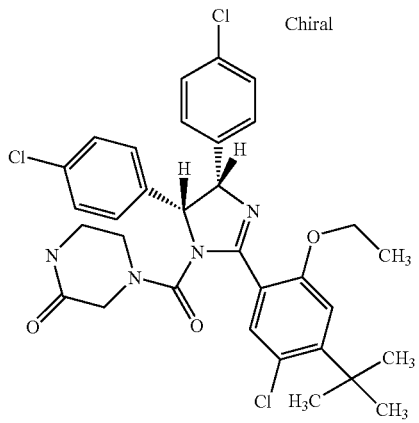

4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-2-one was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and 2-piperazinone (Avocado Organics) in an analogous manner as described in example 25. LR-MS: 629.3 [(M+H)$^+$]

Example 111

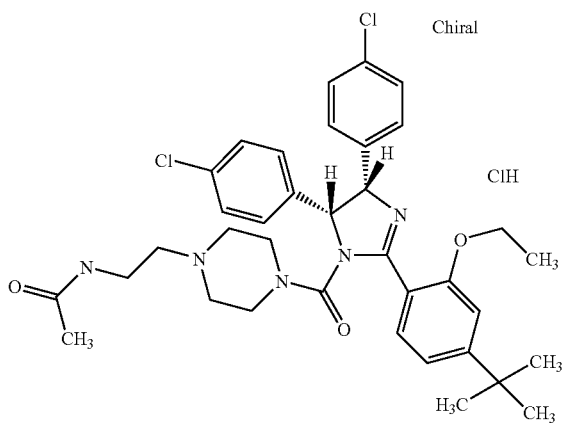

N-(2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-ethyl)-acetamide hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and N-(2-piperazin-1-yl-ethyl)-acetamide hydrochloride (example 23) in an analogous manner as described in example 25. LR-MS: 664.5 [(M+H)$^+$]

Example 112

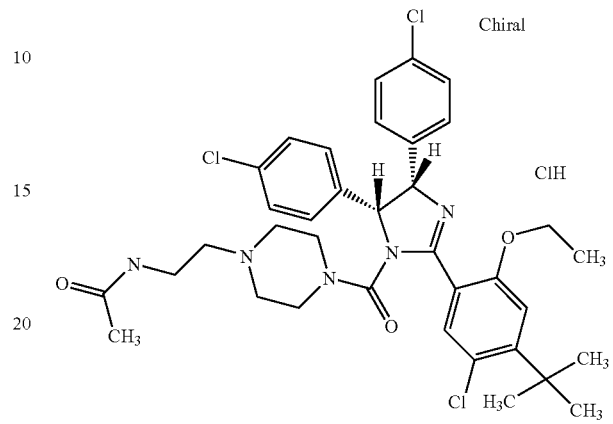

N-(2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-ethyl)-acetamide hydrochloride was prepared from (4S,5R)-2-(4-tert-butyl-5-chloro-2-ethoxy-phenyl)-4,5-bis-(4-chloro-phenyl)-4,5-dihydro-imidazole-1-carbonyl chloride (example 12h) and N-(2-piperazin-1-yl-ethyl)-acetamide hydrochloride (example 23) in an analogous manner as described in example 25. LR-MS: 700.4 [(M+H)$^+$]

Example 113

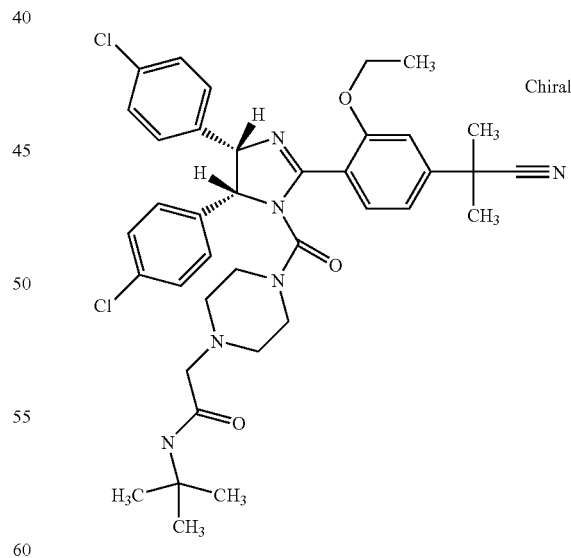

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-tert-butyl-acetamide was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and N-tert-butyl-2- piperazin-1-yl-acetamide (example 16g) in an analogous manner as described in example 25. LR-MS: 703.3 [(M+H)⁺]

Example 114

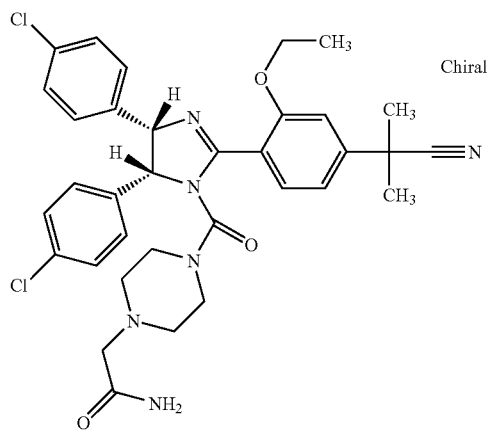

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-acetamide was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and 2-piperazin-1-yl-acetamide (Matrix) in an analogous manner as described in example 25. LR-MS: 647.3 [(M+H)⁺]

Example 115

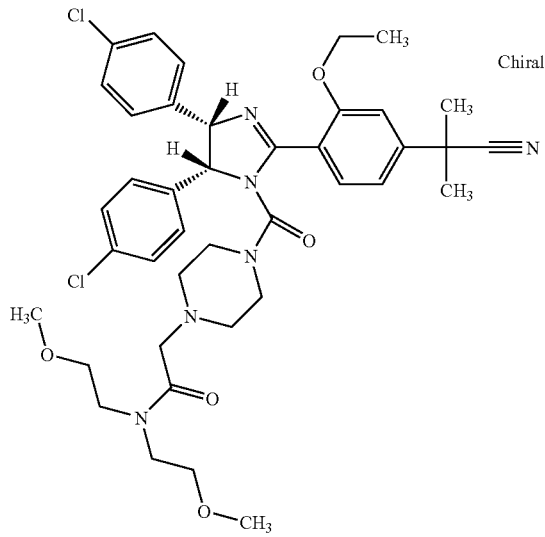

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N,N-bis-(2-methoxy-ethyl)-acetamide was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and N,N-bis-(2-methoxy-ethyl)-2-piperazin-1-yl-acetamide (example 16) in an analogous manner as described in example 25. LR-MS: 763.4 [(M+H)⁺]

Example 116

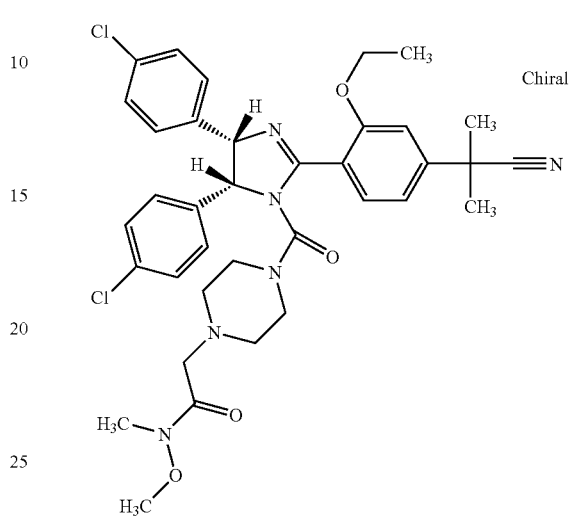

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-methoxy-N-methyl-acetamide was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and N-methoxy-N-methyl-2-piperazin-1-yl-acetamide (example 16b) in an analogous manner as described in example 25. LR-MS: 691.3 [(M+H)⁺]

Example 117

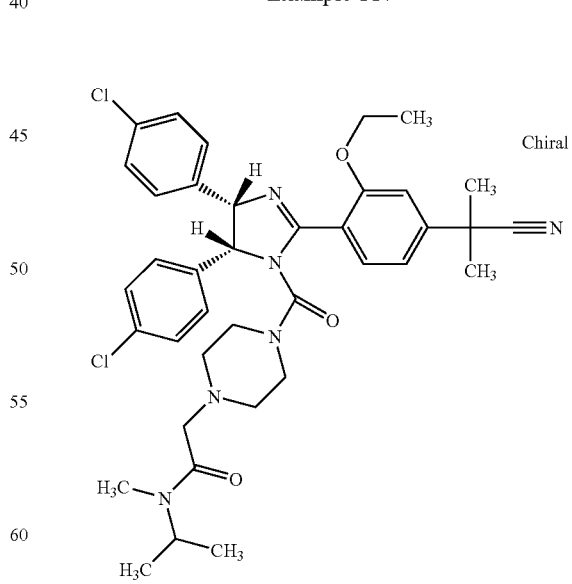

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-isopropyl-N-methyl-acetamide was prepared from (4S,5R)-4,5-bis-(4-chloro-phenyl)-

2-[4-(cyano-dimethyl-methyl)-2-ethoxy-phenyl]-4,5-dihydro-imidazole-1-carbonyl chloride (example 12j) and N-isopropyl-N-methyl-2-piperazin-1-yl-acetamide (example 16c) in an analogous manner as described in example 25. LR-MS: 703.4 [(M+H)$^+$]

Example 118

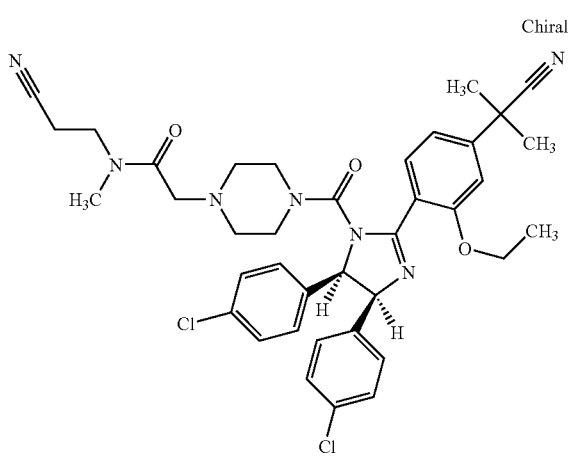

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-(2-cyano-ethyl)-N-methyl-acetamide was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and N-(2-cyano-ethyl)-N-methyl-2-piperazin-1-yl-acetamide (example 16d) in an analogous manner as described in example 25. LR-MS: 714.3 [(M+H)$^+$]

Example 119

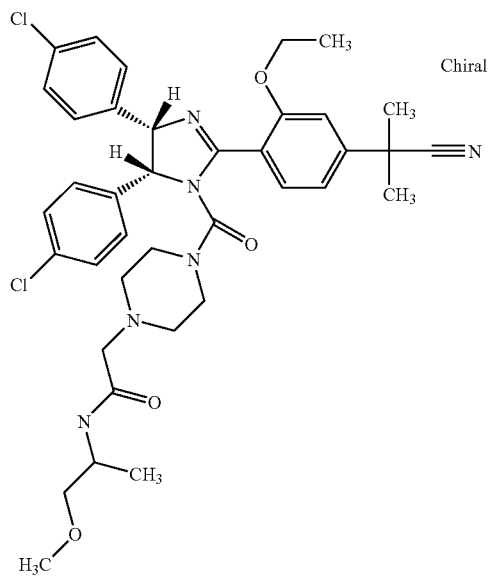

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-(2-methoxy-1-methyl-ethyl)-acetamide was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and N-(2-methoxy-1-methylethyl)-2-piperazin-1-yl-acetamide (example 15) in an analogous manner as described in example 25. LR-MS: 719.4 [(M+H)$^+$]

Example 120

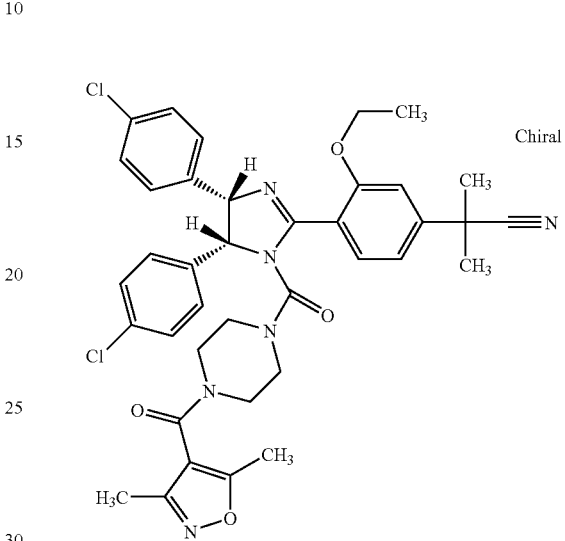

2-(4-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-3-ethoxy-phenyl)-2-methyl-propionitrile was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and (3,5-dimethyl-isoxazol-4-yl)-piperazin-1-yl-methanone (example 13) in an analogous manner as described in example 25. LR-MS: 713.3 [(M+H)$^+$]

Example 121

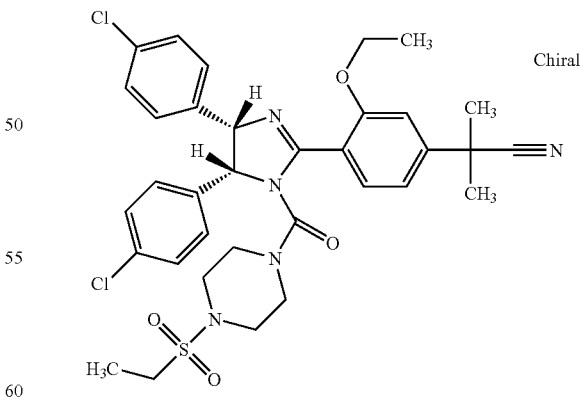

2-{4-[(4S,5R)-4,5-Bis-(4-chloro-phenyl)-1-(4-ethanesulfonyl-piperazine-1-carbonyl)-4,5-dihydro-1H-imidazol-2-yl]-3-ethoxy-phenyl}-2-methyl-propionitrile was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and 1-ethanesulfonyl-piperazine (example 14) in an analogous manner as described in example 25. LR-MS: 682.3 [(M+H)⁺]

Example 122

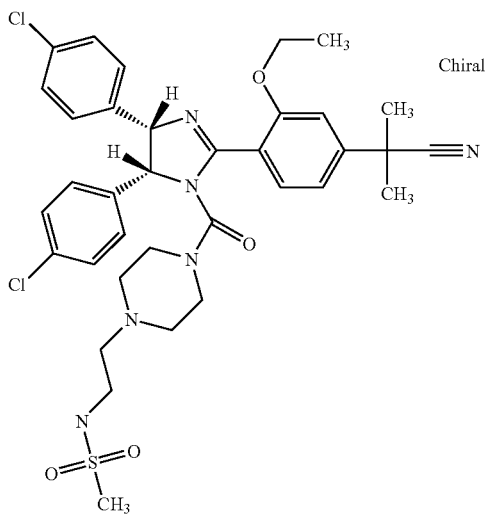

N-[2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-ethyl]-methanesulfonamide was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and N-(2-methanosulfonylethyl)-piperazine hydrochloride (example 22) in an analogous manner as described in example 25. LR-MS: 711.4 [(M+H)⁺]

Example 123

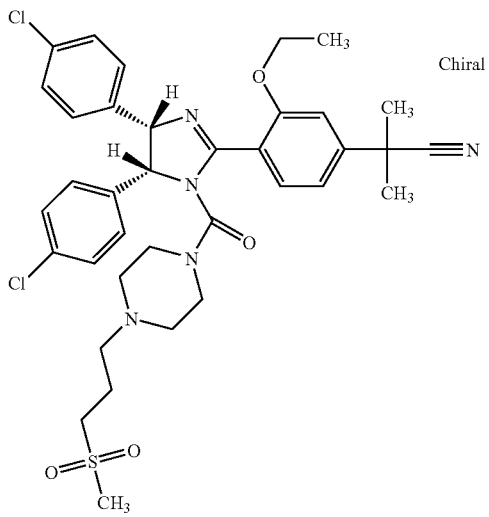

2-(4-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-3-ethoxy-phenyl)-2-methyl-propionitrile was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and 1-(3-methanesulfonyl-propyl)-piperazine (example 16e) in an analogous manner as described in example 25. LR-MS: 710.4 [(M+H)⁺]

Example 124

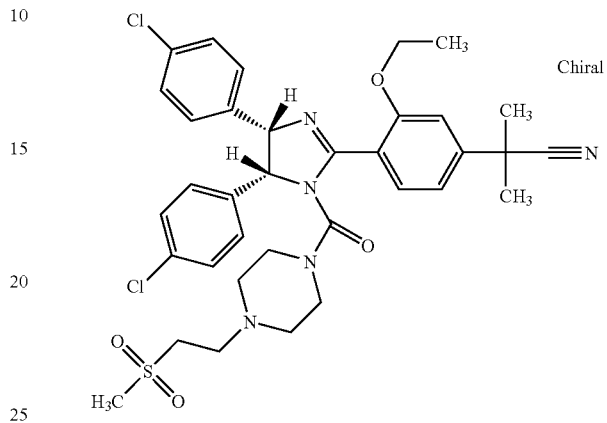

2-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-2-methyl-propionitrile was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and 1-(2-methanesulfonylethyl)piperazine dihydrochloride (example 17) in an analogous manner as described in example 25. LR-MS: 696.3 [(M+H)⁺]

Example 125

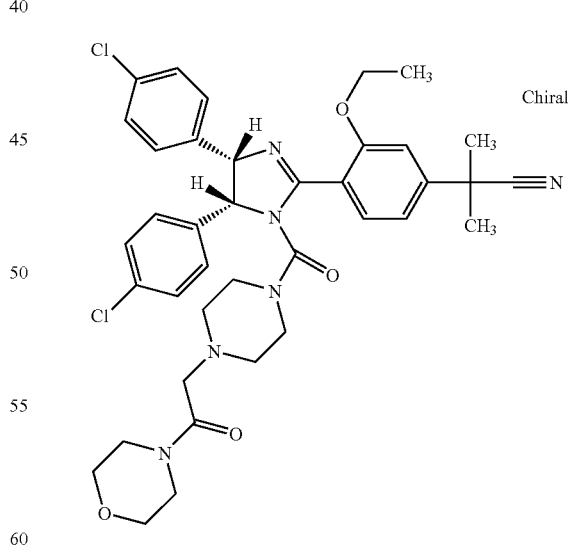

2-(4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-phenyl)-2-methyl-propionitrile was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and 1-morpholin-4-yl-2-piperazin-1-yl-ethanone (Oakwood Products) in an analogous manner as described in example 25. LR-MS: 717.3 [(M+H)+]

Example 126

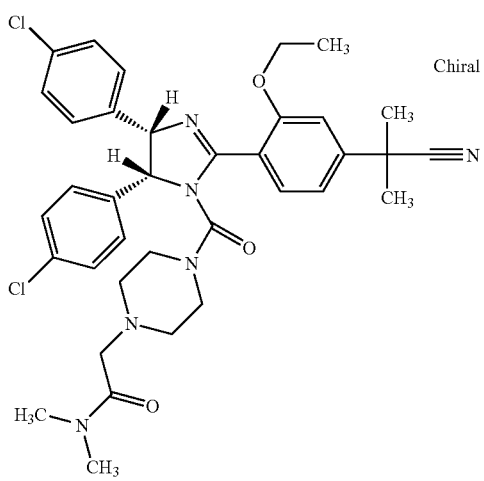

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N,N-dimethyl-acetamide was prepared from (4S,5R)-4,5-bis-(4-chloro-phenyl)-2-[4-(cyano-dimethyl-methyl)-2-ethoxy-phenyl]-4,5-dihydro-imidazole-1-carbonyl chloride (example 12j) and N,N-dimethyl-2-piperazin-1-yl-acetamide (Oakwood Products) in an analogous manner as described in example 25. LR-MS: 675.3 [(M+H)+]

Example 127

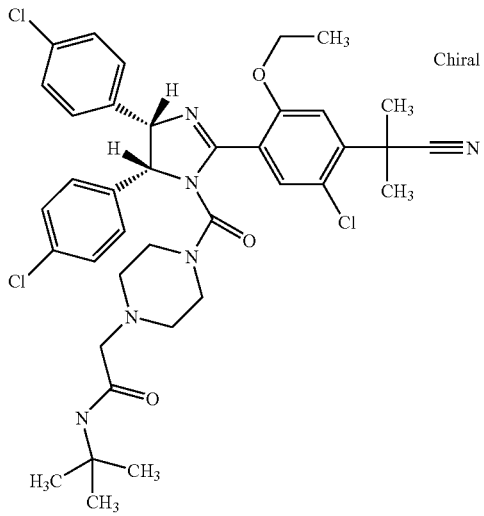

N-tert-Butyl-2-{4-[(4S,5R)-2-[5-chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-acetamide was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and N-tert-butyl-2-piperazin-1-yl-acetamide (example 16g) in an analogous manner as described in example 25. LR-MS: 737.4 [(M+H)+]

Example 128

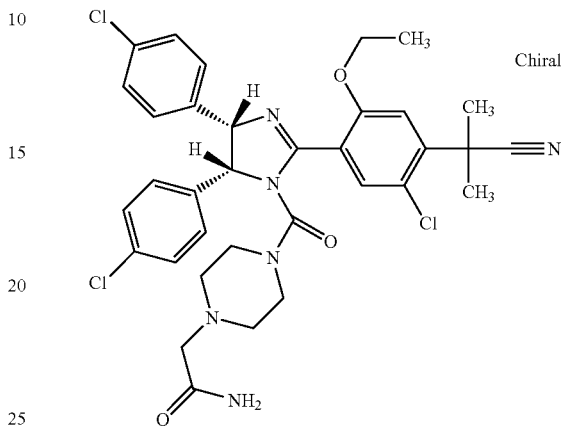

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-acetamide was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and 2-piperazin-1-yl-acetamide (Matrix) in an analogous manner as described in example 25. LR-MS: 681.2 [(M+H)+]

Example 129

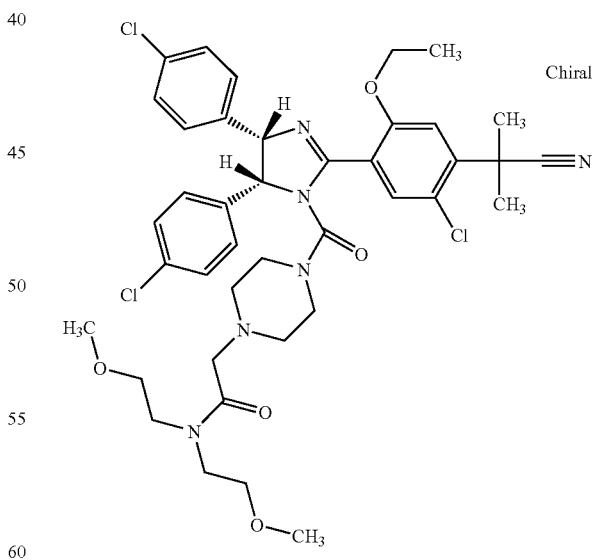

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N,N-bis-(2-methoxy-ethyl)-acetamide was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and N,N-bis-(2-methoxy-ethyl)-2-piperazin-1-yl-acetamide (example 16) in an analogous manner as described in example 25. LR-MS: 797.4 [(M+H)⁺]

Example 130

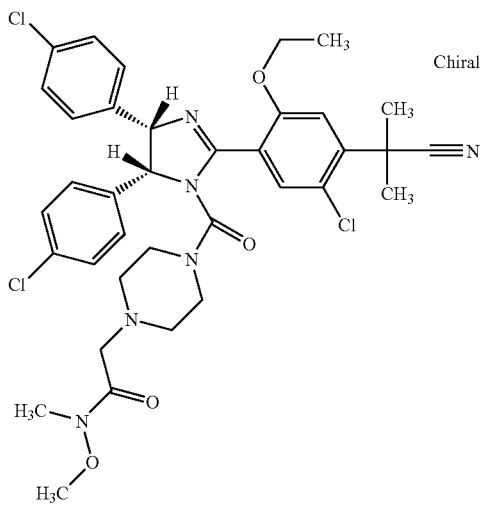

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-methoxy-N-methyl-acetamide was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and N-methoxy-N-methyl-2-piperazin-1-yl-acetamide (example 16b) in an analogous manner as described in example 25. LR-MS: 725.3 [(M+H)⁺]

Example 131

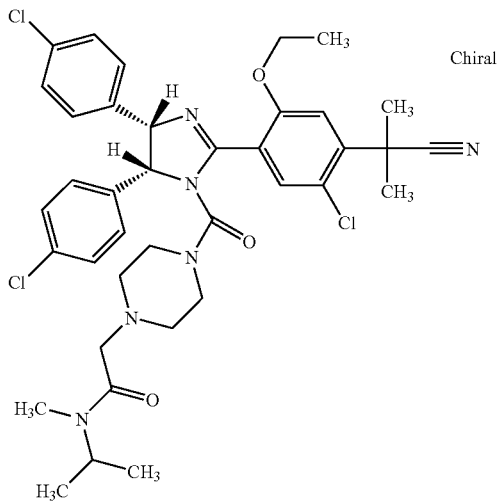

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-isopropyl-N-methyl-acetamide was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and N-isopropyl-N-methyl-2-piperazin-1-yl-acetamide (example 16c) in an analogous manner as described in example 25. LR-MS: 737.4 [(M+H)⁺]

Example 132

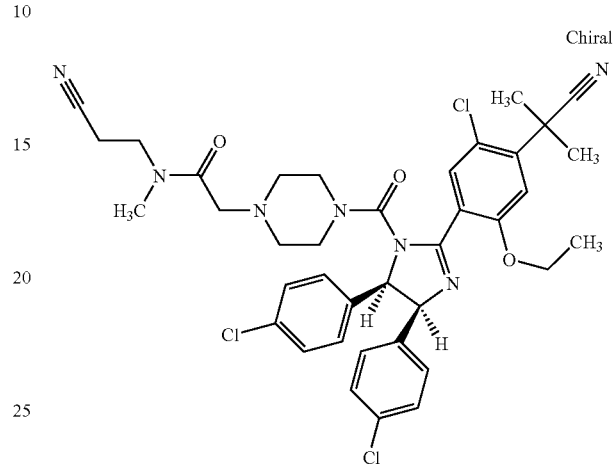

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-(2-cyano-ethyl)-N-methyl-acetamide was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and N-(2-cyano-ethyl)-N-methyl-2-piperazin-1-yl-acetamide (example 16d) in an analogous manner as described in example 25. LR-MS: 748.3 [(M+H)⁺]

Example 133

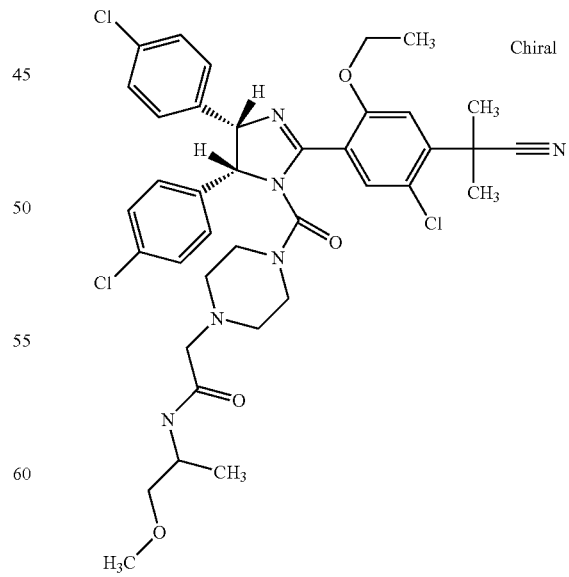

2-{4-[(4S,5R)-2-[5-Chloro-4-(cyano-dimethyl-methyl)-2-ethoxy-phenyl]-4,5-bis-(4-chloro-phenyl)-4,5-dihydroimidazole-1-carbonyl]-piperazin-1-yl}-N-(2-methoxy-1-methyl-ethyl)-acetamide was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and N-(2-methoxy-1-methylethyl)-2-piperazin-1-yl-acetamide (example 15) in an analogous manner as described in example 25. LR-MS: 753.4 [(M+H)+]

Example 134

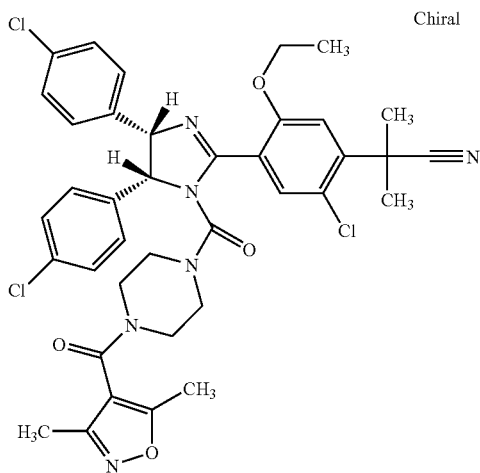

2-(4-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-2-chloro-5-ethoxy-phenyl)-2-methyl-propionitrile was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and (3,5-dimethyl-isoxazol-4-yl)-piperazin-1-yl-methanone (example 13) in an analogous manner as described in example 25. LR-MS: 747.3 [(M+H)+]

Example 135

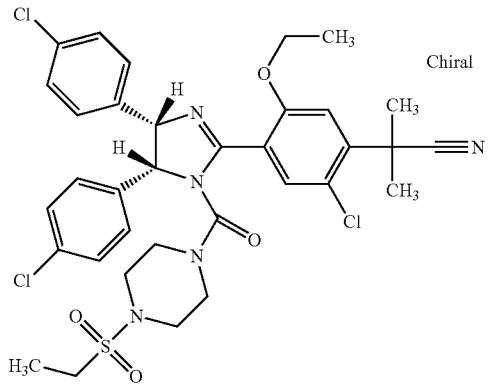

2-{4-[(4S,5R)-4,5-Bis-(4-chloro-phenyl)-1-(4-ethanesulfonyl-piperazine-1-carbonyl)-4,5-dihydro-1H-imidazol-2-yl]-2-chloro-5-ethoxy-phenyl}-2-methyl-propionitrile was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and 1-ethanesulfonyl-piperazine (example 14) in an analogous manner as described in example 25. LR-MS: 716.3 [(M+H)+]

Example 136

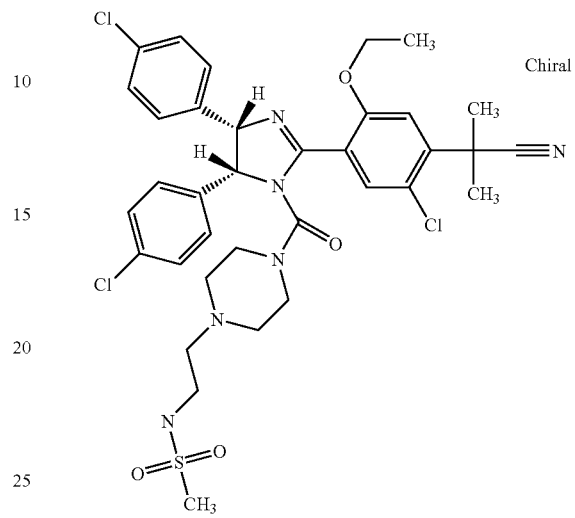

N-(2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-ethyl)-methanesulfonamide was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and N-(2-methanosulfonylethyl)-piperazine hydrochloride (example 22) in an analogous manner as described in example 25. LR-MS: 745.4 [(M+H)+]

Example 137

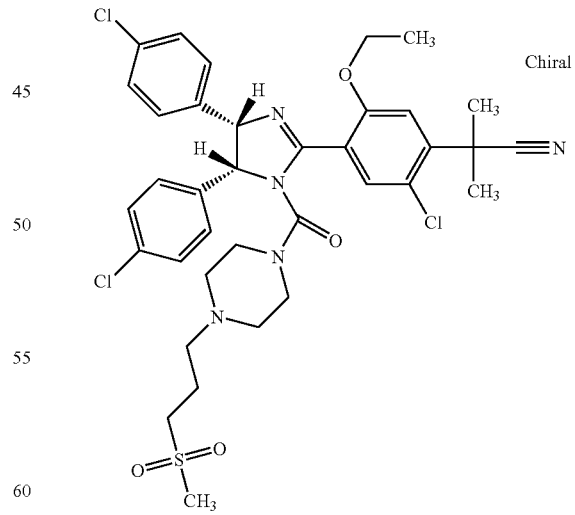

2-(4-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-2-chloro-5-ethoxy-phenyl)-2-methyl-propionitrile was prepared from (4S,5R)-2-[5-Chloro-4-(cyano-dimethyl-methyl)-2-ethoxy-phenyl]-4,5-bis-(4- chloro-phenyl)-4,5-dihydro-imidazole-1-carbonyl chloride (example 12k) and 1-(3-methanesulfonyl-propyl)-piperazine (example 16e) in an analogous manner as described in example 25. LR-MS: 744.4 [(M+H)⁺]

Example 138

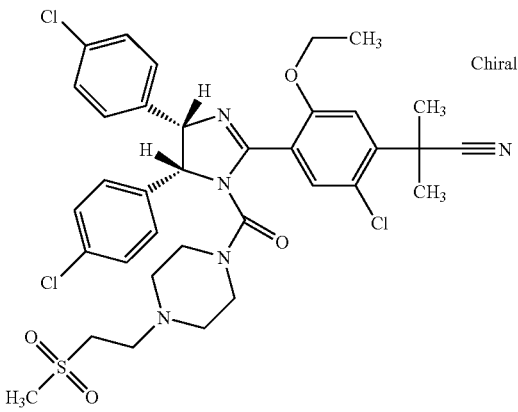

2-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-5-ethoxy-phenyl)-2-methyl-propionitrile was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and 1-(2-methanesulfonylethyl)piperazine dihydrochloride (example 17) in an analogous manner as described in example 25. LR-MS: 730.3 [(M+H)⁺]

Example 139

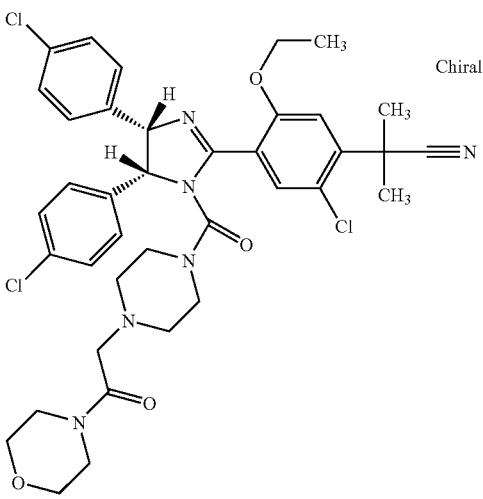

2-(4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-5-ethoxy-phenyl)-2-methyl-propionitrile was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and 1-morpholin-4-yl-2-piperazin-1-yl-ethanone (Oakwood Products) in an analogous manner as described in example 25. LR-MS: 751.3 [(M+H)⁺]

Example 140

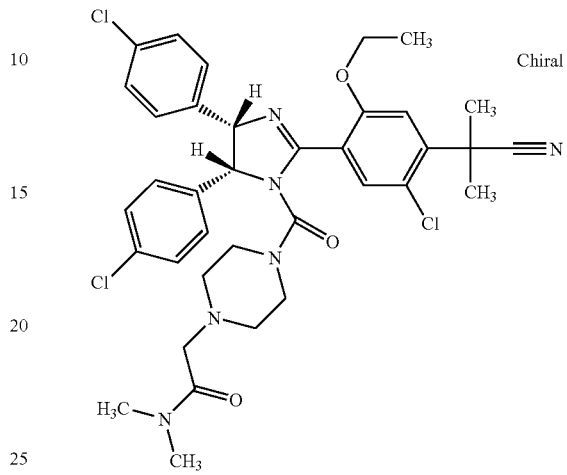

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N,N-dimethyl-acetamide was prepared from (4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl chloride (example 12k) and N,N-dimethyl-2-piperazin-1-yl-acetamide (Oakwood Products) in an analogous manner as described in example 25. LR-MS: 709.3 [(M+H)⁺]

Example 141

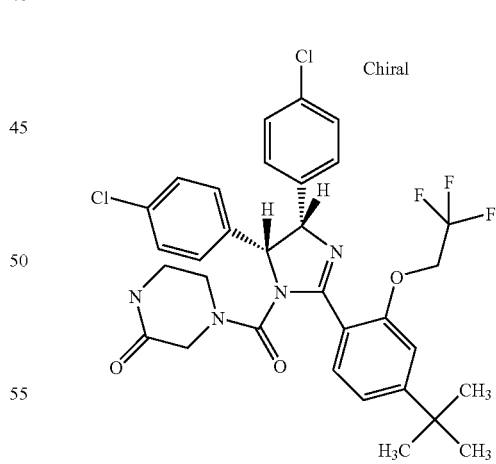

4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-2-one was prepared from (4S,5R)-2-[4-tert-butyl-2-(2,2,2-trifluoro-ethoxy)-phenyl]-4,5-bis-(4-chloro-phenyl)-4,5-dihydro-imidazole-1-carbonyl chloride (example 12l) and 2-piperazinone (Avocado Organics) in an analogous manner as described in example 25. LR-MS: 697.4 [(M+H)⁺]

Example 142

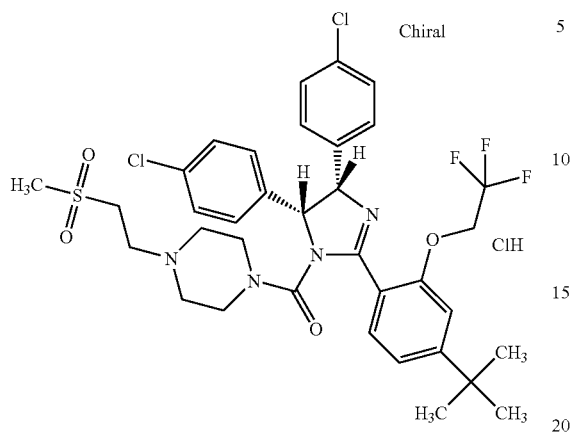

[(4S,5R)-2-[4-tert-Butyl-2-(2,2,2-trifluoro-ethoxy)-phenyl]-4,5-bis-(4-chloro-phenyl)-4,5-dihydro-imidazol-1-yl]-[4-(2-methanesulfonyl-ethyl)-piperazin-1-yl]-methanone hydrochloride was prepared from (4S,5R)-2-[4-tert-butyl-2-(2,2,2-trifluoro-ethoxy)-phenyl]-4,5-bis-(4-chloro-phenyl)-4,5-dihydro-imidazole-1-carbonyl chloride (example 12l) and 1-(2-methanesulfonylethyl)piperazine dihydrochloride (example 17) in an analogous manner as described in example 25. LR-MS: 739.4 [(M+H)$^+$]

Example 143

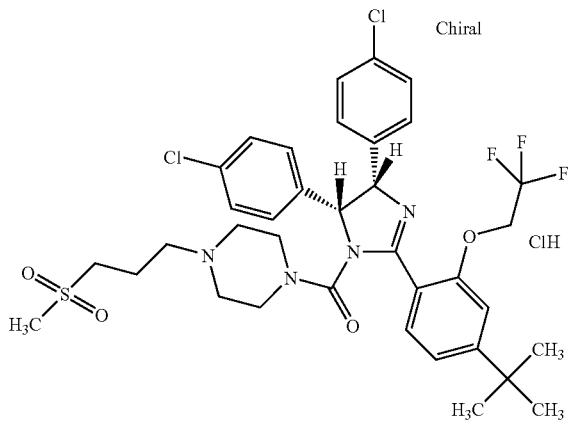

[(4S,5R)-2-[4-tert-Butyl-2-(2,2,2-trifluoro-ethoxy)-phenyl]-4,5-bis-(4-chloro-phenyl)-4,5-dihydro-imidazol-1-yl]-[4-(3-methanesulfonyl-propyl)-piperazin-1-yl]-methanone hydrochloride was prepared from (4S,5R)-2-[4-tert-butyl-2-(2,2,2-trifluoro-ethoxy)-phenyl]-4,5-bis-(4-chloro-phenyl)-4,5-dihydro-imidazole-1-carbonyl chloride (example 12l) and 1-(3-methanesulfonyl-propyl)-piperazine (example 16e) in an analogous manner as described in example 25. LR-MS: 753.4 [(M+H)$^+$]

Example 144

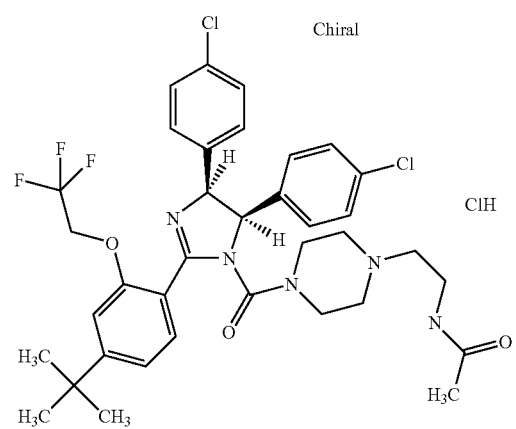

N-(2-{4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-1-yl}-ethyl)-acetamide hydrochloride was prepared from (4S,5R)-2-[4-tert-butyl-2-(2,2,2-trifluoro-ethoxy)-phenyl]-4,5-bis-(4-chloro-phenyl)-4,5-dihydro-imidazole-1-carbonyl chloride (example 12l) and N-(2-piperazin-1-yl-ethyl)-acetamide hydrochloride (example 23) in an analogous manner as described in example 25. LR-MS: 718.5 [(M+H)$^+$]

Example 145

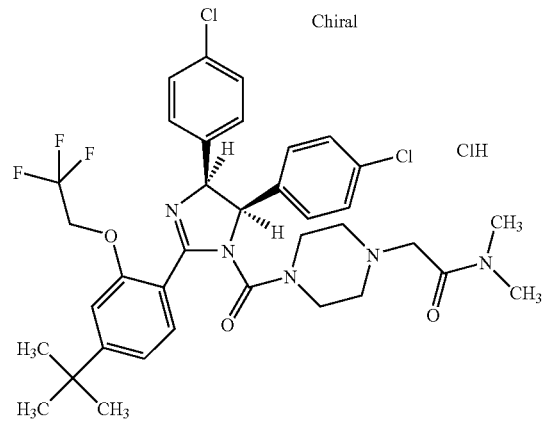

2-{4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-1-yl}-N,N-dimethyl-acetamide hydrochloride was prepared from (4S,5R)-2-[4-tert-butyl-2-(2,2,2-trifluoro-ethoxy)-phenyl]-4,5-bis-(4-chloro-phenyl)-4,5-dihydro-imidazole-1-carbonyl chloride (example 12l) and N,N-dimethyl-2-piperazin-1-yl-acetamide (Oakwood Products) in an analogous manner as described in example 25. LR-MS: 718.5 [(M+)$^+$]

Example 146

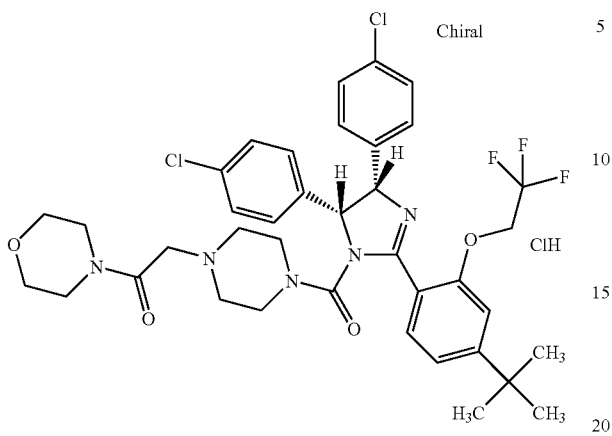

(4S,5R)-2-[4-tert-butyl-2-(2,2,2-trifluoro-ethoxy)-phenyl]-4,5-bis-(4-chloro-phenyl)-4,5-dihydro-imidazole-1-carbonyl]-piperazin-1-yl}-1-morpholin-4-yl-ethanone hydrochloride was prepared from (4S,5R)-2-[4-tert-butyl-2-(2,2,2-trifluoro-ethoxy)-phenyl]-4,5-bis-(4-chloro-phenyl)-4,5-dihydro-imidazole-1-carbonyl chloride (example 12l) and 1-morpholin-4-yl-2-piperazin-1-yl-ethanone (Oakwood Products) in an analogous manner as described in example 25. LR-MS: 760.5 [(M+H)+]

Example 147

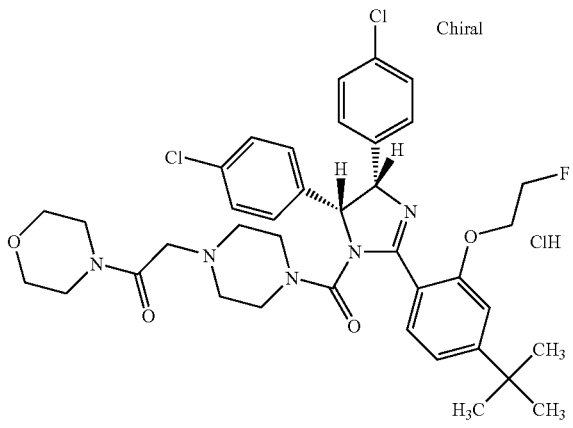

2-{4-[(4S,5R)-2-[4-tert-Butyl-2-(2-fluoro-ethoxy)-phenyl]-4,5-bis-(4-chloro-phenyl)-4,5-dihydro-imidazole-1-carbonyl]-piperazin-1-yl}-1-morpholin-4-yl-ethanone hydrochloride was prepared from (4S,5R)-2-[4-tert-butyl-2-(2-fluoro-ethoxy)-phenyl]-4,5-bis-(4-chloro-phenyl)-4,5-dihydro-imidazole-1-carbonyl chloride (example 12m) and 1-morpholin-4-yl-2-piperazin-1-yl-ethanone (Oakwood Products) in an analogous manner as described in example 25. LR-MS: 724.5 [(M+H)+]

Example 148

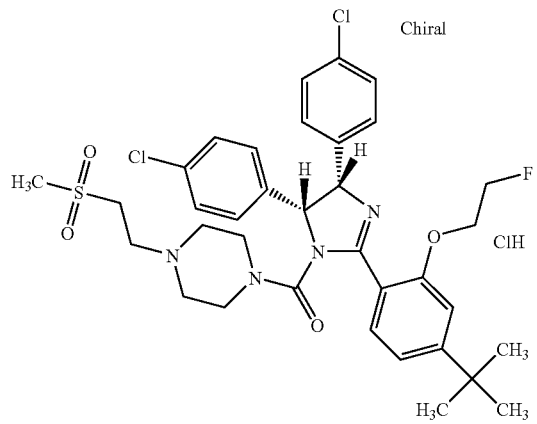

[(4S,5R)-2-[4-tert-Butyl-2-(2-fluoro-ethoxy)-phenyl]-4,5-bis-(4-chloro-phenyl)-4,5-dihydro-imidazol-1-yl]-[4-(2-methanesulfonyl-ethyl)-piperazin-1-yl]-methanone hydrochloride was prepared from (4S,5R)-2-[4-tert-butyl-2-(2-fluoro-ethoxy)-phenyl]-4,5-bis-(4-chloro-phenyl)-4,5-dihydro-imidazole-1-carbonyl chloride (example 12m) and 1-(2-methanesulfonylethyl)-piperazine dihydrochloride (example 17) in an analogous manner as described in example 25. LR-MS: 703.5 [(M+H)+]

Example 149

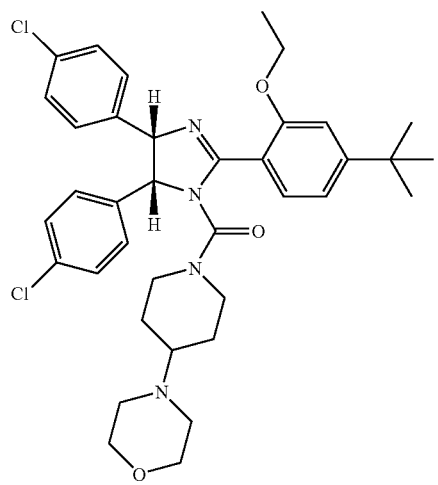

[(4S,5R)-2-(4-tert-Butyl-2-ethoxy-phenyl)-4,5-bis-(4-chloro-phenyl)-4,5-dihydro-imidazol-1-yl]-(4-morpholin-4-yl-piperidin-1-yl)-methanone was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 4-morpholinopiperidine (Aldrich) in an analogous manner as described in example 25. HR-MS (ES, m/z): observed 663.2859, calculated for $C_{37}H_{45}Cl_2N_4O_3$ [(M+H)+] 663.2863.

Example 150

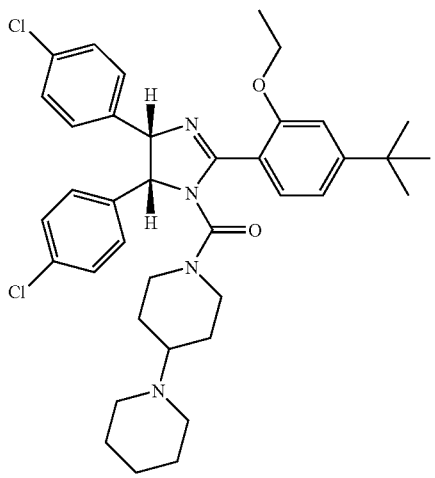

[1,4']Bipiperidinyl-1'-yl-[(4S,5R)-2-(4-tert-butyl-2-ethoxy-phenyl)-4,5-bis-(4-chloro-phenyl)-4,5-dihydro-imidazol-1-yl]-methanone was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 4-piperidinopiperidine (Aldrich) in an analogous manner as described in example 25. HR-MS (ES, m/z): observed 661.3071, calculated for $C_{38}H_{47}Cl_2N_4O_3$ $[(M+H)^+]$ 661.3071.

Example 151

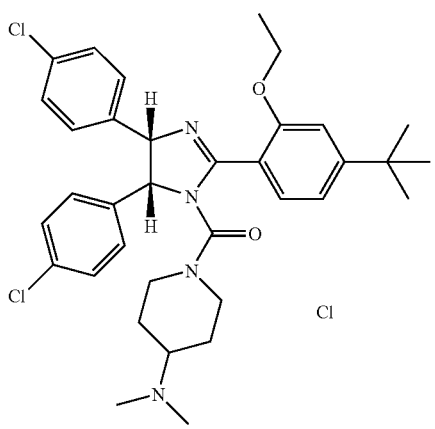

[2-(4-tert-Butyl-2-ethoxy-phenyl)-4,5-bis-(4-chloro-phenyl)-4,5-dihydro-imidazol-1-yl]-(4-dimethylamino-piperidin-1-yl)-methanone hydrochloride was prepared from (4S,5R)-2-(4-tert-butyl-2-ethoxy-phenyl)-4,5-bis-(4-chloro-phenyl)-4,5-dihydro-imidazole-1-carbonyl chloride (example 11) and 4-dimethylaminopiperidine (Aldrich) in an analogous manner as described in example 25. HR-MS (ES, m/z): observed 621.2755 calculated for $C_{35}H_{42}Cl_2N_4O_2$ $[(M+H)^+]$ 621.2758.

Example 152

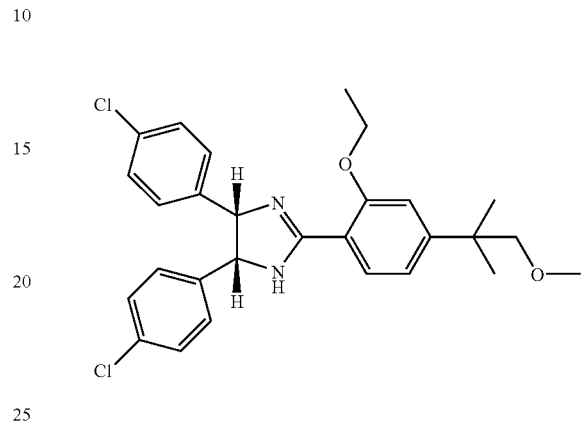

4,5-Bis-(4-chloro-phenyl)-2-[2-ethoxy-4-(2-methoxy-1,1-dimethyl-ethyl)-phenyl]-4,5-dihydro-1H-imidazole To a solution of 2-ethoxy-4-(2-hydroxy-1,1-dimethylethyl)iodobenzene (1.0 g, 3.123 mmol, example 4) in tetrahydrofuran cooled to 0° C. was added sodium hydride (150 mg, 6.246 mmol, 60% in mineral oil). Iodomethane (0.58 mL, 9.369 mmol) was added after 15 min. The icebath was then removed and the reaction mixture was stirred at room temperature for 12 h. Saturated solution of ammonium chloride was added and the mixture was partitioned between ethyl acetate (20 mL) and water (5 mL). The product was extracted with ethyl acetate (2×). The organic layers were washed with water (1×), brine (1×), dried over anhydrous sodium sulfate and concentrated. Purification of the crude residue by flash column chromatography (silica gel, eluting with a gradient of 0-60% ethyl acetate in hexanes) gave 2-ethoxy-4-(2-methoxy-1,1-dimethylethyl)iodobenzene (891 mg, 85% yield) as clear oil.

Using the analogous procedure as described in example 4, 2-ethoxy-4-(2-methoxy-1,1-dimethylethyl)iodobenzene (891 mg, 2.666 mmol) was converted to 2-ethoxy-4-(2-methoxy-1,1-dimethylethyl)-benzoic acid methyl ester (510 mg, 72% yield) as yellow oil.

Using the analogous procedure as described in example 9, 2-ethoxy-4-(2-methoxy-1,1-dimethylethyl)-benzoic acid methyl ester (483 mg, 1.814 mmol) was reacted with meso-1,2-bis-(4-chlorophenyl)-ethane-1,2-diamine (510 mg, 1.814 mmol) in the presence of trimethylaluminum (907 uL, 1.814 mmol, 2M solution in toluene) to give 4,5-bis-(4-chloro-phenyl)-2-[2-ethoxy-4-(2-methoxy-1,1-dimethyl-ethyl)-phenyl]-4,5-dihydro-1H-imidazole (581 mg, 64% yield) as pale yellow oil. LR-MS: 497.2 $[(M+H)^+]$.

Example 153

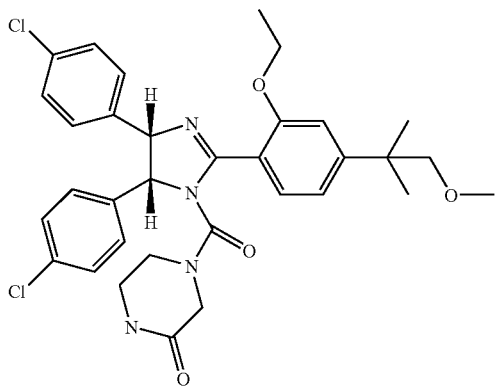

4-{(4S,5R)-4,5-Bis-(4-chloro-phenyl)-2-[2-ethoxy-4-(2-methoxy-1,1-dimethyl-ethyl)-phenyl]-4,5-dihydro-imidazole-1-carbonyl}-piperazin-2-one 4,5-bis-(4-chloro-phenyl)-2-[2-ethoxy-4-(2-methoxy-1,1-dimethyl-ethyl)-phenyl]-4,5-dihydro-1H-imidazole (580 mg, 1.166 mmol) was reacted with phosgene (725 uL, 1.399 mmol, 20% solution in toluene) using the procedure as described in example 12 to give 4,5-bis-(4-chloro-phenyl)-2-[2-ethoxy-4-(2-methoxy-1,1-dimethyl-ethyl)-phenyl]-4,5-dihydro-imidazole-1-carbonyl chloride (370 mg, 57% yield) as white solids.

4,5-Bis-(4-chloro-phenyl)-2-[2-ethoxy-4-(2-methoxy-1,1-dimethyl-ethyl)-phenyl]-4,5-dihydro-imidazole-1-carbonyl chloride (60 mg, 0.107 mmol) was reacted with 2-piperazinone (16.1 mg, 0.161 mmol) using the procedure as described in example 25 to give 4,5-bis-(4-chloro-phenyl)-2-[2-ethoxy-4-(2-methoxy-1,1-dimethyl-ethyl)-phenyl]-4,5-dihydro-imidazole-1-carbonyl}-piperazin-2-one (64.7 mg) as white solids. The enantiomers were separated by chiral chromatography (Diacel ChiralPak OD, eluting with 40/60 hexane/ethanol). The first peak coming off the column is the desired 4-{(4S,5R)-4,5-bis-(4-chloro-phenyl)-2-[2-ethoxy-4-(2-methoxy-1,1-dimethyl-ethyl)-phenyl]-4,5-dihydro-imidazole-1-carbonyl}-piperazin-2-one (26.6 mg, white solids). HR-MS (ES, m/z): observed 623.2189, calculated for $C_{33}H_{37}Cl_2N_4O_4$ $[(M+H)^+]$ 623.2187.

Example 154

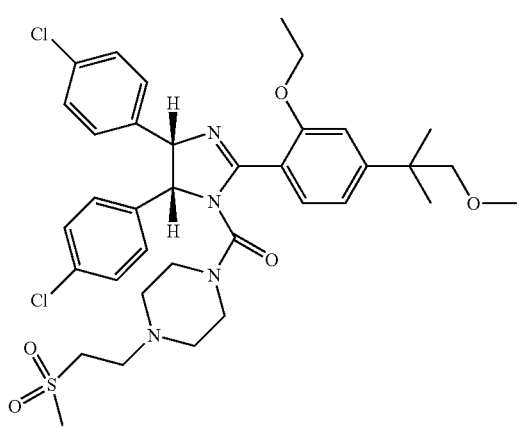

{(4S,5R)-4,5-Bis-(4-chloro-phenyl)-2-[2-ethoxy-4-(2-methoxy-1,1-dimethyl-ethyl)-phenyl]-4,5-dihydro-imidazol-1-yl}-[4-(2-methanesulfonyl-ethyl)-piperazin-1-yl]-methanone 4,5-Bis-(4-chloro-phenyl)-2-[2-ethoxy-4-(2-methoxy-1,1-dimethyl-ethyl)-phenyl]-4,5-dihydro-imidazole-1-carbonyl chloride (60 mg, 0.107 mmol, example 153) was reacted with 1-(2-methanesulfonyl-ethyl)piperazine dihydrochloride (42.5 mg, 0.161 mmol, example 17) using the procedure described in example 25 to give 4,5-bis-(4-chloro-phenyl)-2-[2-ethoxy-4-(2-methoxy-1,1-dimethyl-ethyl)-phenyl]-4,5-dihydro-imidazol-1-yl}-[4-(2-methanesulfonyl-ethyl)-piperazin-1-yl]-methanone (70.8 mg) as white solids. The enantiomers were separated by chiral chromatography (Diacel ChiralPak OD, eluting with 40/60 hexane/ethanol). The first peak coming off the column is the desired {(4S,5R)-4,5-bis-(4-chloro-phenyl)-2-[2-ethoxy-4-(2-methoxy-1,1-dimethyl-ethyl)-phenyl]-4,5-dihydro-imidazol-1-yl}-[4-(2-methanesulfonyl-ethyl)-piperazin-1-yl]-methanone (32.1 mg, white solids). HR-MS (ES, m/z): observed 715.2485, calculated for $C_{36}H_{45}Cl_2N_4O_5S$ $[(M+H)^+]$ 715.2482.

Example 155

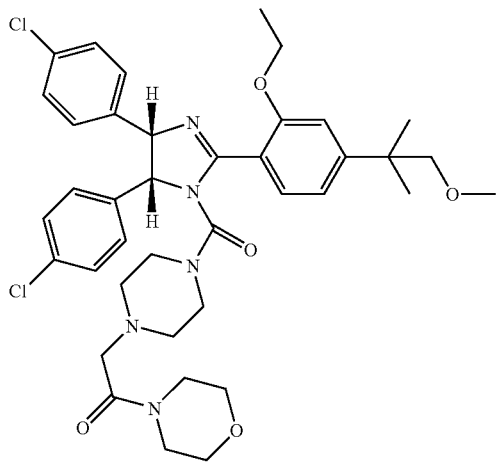

2-(4-{(4S,5R)-4,5-Bis-(4-chloro-phenyl)-2-[2-ethoxy-4-(2-methoxy-1,1-dimethyl-ethyl)-phenyl]-4,5-dihydro-imidazole-1-carbonyl}-piperazin-1-yl)-1-morpholin-4-yl-ethanone 4,5-Bis-(4-chloro-phenyl)-2-[2-ethoxy-4-(2-methoxy-1,1-dimethyl-ethyl)-phenyl]-4,5-dihydro-imidazole-1-carbonyl chloride (60 mg, 0.107 mmol) was reacted with 1-morpholin-4-yl-2-piperazin-1-yl-ethanone (34.2 mg, 0.161 mmol, Oakwood Products) using the procedure described in example 25 to give 4,5-bis-(4-chloro-phenyl)-2-[2-ethoxy-4-(2-methoxy-1,1-dimethyl-ethyl)-phenyl]-4,5-dihydro-imidazole-1-carbonyl}-piperazin-1-yl)-1-morpholin-4-yl-ethanone (70.1 mg) as white solids. The enantiomers were separated by chiral chromatography (Diacel ChiralPak OD, eluting with 40/60 hexane/ethanol). The first peak coming off the column is the desired 2-(4-{(4S,5R)-4,5-bis-(4-chloro-phenyl)-2-[2-ethoxy-4-(2-methoxy-1,1-dimethyl-ethyl)-phenyl]-4,5-dihydro-imidazole-1-carbonyl}-piperazin-1-yl)-1-morpholin-4-yl-ethanone (31.6 mg, white solids). HR-MS (ES, m/z): observed 736.3029, calculated for $C_{39}H_{48}Cl_2N_5O_5$ [(M+H)$^+$] 736.3027.

Example 156

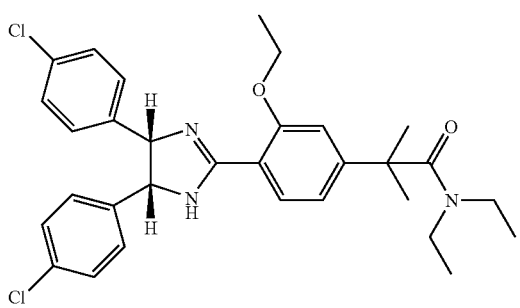

2-{4-[4,5-Bis-(4-chloro-phenyl)-4,5-dihydro-1H-imidazol-2-yl]-3-ethoxy-phenyl}-N,N-diethyl-isobutyramide A solution of 2-(4-iodo-3-methoxy-phenyl)-2-methyl-propionic acid (326 mg, 0.976 mmol, prepared by saponification of ethyl dimethyl-(3-ethoxy-4-iodophenyl)acetate, example 4) in thionyl chloride (5 mL) was heated at reflux for 1 h. It was concentrated to dryness then taken in 5 mL of tetrahydrofuran. Diethylamine (1 mL, 2 mmol, 2M solution in tetrahydrofuran) was added. The reaction mixture was stirred at room temperature overnight. It was diluted with ethyl acetate, washed with brine (1×), dried over anhydrous sodium sulfate and concentrated. Purification of the crude residue by flash column chromatography (silica gel, IntelliFlash 280, eluting with a gradient of 5-95% ethyl acetate in hexanes) gave N,N-diethyl-2-(4-iodo-3-methoxy-phenyl)-isobutyramide (361.4 mg, 95%) as clear oil.

Using the analogous procedure as described in example 4, N,N-diethyl-2-(4-iodo-3-methoxy-phenyl)-isobutyramide (361 mg, 0.927 mmol) was converted to 4-(1-diethylcarbamoyl-1-methyl-ethyl)-2-methoxy-benzoic acid methyl ester (166 mg, 56% yield) as yellow oil.

Using the analogous procedure as described in example 9, 4-(1-diethylcarbamoyl-1-methyl-ethyl)-2-methoxy-benzoic acid methyl ester (166 mg, 0.590 mmol) was reacted with meso-1,2-bis-(4-chlorophenyl)-ethane-1,2-diamine (510 mg, 1.814 mmol) in the presence of trimethylaluminum (295 uL, 0.590 mmol, 2M solution in toluene) to give 2-{4-[4,5-bis-(4-chloro-phenyl)-4,5-dihydro-1H-imidazol-2-yl]-3-ethoxy-phenyl}-N,N-diethyl-isobutyramide (90 mg, 28% yield) as pale yellow glass. LR-MS: 552.2 [(M+H)$^+$].

Example 157

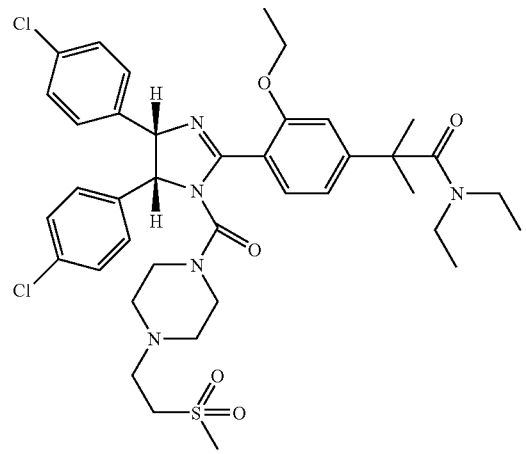

cis-2-(4-{4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-N,N-diethyl-isobutyramide 2-{4-[4,5-Bis-(4-chloro-phenyl)-4,5-dihydro-1H-imidazol-2-yl]-3-ethoxy-phenyl}-N,N-diethyl-isobutyramide (90 mg, 0.163 mmol) was reacted with phosgene (101 uL, 0.196 mmol, 20% solution in toluene) using the procedure as described in example 12 to give cis-4,5-bis-(4-chloro-phenyl)-2-[4-(1-diethylcarbamoyl-1-methyl-ethyl)-2-ethoxy-phenyl]-4,5-dihydro-imidazole-1-carbonyl chloride (56 mg, 56% yield) as white solids.

cis-4,5-Bis-(4-chloro-phenyl)-2-[4-(1-diethylcarbamoyl-1-methyl-ethyl)-2-ethoxy-phenyl]-4,5-dihydro-imidazole-1-carbonyl chloride (27 mg, 0.0439 mmol) was reacted with 1-(2-methanesulfonyl-ethyl)piperazine dihydrochloride (17.5 mg, 0.0659 mmol, example 17) using the procedure described in example 25 to give cis-2-(4-{4,5-bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-N,N-diethyl-isobutyramide (29.5 mg, 87% yield) as white solids. HR-MS (ES, m/z): observed 770.2909, calculated for $C_{39}H_{50}Cl_2N_5O_5S$ [(M+H)$^+$] 770.2904.

Example 158

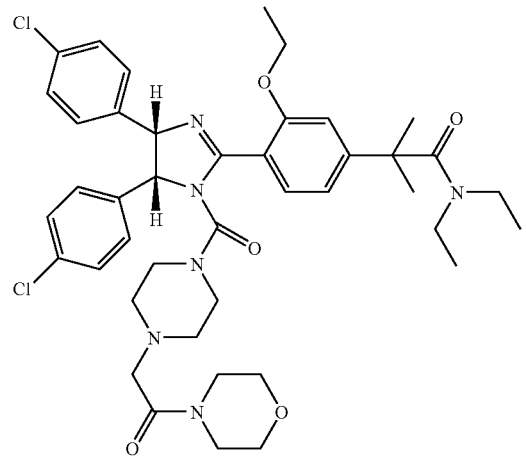

cis-2-(4-{4,5-Bis-(4-chloro-phenyl)-1-[4-(2-morpho-lin-4-yl-2-oxo-ethyl)-piperazine-1-carbonyl]-4,5-dihydro-1H-imidazol-2-yl}-3-ethoxy-phenyl)-N,N-diethyl-isobutyramide 4,5-Bis-(4-chloro-phenyl)-2-[4-(1-diethylcarbamoyl-1-methyl-ethyl)-2-ethoxy-phenyl]-4,5-dihydro-imidazole-1-carbonyl chloride (27 mg, 0.0439 mmol, example 157) was reacted with 1-morpholin-4-yl-2-piperazin-1-yl-ethanone (14 mg, 0.0659 mmol, Oakwood Products) using the procedure described in example 25 to give cis-2-(4-{4,5-bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-phenyl)-N,N-diethyl-isobutyramide (29.4 mg, 85% yield) as white solids. HR-MS (ES, m/z): observed 791.3445, calculated for $C_{42}H_{52}Cl_2N_6O_5$ [(M+H)$^+$] 791.3449.

Example 159

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL dilution compounds (1:5 dilution in reaction buffer) to each well, mix by shaking, Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

IC$_{50}$s showing biological activity that applies to compounds of the subject matter of this invention ranges from about 0.005 uM to about 2 uM. Specific data for some examples are as follows:

| Example | IC$_{50}$ (µM) |
|---------|----------------|
| 26      | 0.060          |
| 27      | 3.100          |
| 35      | 0.011          |
| 74      | 0.024          |

What is claimed:
1. A compound of the formula I

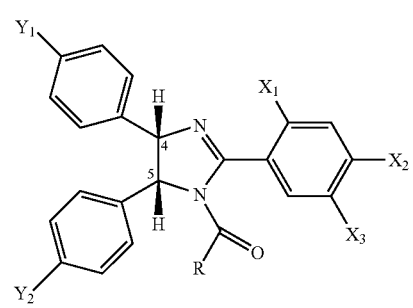

and the pharmaceutically acceptable salts and esters thereof, wherein
$X_1$ is selected from the group consisting of lower alkoxy, and lower alkoxy substituted by trifluoromethyl or fluorine;
$X_2$ is $C(X_4X_5)$—$X_6$;
$X_3$ is selected from the group consisting of hydrogen, lower alkoxy and halogen:
$X_4$ and $X_5$ are lower alkyl or together form a cycloalkyl;
$X_6$ is selected from the group consisting of lower alkyl, cyano, —CH$_2$—OH, —CH$_2$—O-lower alkyl, —CH$_2$—O-lower alkyl substituted by lower alkoxy, —C(O)X$_7$, and —CH$_2$—NX$_8$X$_9$;
$X_7$ is selected from the group consisting of hydroxy, lower alkoxy, morpholino, and —NX$_8$X$_9$;
$X_8$ and $X_9$ are independently selected from the group consisting of hydrogen, lower alkyl, lower alkyl substituted by lower alkoxy or cyano, and lower alkoxy;
$Y_1$ and $Y_2$ are independently selected from the group consisting of halogen, cyano, and acetylene;
R is

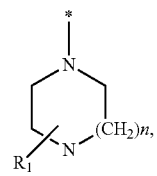

wherein
n=1 or 2,
$R_1$ is lower alkyl substituted by $R_2$;
$R_2$ is selected from the group consisting of lower alkoxy, trifluoromethyl, -cyano, —NH—SO$_2$-lower alkyl, —NH—C(O)-lower alkyl, —C(O)R$_4$, —C(O)—NX$_8$X$_9$, —SO$_2$-lower alkyl and —SO$_2$—NX$_8$X$_9$;
and
$R_4$ is selected from the group consisting of hydroxy, lower alkoxy, morpholino, and —NX$_8$X$_9$
and wherein the absolute stereochemistry at the 4 and 5 position of the imidazoline ring is S and R respectively.
2. The compound of claim 1 wherein the two hydrogen of the imidazoline ring are in the cis configuration to each other.
3. The compound of claim 1 wherein $Y_1$ and $Y_2$ are selected from —Cl or —Br.
4. The compound of claim 3 wherein $X_1$ is selected from ethoxy, isopropoxy, —OCH$_2$CF$_3$ or —OCH$_2$CH$_2$F.

5. The compound of claim 4 wherein $X_2$ is —C($X_4X_5$)—$X_6$ wherein $X_6$ is methyl, cyano or $CH_2OH$.

6. The compound of claim 5 wherein $X_3$ is hydrogen.

7. The compound of claim 6 wherein R is piperazinyl substituted by lower alkyl substituted by $R_2$ wherein $R_2$ is $SO_2$-lower alkyl or —C(O)$R_4$.

8. A compound selected from the group consisting of

2-{4-[(4S,5R)-2-(4-tert-Butyl-2-ethoxy-phenyl)-4,5-bis-(4-fluoro-phenyl)-4,5-dihydro-imidazole-1-carbonyl]-piperazin-1-yl}-1-morpholin-4-yl-ethanone hydrochloride;

2-{4-[(4S,5R)-2-(4-tert-Butyl-2-ethoxy-phenyl)-4,5-bis-(4-fluoro-phenyl)-4,5-dihydro-imidazole-1-carbonyl]-piperazin-1-yl}-N,N-dimethyl-acetamide hydrochloride;

[(4S,5R)-4,5-Bis-(4-bromo-phenyl)-2-(4-tert-butyl-2-ethoxy-phenyl)-4,5-dihydro-imidazol-1-yl]-[4-(2-methanesulfonyl-ethyl)-piperazin-1-yl]-methanone hydrochloride;

2-{4-[(4S,5R)-4,5-Bis-(4-bromo-phenyl)-2-(4-tert-butyl-2-ethoxy-phenyl)-4,5-dihydro-imidazole-1-carbonyl]-piperazin-1-yl}-1-morpholin-4-yl-ethanone hydrochloride;

[(4S,5R)-2-(4-tert-Butyl-2-ethoxy-phenyl)-4,5-bis-(4-ethynyl-phenyl)-4,5-dihydro-imidazol-1-yl]-[4-(2-methanesulfonyl-ethyl)-piperazin-1-yl]-methanone hydrochloride;

2-{4-[(4S,5R)-2-(4-tert-Butyl-2-ethoxy-phenyl)-4,5-bis-(4-ethynyl-phenyl)-4,5-dihydro-imidazole-1-carbonyl]-piperazin-1-yl}-1-morpholin-4-yl-ethanone hydrochloride;

[(4S,5R)-2-(4-tert-Butyl-2-ethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-N,N-dimethyl-acetamide hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride;

[(4S,5R)-2-(4-tert-Butyl-2,5-diethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride;

2-{4-[(4S,5R)-2-(4-tert-Butyl-2,5-diethoxy-phenyl)-4,5-bis-(4-chloro-phenyl)-4,5-dihydro-imidazole-1-carbonyl]-piperazin-1-yl}-N,N-dimethyl-acetamide hydrochloride;

[(4S,5R)-2-(4-tert-Butyl-2-ethoxy-phenyl)-4,5-bis-(4-chloro-phenyl)-4,5-dihydro-imidazol-1-yl]-[4-(2-methoxy-ethyl)-piperazin-1-yl]-methanone hydrochloride;

[(4S,5R)-2-(4-tert-Butyl-2-ethoxy-phenyl)-4,5-bis-(4-chloro-phenyl)-4,5-dihydro-imidazol-1-yl]-[4-(2-hydroxy-ethyl)-piperazin-1-yl]-methanone hydrochloride;

[(4S,5R)-2-(4-tert-Butyl-2-ethoxy-phenyl)-4,5-bis-(4-chloro-phenyl)-4,5-dihydro-imidazol-1-yl]-[4-(2-hydroxy-2-methyl-propyl)-piperazin-1-yl]-methanone hydrochloride;

[(4S,5R)-2-(4-tert-Butyl-2-ethoxy-phenyl)-4,5-bis-(4-chloro-phenyl)-4,5-dihydro-imidazol-1-yl]-[4-(3,3,3-trifluoro-2-hydroxy-propyl)-piperazin-1-yl]-methanone hydrochloride;

4-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-butan-2-one hydrochloride;

3-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-propionic acid hydrochloride;

3-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-propionitrile hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-acetamide hydrochloride;

N-tert-Butyl-2-{4-[(4S,5R)-2-(4-tert-butyl-2-ethoxy-phenyl)-4,5-bis-(4-chloro-phenyl)-4,5-dihydro-imidazole-1-carbonyl]-piperazin-1-yl}-acetamide hydrochloride;

{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-acetonitrile hydrochloride;

[(4S,5R)-2-(4-tert-Butyl-2-ethoxy-phenyl)-4,5-bis-(4-chloro-phenyl)-4,5-dihydro-imidazol-1-yl]-[4-(2,2,2-trifluoro-ethyl)-piperazin-1-yl]-methanone hydrochloride;

[(4S,5R)-2-(4-tert-Butyl-2-ethoxy-phenyl)-4,5-bis-(4-chloro-phenyl)-4,5-dihydro-imidazol-1-yl]-[4-(3,3,3-trifluoro-propyl)-piperazin-1-yl]-methanone hydrochloride;

4-[(4S,5R)-2-(4-tert-Butyl-2-ethoxy-phenyl)-4,5-bis-(4-chloro-phenyl)-4,5-dihydro-imidazole-1-carbonyl]-1-(2-methanesulfonyl-ethyl)-piperazin-2-one;

1-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-3,3-dimethyl-butan-2-one hydrochloride;

[(4S,5R)-2-(4-tert-Butyl-2-ethoxy-phenyl)-4,5-bis-(4-chloro-phenyl)-4,5-dihydro-imidazol-1-yl]-[4-(3-methanesulfonyl-propyl)-piperazin-1-yl]-methanone hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-[1,4]diazepan-1-yl}-1-morpholin-4-yl-ethanone hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-[1,4]diazepan-1-yl}-N,N-dimethyl-acetamide hydrochloride;

[(4S,5R)-2-(4-tert-Butyl-2-ethoxy-phenyl)-4,5-bis-(4-chloro-phenyl)-4,5-dihydro-imidazol-1-yl]-[4-(2-methanesulfonyl-ethyl)-[1,4]diazepan-1-yl]-methanone hydrochloride;

N-(2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-ethyl)-methanesulfonamide hydrochloride;

2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-N-methoxy-N-methyl-acetamide hydrochloride;

{(4S,5R)-4,5-Bis-(4-chloro-phenyl)-2-[2-ethoxy-4-(2-hydroxy-1,1-dimethyl-ethyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-4-(2-hydroxy-1,1-dimethyl-ethyl)-phenyl]-4,5-dihydro-imidazole-1-carbonyl}-piperazin-1-yl)-1-morpholin-4-yl-ethanone hydrochloride;

2-(4-{(4S,5R)-4,5-Bis-(4-chloro-phenyl)-2-[2-ethoxy-4-(2-hydroxy-1,1-dimethyl-ethyl)-phenyl]-4,5-dihydro-imidazole-1-carbonyl}-piperazin-1-yl)-N-methoxy-N-methyl-acetamide hydrochloride;

{(4S,5R)-4,5-Bis-(4-chloro-phenyl)-2-[2-ethoxy-4-(2-hydroxy-1,1-dimethyl-ethyl)-phenyl]-4,5-dihydro-imidazol-1-yl}-[4-(3-methanesulfonyl-propyl)-piperazin-1-yl]-methanone hydrochloride;

[(4S,5R)-2-(4-tert-Butyl-5-chloro-2-ethoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride;

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-N,N-dimethyl-acetamide hydrochloride;

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride;

[(4S,5R)-2-(4-tert-Butyl-2-isopropoxy-phenyl)-4,5-bis-(4-chloro-phenyl)-4,5-dihydro-imidazol-1-yl]-[4-(2-methanesulfonyl-ethyl)-piperazin-1-yl]-methanone hydrochloride;

[(4S,5R)-2-(4-tert-Butyl-2-isopropoxy-phenyl)-4,5-bis-(4-chloro-phenyl)-4,5-dihydro-imidazol-1-yl]-[4-(3-methanesulfonyl-propyl)-piperazin-1-yl]-methanone hydrochloride;

N-(2-{4-[(4S,5R)-2-(4-tert-Butyl-2-isopropoxy-phenyl)-4,5-bis-(4-chloro-phenyl)-4,5-dihydro-imidazole-1-carbonyl]-piperazin-1-yl}-ethyl)-methanesulfonamide hydrochloride;

2-{4-[(4S,5R)-2-(4-tert-Butyl-2-isopropoxy-phenyl)-4,5-bis-(4-chloro-phenyl)-4,5-dihydro-imidazole-1-carbonyl]-piperazin-1-yl}-N,N-dimethyl-acetamide hydrochloride;

2-{4-[(4S,5R)-2-(4-tert-Butyl-2-isopropoxy-phenyl)-4,5-bis-(4-chloro-phenyl)-4,5-dihydro-imidazole-1-carbonyl]-piperazin-1-yl}-1-morpholin-4-yl-ethanone hydrochloride;

[(4S,5R)-2-(4-tert-Butyl-5-chloro-2-ethoxy-phenyl)-4,5-bis-(4-chloro-phenyl)-4,5-dihydro-imidazol-1-yl]-[4-(3-methanesulfonyl-propyl)-piperazin-1-yl]-methanone hydrochloride;

N-(2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-ethyl)-methanesulfonamide hydrochloride;

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-N-methoxy-N-methyl-acetamide hydrochloride;

2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-N-isopropyl-N-methyl-acetamide hydrochloride;

N-(2-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-ethyl)-acetamide hydrochloride;

N-(2-{4-[(4S,5R)-2-(4-tert-Butyl-5-chloro-2-ethoxy-phenyl)-4,5-bis-(4-chloro-phenyl)-4,5-dihydro-imidazole-1-carbonyl]-piperazin-1-yl}-ethyl)-acetamide hydrochloride;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-tert-butyl-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N,N-bis-(2-methoxy-ethyl)-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N-(2-methoxy-1-methyl-ethyl)-acetamide;

N-[2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-ethyl]-methanesulfonamide;

2-(4-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-3-ethoxy-phenyl)-2-methyl-propionitrile;

2-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-2-methyl-propionitrile;

2-(4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-phenyl)-2-methyl-propionitrile;

2-(4-{(4S,5R)-4,5-Bis-(4-chloro-phenyl)-2-[4-(cyano-dimethyl-methyl)-2-ethoxy-phenyl]-4,5-dihydro-imidazole-1-carbonyl}-piperazin-1-yl)-N,N-dimethyl-acetamide;

N-tert-Butyl-2-{4-[(4S,5R)-2-[5-chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N,N-bis-(2-methoxy-ethyl)-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-methoxy-N-methyl-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-isopropyl-N-methyl-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-(2-cyano-ethyl)-N-methyl-acetamide;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N-(2-methoxy-1-methyl-ethyl)-acetamide;

N-(2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-ethyl)-methanesulfonamide;

2-(4-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-2-chloro-5-ethoxy-phenyl)-2-methyl-propionitrile;

2-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-5-ethoxy-phenyl)-2-methyl-propionitrile;

2-(4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-5-ethoxy-phenyl)-2-methyl-propionitrile;

2-{4-[(4S,5R)-2-[5-Chloro-4-(cyano-dimethyl-methyl)-2-ethoxy-phenyl]-4,5-bis-(4-chloro-phenyl)-4,5-dihydro-imidazole-1-carbonyl]-piperazin-1-yl}-N,N-dimethyl-acetamide;

[(4S,5R)-2-[4-tert-Butyl-2-(2,2,2-trifluoro-ethoxy)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;

[(4S,5R)-2-[4-tert-Butyl-2-(2,2,2-trifluoro-ethoxy)-phenyl]-4,5-bis-(4-chloro-phenyl)-4,5-dihydro-imidazol-1-yl]-[4-(3-methanesulfonyl-propyl)-piperazin-1-yl]-methanone hydrochloride;

N-(2-{4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-1-yl}-ethyl)-acetamide hydrochloride;

2-{4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-1-yl}-N,N-dimethyl-acetamide hydrochloride;

2-{4-[(4S,5R)-2-[4-tert-Butyl-2-(2,2,2-trifluoro-ethoxy)-phenyl]-4,5-bis-(4-chloro-phenyl)-4,5-dihydro-imidazole-1-carbonyl]-piperazin-1-yl}-1-morpholin-4-yl-ethanone hydrochloride;

2-{4-[(4S,5R)-2-[4-tert-Butyl-2-(2-fluoro-ethoxy)-phenyl]-4,5-bis-(4-chloro-phenyl)-4,5-dihydro-imidazole-1-carbonyl]-piperazin-1-yl}-1-morpholin-4-yl-ethanone hydrochloride;

[(4S,5R)-2-[4-tert-Butyl-2-(2-fluoro-ethoxy)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;

{(4S,5R)-4,5-Bis-(4-chloro-phenyl)-2-[2-ethoxy-4-(2-methoxy-1,1-dimethyl-ethyl)-phenyl]-4,5-dihydro-imidazol-1-yl}-[4-(2-methanesulfonyl-ethyl)-piperazin-1-yl]-methanone;

2-(4-{(4S,5R)-4,5-Bis-(4-chloro-phenyl)-2-[2-ethoxy-4-(2-methoxy-1,1-dimethyl-ethyl)-phenyl]-4,5-dihydro-imidazole-1-carbonyl}-piperazin-1-yl)-1-morpholin-4-yl-ethanone;

cis-2-(4-{4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-N,N-diethyl-isobutyramide;

cis-2-(4-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-phenyl)-N,N-diethyl-isobutyramide;

[(4S,5R)-2-(4-tert-Butyl-2-ethoxy-phenyl)-4,5-bis-(4-fluoro-phenyl)-4,5-dihydro-imidazol-1-yl]-[4-(2-methanesulfonyl-ethyl)-piperazin-1-yl]-methanone hydrochloride;

2-{4-[(4S,5R)-2-(4-tert-Butyl-2,5-diethoxy-phenyl)-4,5-bis-(4-chloro-phenyl)-4,5-dihydro-imidazole-1-carbonyl]-piperazin-1-yl}-1-morpholin-4-yl-ethanone hydrochloride;

4-[(4S,5R)-2-(4-tert-Butyl-2-ethoxy-phenyl)-4,5-bis-(4-chloro-phenyl)-4,5-dihydro-imidazole-1-carbonyl]-piperazine-1-carboxylic acid tert-butyl ester;

1-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-ethanone hydrochloride and 1-{4-[(4S,5R)-2-(4-tert-Butyl-2-ethoxy-phenyl)-4,5-bis-(4-chloro-phenyl)-4,5-dihydro-imidazole-1-carbonyl]-piperazin-1-yl}-2-methoxy-ethanone.

9. A pharmaceutical composition which comprises at least one cis-imidazoline of the formula

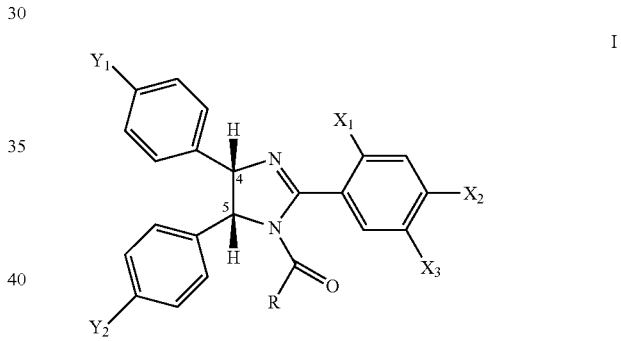

and the pharmaceutically acceptable salts and esters thereof, wherein $X_1$ is selected from the group consisting of lower alkoxy, and lower alkoxy substituted by trifluoromethyl or fluorine;

$X_2$ is selected from the group consisting of hydrogen, halogen, lower alkyl, and —C($X_4X_5$)—$X_6$;

$X_3$ is selected from the group consisting of hydrogen, lower alkoxy, halogen, and —C($X_4X_5$)—$X_6$; with the proviso that when $X_2$ is hydrogen, halogen or lower alkyl, $X_3$ is —C($X_4X_5$)—$X_6$;

$X_4$ and $X_5$ are lower alkyl or together form a cycloalkyl;

$X_6$ is selected from the group consisting of lower alkyl, cyano, —$CH_2$—OH, —$CH_2$—O-lower alkyl, —$CH_2$—O-lower alkyl substituted by lower alkoxy, —C(O)$X_7$, and —$CH_2$—N$X_8X_9$;

$X_7$ is selected from the group consisting of hydroxy, lower alkoxy, morpholino, and —N$X_8X_9$;

$X_8$ and $X_9$ are independently selected from the group consisting of hydrogen, lower alkyl, lower alkyl substituted by lower alkoxy or cyano, and lower alkoxy;

$Y_1$ and $Y_2$ are independently selected from the group consisting of halogen, cyano, and acetylene;

R is

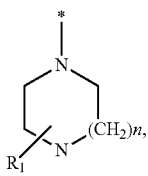

wherein
n=1 or 2,
R$_1$ is lower alkyl substituted by R$_2$;
R$_2$ is selected from the group consisting of lower alkoxy, trifluoromethyl, -cyano, —NH—SO$_2$-lower alkyl, —NH—C(O)-lower alkyl, —C(O)R$_4$, —C(O)—NX$_8$X$_9$, —SO$_2$-lower alkyl and —SO$_2$—NX$_8$X$_9$;
R$_3$ is selected from the group consisting of five membered heterocycle, lower alkyl, lower alkoxy, and lower alkyl substituted by lower alkoxy;
R$_4$ is selected from the group consisting of hydroxy, lower alkoxy, morpholino, and —NX$_8$X$_9$; and wherein the absolute stereochemistry at the 4 and 5 position of the imidazoline ring is S and R respectively
and a pharmaceutically acceptable carrier.

10. A compound of the formula

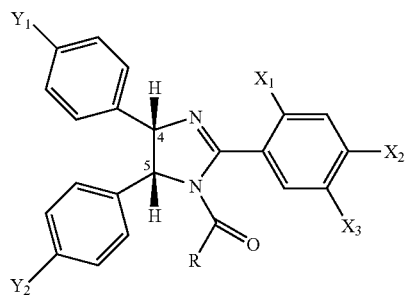

I and the pharmaceutically acceptable salts and esters thereof, wherein
X$_1$ is selected from the group consisting of lower alkoxy, and lower alkoxy substituted by trifluoromethyl or fluorine;
X$_2$ is selected from the group consisting of hydrogen, halogen and lower alkyl,
X$_3$ is C(X$_4$X$_5$)—X$_6$;
X$_4$ and X$_5$ are lower alkyl or together form a cycloalkyl;
X$_6$ is selected from the group consisting of lower alkyl, cyano, —CH$_2$—OH, —CH$_2$—O-lower alkyl, —CH$_2$—O-lower alkyl substituted by lower alkoxy, —C(O)X$_7$, and —CH$_2$—NX$_8$X$_9$;
X$_7$ is selected from the group consisting of hydroxy, lower alkoxy, morpholino, and —NX$_8$X$_9$;
X$_8$ and X$_9$ are independently selected from the group consisting of hydrogen, lower alkyl, lower alkyl substituted by lower alkoxy or cyano, and lower alkoxy;
Y$_1$ and Y$_2$ are independently selected from the group consisting of halogen, cyano, and acetylene;
R is

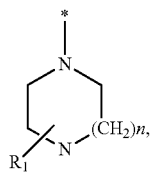

wherein
n=1 or 2,
R$_1$ is lower alkyl substituted by R$_2$;
R$_2$ is selected from the group consisting of lower alkoxy, trifluoromethyl, -cyano, —NH—SO$_2$-lower alkyl, —NH—C(O)-lower alkyl, —C(O)R$_4$, —C(O)—NX$_8$X$_9$, —SO$_2$-lower alkyl and —SO$_2$—NX$_8$X$_9$;
R$_4$ is selected from the group consisting of hydroxy, lower alkoxy, morpholino, and —NX$_8$X$_9$; and wherein the absolute stereochemistry at the 4 and 5 position of the imidazoline ring is S and R respectively.

* * * * *